(12) United States Patent
Oost et al.

(10) Patent No.: US 9,340,507 B2
(45) Date of Patent: May 17, 2016

(54) SUBSTITUTED 4-PYRIDONES AND THEIR USE AS INHIBITORS OF NEUTROPHIL ELASTASE ACTIVITY

(71) Applicant: Boehringer Ingelheim International GmbH, Ingelheim am Rhein (DE)

(72) Inventors: Thorsten Oost, Biberach an der Riss (DE); Dennis Fiegen, Biberach an der Riss (DE); Christian Gnamm, Biberach an der Riss (DE); Sandra Handschuh, Biberach an der Riss (DE); Stefan Peters, Biberach an der Riss (DE); Gerald Juergen Roth, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/843,254

(22) Filed: Sep. 2, 2015

(65) Prior Publication Data
US 2015/0376131 A1    Dec. 31, 2015

Related U.S. Application Data

(63) Continuation of application No. 13/971,374, filed on Aug. 20, 2013, now abandoned.

(30) Foreign Application Priority Data

Aug. 23, 2012 (EP) .................................... 12181541

(51) Int. Cl.
| | |
|---|---|
| A61K 31/54 | (2006.01) |
| A61K 31/50 | (2006.01) |
| A61K 31/501 | (2006.01) |
| A61K 38/00 | (2006.01) |
| A61P 11/06 | (2006.01) |
| A61P 17/00 | (2006.01) |
| A61P 29/00 | (2006.01) |
| C07D 215/00 | (2006.01) |
| C07D 213/62 | (2006.01) |
| C07D 213/82 | (2006.01) |
| C07D 405/04 | (2006.01) |
| C07D 405/06 | (2006.01) |
| C07D 405/14 | (2006.01) |
| C07D 409/12 | (2006.01) |
| C07D 409/14 | (2006.01) |
| C07D 413/12 | (2006.01) |
| C07D 471/04 | (2006.01) |
| C07D 513/04 | (2006.01) |
| C07D 401/12 | (2006.01) |

(52) U.S. Cl.
CPC ............ *C07D 213/82* (2013.01); *C07D 401/12* (2013.01); *C07D 405/04* (2013.01); *C07D 405/06* (2013.01); *C07D 405/14* (2013.01); *C07D 409/12* (2013.01); *C07D 409/14* (2013.01); *C07D 413/12* (2013.01); *C07D 471/04* (2013.01); *C07D 513/04* (2013.01)

(58) Field of Classification Search
None
See application file for complete search history.

(56) References Cited

U.S. PATENT DOCUMENTS

| 4,844,732 A | 7/1989 | Goto et al. |
|---|---|---|
| 2006/0035938 A1 | 2/2006 | Bladh et al. |
| 2012/0149735 A1 | 6/2012 | Millet et al. |

FOREIGN PATENT DOCUMENTS

| EP | 1562902 A1 | 8/2005 |
|---|---|---|
| EP | 2261211 A1 | 12/2010 |
| WO | 2006098683 A1 | 9/2006 |
| WO | 2009094417 A1 | 7/2009 |

OTHER PUBLICATIONS

International Search Report, form PCT/ISA/210, and Written Opinion, form PCT/ISA/237, for corresponding application PCT/EP2013/067427, date of mailing Oct. 2, 2013.

*Primary Examiner* — Jeffrey S Lundgren
*Assistant Examiner* — Tori M Strong
(74) *Attorney, Agent, or Firm* — Michael P. Morris; Edward S. Lazer

(57) ABSTRACT

This invention relates to substituted 4-pyridones of formula 1

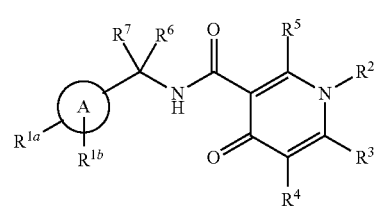

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

2 Claims, No Drawings

SUBSTITUTED 4-PYRIDONES AND THEIR USE AS INHIBITORS OF NEUTROPHIL ELASTASE ACTIVITY

FIELD OF THE INVENTION

This invention relates to substituted 4-pyridones and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other auto-immune and allergic disorders, allograft rejection, and oncological diseases.

BACKGROUND INFORMATION

The following references describe neutrophil elastase inhibitors with a 2-pyridone central core: WO04043924, WO05026123, WO05026124, WO06098683, WO06098684, WO07129962, WO10094964, WO11039528.

The following references describe neutrophil elastase inhibitors with a 2-pyrazinone central core: WO07129963, WO09061271, WO09058076, WO11110852.

For a review on various inhibitors of neutrophil elastase see: P. Sjö (*Future Med. Chem.* 2012, 4, 651-660).

BRIEF SUMMARY OF THE INVENTION

Neutrophil elastase is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of monocytes and vascular smooth muscle cells and directly effects components of the coagulation and fibrinolytic pathways (PAI-1 and TFPI. Increased activity of neutrophil elastase is associated with chronic inflammatory and fibrotic diseases of several organs. Inhibitors of neutrophil elastase will therefore have an important role for the treatment of different diseases like COPD, fibrosis, cancer and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al., J. Pharm. Exp. Ther. 339, 313-320 (2011).

Some compounds according to the present invention, including the physiologically acceptable salts, exhibit favourable in vivo potency, as determined, for example, by the half maximal effective dose ($ED_{50}$), in a model of human neutrophil elastase-induced lung injury in mice, for instacnc as described in Tremblay et al., Chest 121, 582-588 (2002) or T. Stevens et al. (*J. Pharm. Exp. Ther.* 2011, 339, 313-320).

Some compounds according to the present invention, including the physiologically acceptable salts, exhibit favourable metabolic stability in an in vitro microsomal assay for metabolic stability as described in E. Kerns & L. Di, Drug-like properties: concepts, structure design and methods: from ADME to toxicity optimization, Elsevier, $1^{st}$ ed, 2008, chapter 29 and references therein.

Some compounds according to the present invention, including the physiologically acceptable salts, exhibit favourable metabolic stability in an in vitro hepatocytes assay for metabolic stability as described in E. Kerns & L. Di, Drug-like properties: concepts, structure design and methods: from ADME to toxicity optimization, Elsevier, $1^{st}$ ed, 2008, chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}$=Dose/AUC ($F_{oral}$: oral bioavailability, AUC: area under the curve), a reduced in vivo clearance is expected lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di, Drug-like properties: concepts, structure design and methods: from ADME to toxicity optimization, Elsevier, $1^{st}$ ed, 2008, chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di, Drug-like properties: concepts, structure design and methods: from ADME to toxicity optimization, Elsevier, $1^{st}$ ed, 2008, chapter 25 and references therein. For an oral drug, improved aqueous solubility is expected to translate into a higher fraction of the drug absorbed in the intestinal tract resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or longer duration of action of the drug when the same dose is applied.

Some compounds according to the present invention, including the physiologically acceptable salts, exhibit favourable metabolic stability, favourable permeability and favourable aqueous solubility. Accordingly, some compounds of the present invention are expected to exhibit favourable pharmacokinetic (PK) properties, in particular favourable systemic exposure (area under the curve, AUC).

Some compounds according to the present invention, including the physiologically acceptable salts, exhibit favourable pharmacokinetic (PK) properties. The PK properties can be determined in pre-clinical animal species, for example mouse, rat, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL), bioavailability after oral administration ($F_{oral}$).

DETAILED DESCRIPTION OF THE INVENTION

Compounds of formula 1

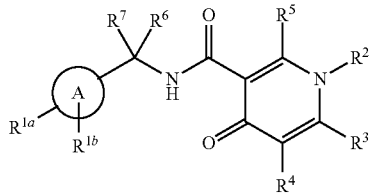

wherein

A is phenyl or a five- or six-membered, aromatic heteroring, wherein one, two or three elements are replaced by an element selected independent from each other from the group consisting of N, O, S and (O⁻N⁺); or
  a ring system of two fused five- or six-membered, aromatic heterorings, wherein one, two or three elements are replaced by an element selected independent from each other from the group consisting of N, O, S, (O)$_2$S and (O⁻N⁺);

$R^{1a}$ is H, $C_{1-4}$-haloalkyl-, $C_{3-6}$-cyloalkyl-, NC—, $C_{1-4}$-alkyl-(O)S—, $C_{1-4}$-alkyl-(O)$_2$S—, $C_{3-6}$-cycloalkyl-(O)S—, $C_{3-6}$-cycloalkyl-(O)$_2$S—, $C_{1-4}$-haloalkyl-(O)S—, $C_{1-4}$-haloalkyl-(O)$_2$S—, $H_2N(O)_2S$—, $R^{1a.1}$;
  $R^{1a.1}$ is a five- or six-membered, aromatic or non-aromatic heteroring, wherein one, two or three elements are replaced by an element selected independent from each other from the group consisting of N and O; optionally substituted with O= or $C_{1-4}$-Alkyl-;

$R^{1b}$ is H, O=, halogen, $C_{1-4}$-alkyl-O— or $C_{1-4}$-alkyl-, preferably H, F or methyl;
  or $R^{1a}$ and $R^{1b}$ are together $C_{2-4}$-alkylene forming a carbocyclic heteroring, wherein one element of the ring is replaced by (O)$_2$S;

$R^2$ is $C_{1-6}$-alkyl-, $C_{1-6}$-haloalkyl-, $C_{1-4}$-alkyl-O—$C_{1-4}$-alkyl- or a ring selected from the group consisting of $C_{3-6}$-cycloalkyl-, $C_{3-6}$-halocycloalkyl-, $C_{3-6}$-cycloalkyl-$C_{1-4}$-alkyl-, $C_{3-6}$-halocycloalkyl-$C_{1-4}$-alkyl-; wherein one element of the above mentioned rings is optionally replaced by O;

$R^3$ is $C_{1-4}$-alkyl-;

$R^4$ is phenyl or a five- or six-membered, aromatic heteroring, wherein one or two elements are replaced by an element selected independent from each other from the group consisting of N, O and S; each element of one of the rings optionally substituted with a residue selected from the group consisting of $C_{1-4}$-alkyl-, $C_{3-6}$-cycloalkyl-, $C_{1-4}$-haloalkyl- and halogen;

$R^5$ is H, $C_{1-4}$-haloalkyl- and $C_{3-6}$-cycloalkyl-;
$R^6$ is H,
$R^7$ is H, $C_{1-4}$-alkyl;
  or $R^6$ and $R^7$ are together $C_{2-5}$-alkylene forming a carbocyclic ring;
or a salt thereof.

PREFERRED EMBODIMENTS

Preferably A is phenyl or a five- or six-membered, aromatic heteroring, wherein one, two or three elements are replaced by an element selected independent from each other from the group consisting of N, O, S and (O⁻N⁺);

Preferably A is a ring system of two fused five- or six-membered, aromatic heterorings, wherein one, two or three elements are replaced by an element selected independent from each other from the group consisting of N, O, S and (O⁻N⁺);

Preferred are the above compounds of formula 1, wherein
A is phenyl or a five- or six-membered, aromatic heteroring, wherein one, two or three elements are replaced by an element selected independent from each other from the group consisting of N and O;
$R^{1a}$ is $C_{1-4}$-alkyl-(O)S—, $C_{1-4}$-alkyl-(O)$_2$S—;
$R^{1b}$ is H, halogen, $C_{1-4}$-alkyl-O— or $C_{1-4}$-alkyl-, preferably H, F or methyl;
$R^2$ is $C_{1-6}$-alkyl- or $C_{3-6}$-cycloalkyl-, wherein one element of the above mentioned rings is optionally replaced by O;
$R^3$ is $C_{1-4}$-alkyl-;
$R^4$ is phenyl or a six-membered, aromatic heteroring, wherein one or two elements are replaced by an element selected independent from each other from the group consisting of N; each element of one of the rings optionally substituted with $C_{1-4}$-haloalkyl-;
or a salt thereof and $R^5$, $R^6$ and $R^7$ have the above given meaning, preferably they are all H.

Preferred are the above compounds of formula 1, wherein
A is phenyl or a five- or six-membered, aromatic heteroring, wherein one, two or three elements are replaced by an element selected independent from each other from the group consisting of N and O;
$R^{1a}$ is $C_{1-4}$-alkyl-(O)S—, $C_{1-4}$-alkyl-(O)$_2$S—; preferably $H_3C$—(O)S— or $H_3C$—(O)$_2$S—;
$R^{1b}$ is H, F or methyl;
$R^2$ is $C_{1-6}$-alkyl- or $C_{3-6}$-cycloalkyl-, wherein one element of the above mentioned rings is optionally replaced by O;
$R^3$ is $C_{1-4}$-alkyl-; preferably methyl;
$R^4$ is phenyl, optionally substituted with $C_{1-4}$-haloalkyl-, preferably $HF_2C$— or $F_3C$;
or a salt thereof and $R^5$, $R^6$ and $R^7$ have the above given meaning, preferably they are all H.

Preferred are the above compounds of formula 1, wherein
A is phenyl or pyridinyl;
$R^{1a}$ is $C_{1-4}$-alkyl-(O)$_2$S—; preferably $H_3C$—(O)$_2$S—;
$R^{1b}$ is H, F or methyl;
$R^2$ is methyl, ethyl, n-propyl, i-propyl or sec-butyl; preferably ethyl or i-propyl;
$R^3$ is methyl;
$R^4$ is phenyl, optionally substituted with $HF_2C$— or $F_3C$, preferably $HF_2C$—;
or a salt thereof and $R^5$, $R^6$ and $R^7$ have the above given meaning, preferably they are all H.

Preferred are the above compounds of formula 1, wherein
A is phenyl or a five- or six-membered, aromatic heteroring, wherein one or two or three elements are replaced by an element selected independent from each other from the group consisting of N, O, S and (O⁻N⁺); or
$R^{1a}$ is H, $C_{1-4}$-alkyl-, NC—, $C_{1-4}$-alkyl-(O)S—, $C_{1-4}$-alkyl-(O)$_2$S—, $H_2N(O)_2S$—, $R^{1a.1}$—$C_{1-4}$-alkyl-, $R^{1a.1}$;
  $R^{1a.1}$ is a five- or six-membered, aromatic or non-aromatic heteroring, wherein one or two elements are replaced by an element selected independent from each other from the group consisting of N and O; optionally substituted with O=;
$R^{1b}$ is H, halogen or $C_{1-4}$-alkyl-, preferably H, F or methyl
  or $R^{1a}$ and $R^{1b}$ are together $C_{2-4}$-alkylene forming a carbocyclic ring, wherein one element of the ring is replaced by (O)$_2$S;
$R^2$ is $C_{1-6}$-alkyl-, $C_{1-6}$-haloalkyl-, $C_{1-4}$-alkyl-O—$C_{1-4}$-alkyl- or a ring selected from the group consisting of $C_{3-6}$-cycloalkyl-, C$_{3-6}$-halocycloalkyl-, C$_{3-6}$-cycloalkyl-C$_{1-4}$-alkyl-, C$_{3-6}$-halocycloalkyl-C$_{1-4}$-alkyl-; wherein one element of the above mentioned rings is optionally replaced by O;

R$^3$ is C$_{1-4}$-alkyl-;

R$^4$ is phenyl or a five- or six-membered, aromatic heteroring, wherein one or two elements are replaced by an element selected independent from each other from the group consisting of N and O; wherein one or two elements of one of the rings are optionally substituted with a residue selected from the group consisting of C$_{1-4}$-alkyl-, C$_{1-4}$-haloalkyl- and halogen;

or a salt thereof and R$^5$, R$^6$ and R$^7$ have the above given meaning, preferably they are all H.

Preferred are the above compounds of formula 1, wherein A is phenyl, pyrazolyl, oxadiazolyl, pyridinyl, pyridin-N-oxidyl, thiophenyl;

R$^{1a}$ is H, methyl, NC—, Me(O)S—, Me(O)$_2$S—, Et(O)$_2$S—, H$_2$N(O)$_2$S—, imidazolidin-onyl, pyrrolidinon-H$_2$C—, imidazol-H$_2$C—;

R$^{1b}$ is H;

or R$^{1a}$ and R$^{1b}$ are together C$_3$-alkylene forming a carbocyclic ring, wherein one element of the ring is replaced by (O)$_2$S;

R$^2$ is C$_{1-6}$-alkyl-, C$_{3-6}$-cycloalkyl-, C$_{3-6}$-cycloalkyl-H$_2$C—, tetrahydrofuranyl, tetrahydrofuran-H$_2$C—, each optionally substituted with one or two residues selected from the group consisting of F;

R$^3$ is methyl;

R$^4$ is phenyl or pyridinyl, both optionally substituted with a residue selected from the group consisting of F$_2$HC—, F$_3$C—;

or a salt thereof and R$^5$, R$^6$ and R$^7$ have the above given meaning, preferably they are all H.

Preferred are the above compounds of formula 1, wherein A is phenyl, oxadiazolyl, pyridinyl, pyridin-N-oxidyl, thiophenyl;

R$^{1a}$ is H, methyl, NC—, Me(O)S—, Me(O)$_2$S—, Et(O)$_2$S—, H$_2$N(O)$_2$S—, imidazolidin-onyl, pyrrolidinon-H$_2$C—, imidazol-H$_2$C—;

R$^{1b}$ is H;

or R$^{1a}$ and R$^{1b}$ are together C$_3$ alkylene forming a carbocyclic ring, wherein one element of the ring is replaced by (O)$_2$S;

R$^2$ is ethyl, n-propyl, i-propyl, 1-methyl-propyl, 1-ethyl-propyl, cyclopropanyl, cyclobutanyl, cyclopentanyl, tetrahydrofuranyl, each optionally substituted with one or two F;

R$^3$ is methyl;

R$^4$ is phenyl or pyridinyl, both substituted, preferably in meta position, with a residue selected from the group consisting of F$_2$HC—, F$_3$C—;

or a salt thereof and R$^5$, R$^6$ and R$^7$ have the above given meaning, preferably they are all H.

Preferred are the above compounds of formula 1, wherein A is phenyl, oxadiazolyl, pyridinyl, pyridin-N-oxidyl, thiophenyl;

R$^{1a}$ is H, methyl, NC—, Me(O)S—, Me(O)$_2$S—, Et(O)$_2$S—, H$_2$N(O)$_2$S—, imidazolidin-onyl, pyrrolidinon-H$_2$C—, imidazol-H$_2$C—;

R$^{1b}$ is H;

R$^2$ is i-propyl;

R$^3$ is methyl;

R$^4$ is phenyl or pyridinyl, both substituted, preferably in meta position, with a residue selected from the group consisting of F$_2$HC—, F$_3$C—;

or a salt thereof and R$^5$, R$^6$ and R$^7$ have the above given meaning, preferably they are all H.

Preferred are the above compounds of formula 1, wherein A is phenyl or pyridinyl;

R$^{1a}$ is Me(O)$_2$S—;

R$^{1b}$ is H;

and R$^2$, R$^3$, R$^4$, R$^5$, R$^6$ and R$^7$ have the above given meaning.

In a preferred embodiment of the invention R$^4$ is one of the above mentioned rings carrying the above mentioned optional substituted in meta-position to the element connection R$^4$ with the compound of formula 1.

From the above mentioned compounds those are preferred wherein R$^4$ is

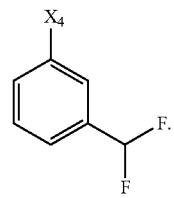

From the above mentioned compounds those are preferred wherein R$^4$ is

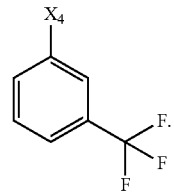

From the above mentioned compounds those are preferred wherein R$^4$ is

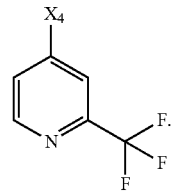

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, C$_{1-6}$-alkyl means an alkyl group or radical having 1 to 6 carbon atoms.

In general in single groups like HO, H$_2$N, OS, O$_2$S, NC (cyano), HOOC, F$_3$C or the like, the skilled artisan can see the radical attachment point(s) to the molecule from the free valences of the group itself. For combined groups comprising two or more subgroups, the last named subgroup is the radical attachment point, for example, the substituent "aryl-C$_{1-3}$-alkyl-" means an aryl group which is bound to a C$_{1-3}$-alkylgroup, the latter of which is bound to the core or to the group to which the substituent is attached.

In case a compound of the present invention is depicted in form of a chemical name and as a formula in case of any discrepancy the formula shall prevail. An asterisk, a dashed or a dotted line may be used in sub-formulas to indicate the bond which is connected to the core molecule as defined.

For example, the term "3-carboxypropyl-group" represents the following substituent:

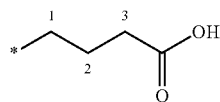

wherein the carboxy group is attached to the third carbon atom of the propyl group. The terms "1-methylpropyl-", "2,2-dimethylpropyl-" or "cyclopropylmethyl-" group represent the following groups:

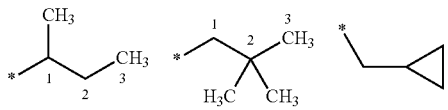

The asterisk, dashed or dotted line may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

When in the claimed ring system A (e.g. SA) the two residues $R^{1a}$ and $R^{1b}$ are "together a $C_{2-4}$-alkylene forming a carbocyclic ring, wherein one element of the ring is replaced by $(O)_2S$; rings similar to example SB are meant in this case $R^{1a}$ and $R^{1b}$ are in ortho position to each other.

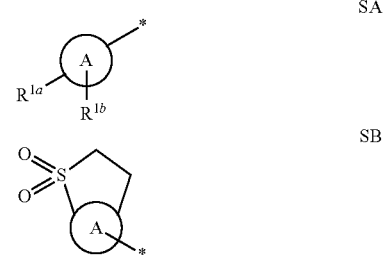

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to 4 or 6 (preferably 4), either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{n-m}$-alkylene" wherein n is an integer 2 or 3 and m is 4 or 5, either alone or in combination with another radical, denotes an acyclic, straight or branched chain divalent alkyl radical containing from 2 to 5 carbon atoms. For example the term $C_{2-4}$-alkylene includes —CH$_2$—CH$_2$—, —CH(CH$_3$)—, —CH$_2$—CH$_2$—CH$_2$—, —C(CH$_3$)$_2$—, —CH(CH$_2$CH$_3$)—, —CH(CH$_3$)—CH$_2$—, —CH$_2$—CH(CH$_3$)—, —CH$_2$—CH$_2$—CH$_2$—CH$_2$—, —CH$_2$—CH$_2$—CH(CH$_3$)—, —CH(CH$_3$)—CH$_2$—CH$_2$—, —CH$_2$—CH —CH(CH$_3$)—CH$_2$—, —CH$_2$—C(CH$_3$)$_2$—, —C(CH$_3$)$_2$—CH$_2$—, —CH(CH$_3$)—CH(CH$_3$)—, —CH$_2$—CH(C H$_2$CH$_3$)—, —CH(CH$_2$CH$_3$)—CH$_2$—, —CH(CH$_2$CH$_2$CH$_3$)—, —CH(CH(CH$_3$)$_2$)— and —C(CH$_3$)(CH$_2$C H$_3$)—.

By the term "halo" added to a "alkyl", "alkylene" or "cycloalkyl" group (saturated or unsaturated) is such a alkyl or cycloalkyl group meant wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

The term "$C_{3-n}$-cycloalkyl", wherein n is an integer from 4 to 6, either alone or in combination with another radical denotes a cyclic, saturated, unbranched hydrocarbon radical with 3 to n C atoms. For example the term $C_{3-6}$-cycloalkyl includes cyclopropyl, cyclobutyl, cyclopentyl and cyclohexyl.

The term "aryl" as used herein, either alone or in combination with another radical, denotes a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

With the elements of a ring the atoms forming this ring are meant. So, a phenyl ring contains 6 elements which are all carbon atoms, a pyrrol ring contains 5 elements, wherein 4 elements are carbon atoms and the remaining element is a nitrogen atom.

The term "non-aromatic heteroring" means a saturated, partially saturated or unsaturated monocyclic-ring systems containing one, two, three or four heteroatoms selected from N, (O⁻)N⁺, O or (O)$_r$S, wherein r=0, 1 or 2, consisting of four, five or six ring atoms. If the term is connected with a more detailed definition of the amount or kind of heteroatoms and the possible size of the non-aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

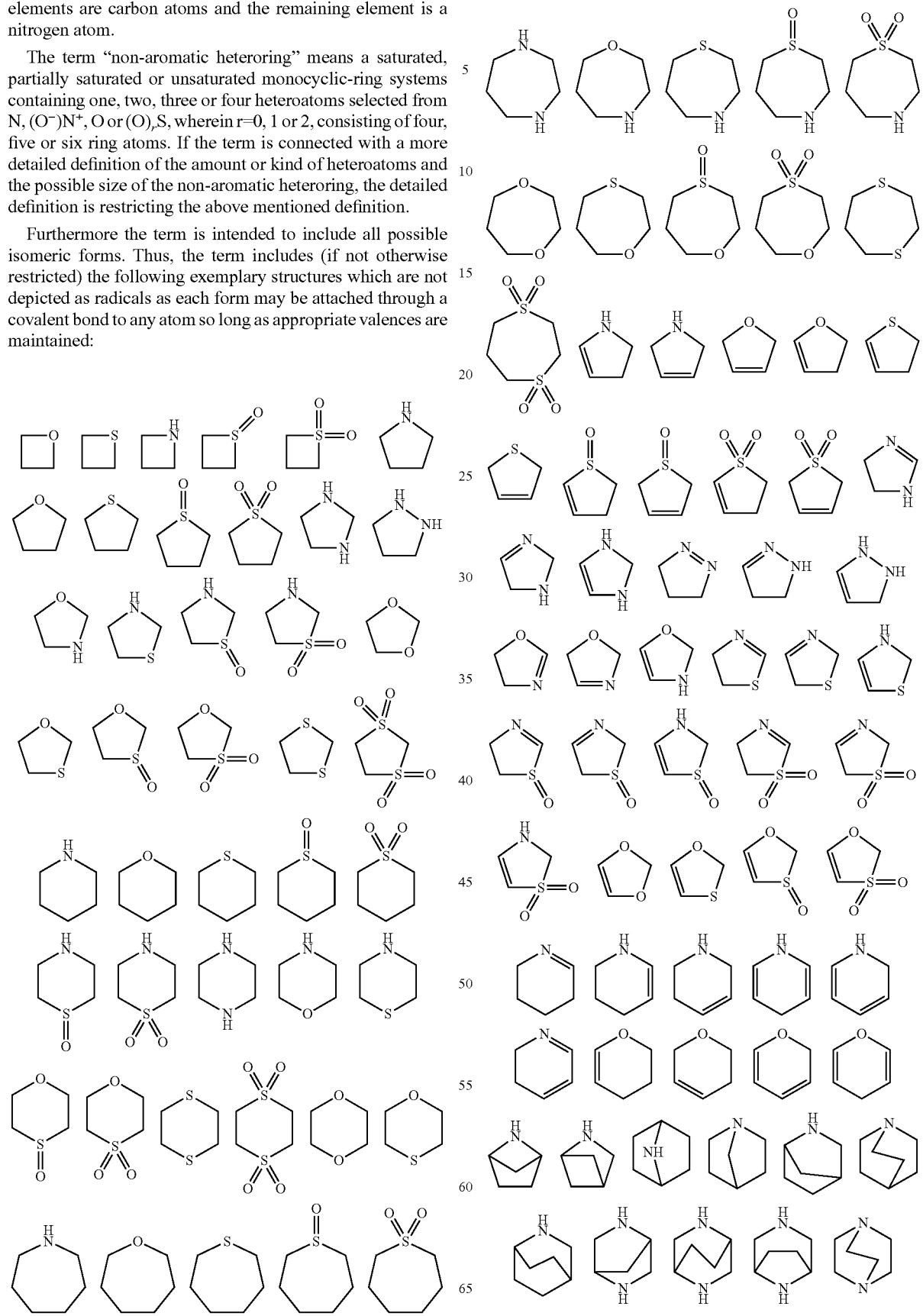

-continued

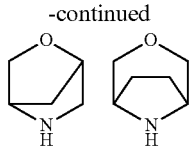

The term "aromatic heteroring" means a unsaturated monocyclic-ring systems containing one, two, three or four heteroatoms selected from N, (O⁻)N⁺, O or (O)$_r$S, wherein r=0, 1 or 2, consisting of four, five or six ring atoms. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

The term "ring system of two fused aromatic or non-aromatic heterorings" means a saturated or unsaturated polycyclic-ring systems including aromatic heteroring system containing one or more heteroatoms selected from N, O or S(O)$_r$, wherein r=0, 1 or 2, consisting of 8 to 14 ring atoms, preferably 8 to 10 ring atoms, wherein none of the heteroatoms is part of the aromatic heteroring. If the term is connected with a more detailed definition of the amount or kind of heteroatoms and the possible size of the aromatic heteroring, the detailed definition is restricting the above mentioned definition.

Furthermore the term is intended to include all possible isomeric forms. Thus, the term includes (if not otherwise restricted) the following exemplary structures which are not depicted as radicals as each form may be attached through a covalent bond to any atom so long as appropriate valences are maintained:

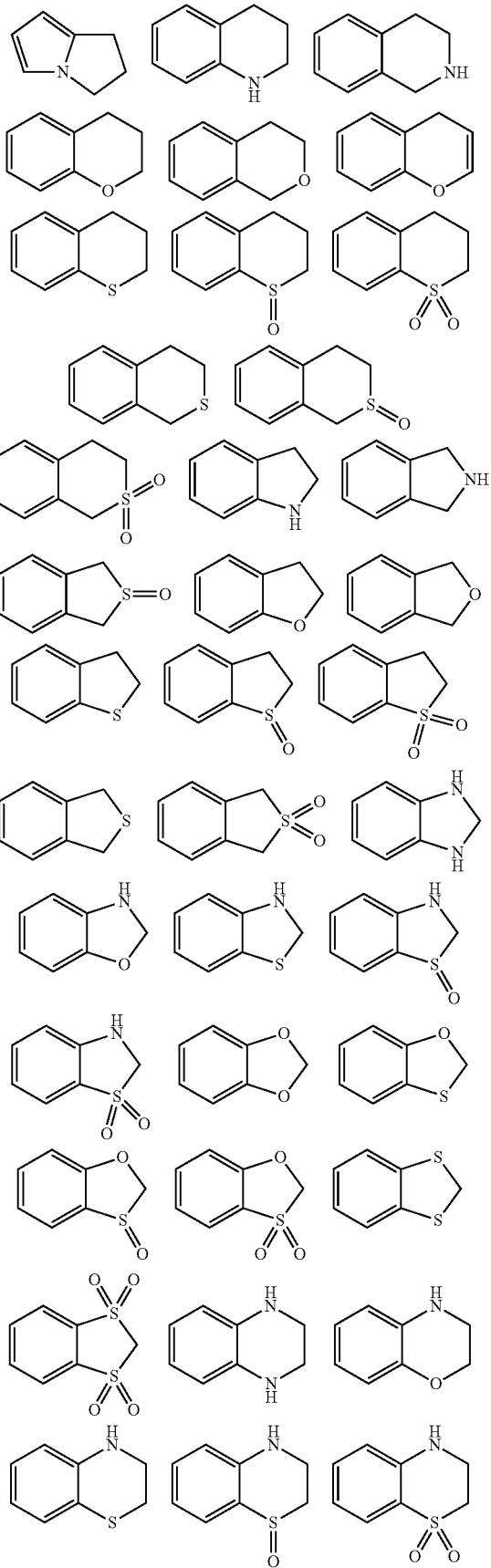

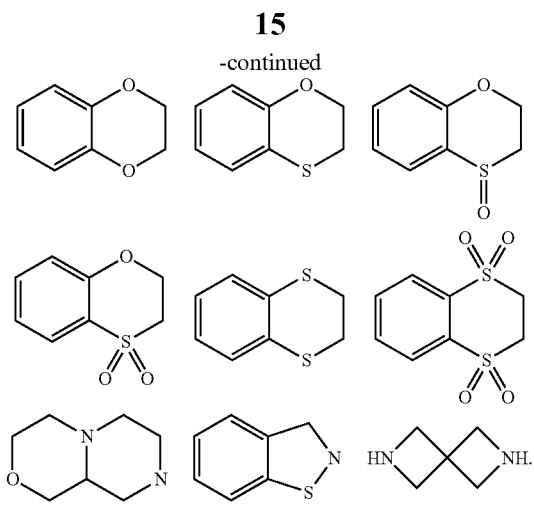
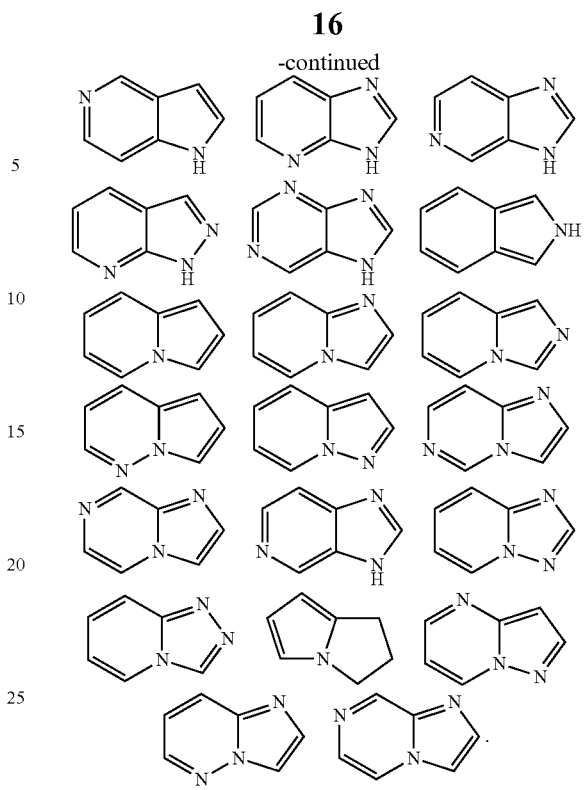

The following examples are also part of the term group defined with the term "ring system of two fused aromatic or non-aromatic heterorings", but are also a subgroup called "ring system of two fused aromatic heterorings"

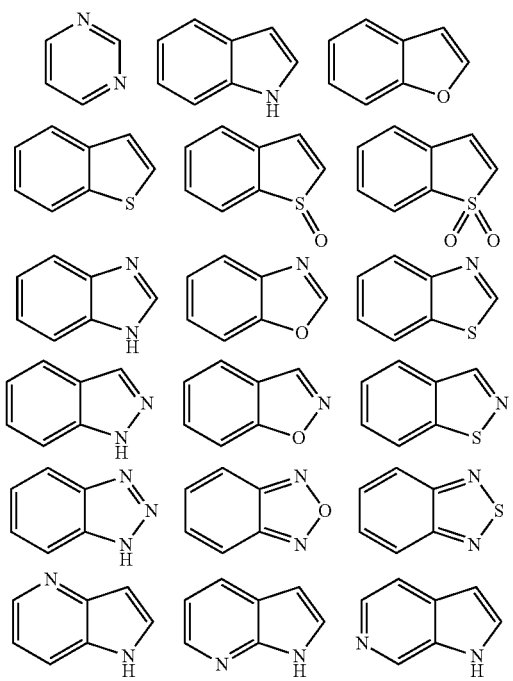

Preparation

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner Any functional groups in the starting materials or intermediates may be protected using conventional protecting groups. These protecting groups may be cleaved again at a suitable stage within the reaction sequence using methods familiar to the one skilled in the art.

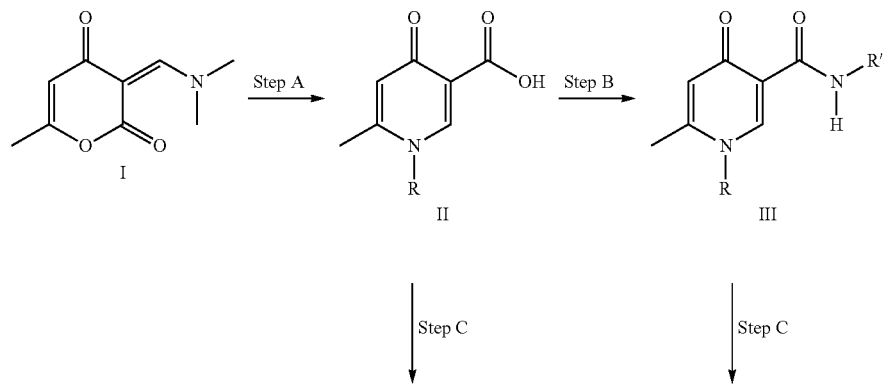

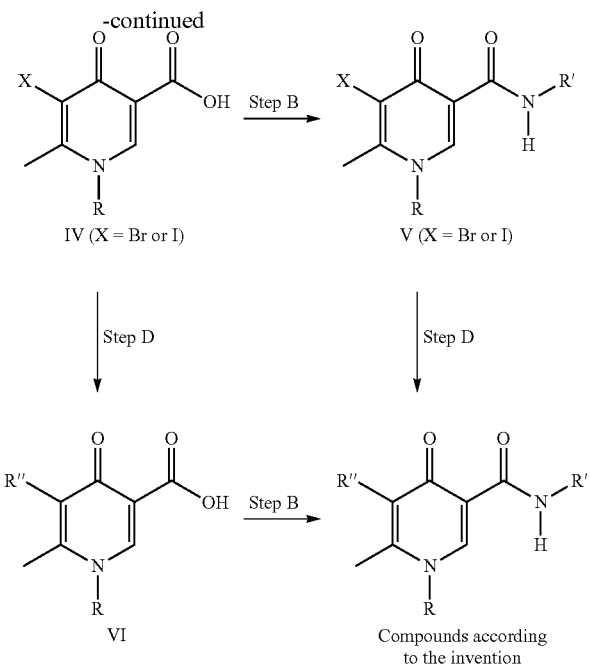

Starting material I can be prepared as described in US2003/87940.

Intermediates II can be prepared as described in WO10133973 and US2003/87940 by heating starting material I with amines R—NH₂ in the presence of a strong base, for example sodium tert-butoxide or sodium ethoxide, in an organic solvent, for example ethanol. The reaction usually takes place within 2 to 72 hours. Preferred reaction temperatures are between 50° C. and 150° C.

The amide coupling (Step B, intermediates II→intermediates III, intermediates IV→intermediates V, intermediates VI→compounds of the invention) can be achieved by reacting carboxylic acid intermediates II, IV or VI with amines R'—NH₂ in the presence of an amide coupling reagent, for example O-(Benzotriazol-1-yl)-N,N,N',N'-tetramethyluronium hexafluorophosphate (HBTU) or O-(Benzotriazol-1-yl)-N,N,N',N'-tetramethyluronium tetrafluoroborate (TBTU) or propylphosphonic anhydride (PPA), and in the presence of a base, for example triethylamine, diisopropylethylamine (DIPEA, Hünig's base) or N-methyl-morpholine, in an organic solvent, for example dichloromethane, acetonitrile, N,N-dimethylformamide (DMF), N-methyl-2-pyrrolidone (NMP) or dimethylacetamide (DMA) or mixtures thereof. The reaction usually takes place within 1 to 72 hours. Preferred reaction temperatures are between 0° C. and 50° C., most preferred room temperature. Alternatively, the carboxylic acid intermediates can be activated first as described in US2003/87940, for example with 1,1'-carbonyldiimidazole (CDI) in DMF, followed by reaction with the amine R'—NH₂.

The bromination (Step C, X═Br, intermediates II→intermediates IV, intermediates III→intermediates V) can be achieved by reacting intermediates II or III with bromination agents, for example bromine or N-bromosuccinimide, in an organic solvent, for example acetic acid, dichloromethane, methanol, acetonitrile, tetrahydrofuran or mixtures thereof. The iodination (Step C, X═I, intermediates II→intermediates IV, intermediates III→intermediates V) can be achieved by reacting intermediates II or III with iodination agents, for example iodine, iodinechloride (I—Cl) or N-iodosuccinimide, in an organic solvent, for example acetic acid, methanol, ethanol, dichloromethane, acetonitrile, N,N-dimethyl-formamide, tetrahydrofuran or mixtures thereof. The halogenation reaction usually takes place within 1 to 72 hours. Preferred reaction temperatures are between 0° C. and 50° C., most preferred room temperature.

The Suzuki coupling (Step D, intermediates IV→intermediates VI, intermediates V→compounds according to the invention) can be achieved by reacting intermediates IV or V with aryl or heteroaryl boronic acids R"—B(OH)₂ or the corresponding boronic esters in the presence of a palladium catalyst, for example tetrakis(triphenylphosphine)palladium(O) or [1,1'-bis(diphenylphosphino)ferrocene]dichloropalladium(II), and in the presence of a base, for example, potassium carbonate, barium dihydroxide or cesium carbonate, in an organic solvent, for example toluene, benzene, ethanol, ethylene glycol dimethyl ether, acetonitrile, dioxane or mixtures thereof, optionally in the presence of water. The reaction usually takes place within 1 to 72 hours. Preferred reaction temperatures are between 50° C. and 150° C.

Compounds according to the present invention can also be prepared according to the following scheme starting from 4-hydroxy-6-methyl-nicotinic acid. Halogenation (Step C) as described above, followed by Suzuki coupling (Step D) as described above, followed by amide coupling (Step B) as described above, yields intermediates VII. The alkylation of the pyridone nitrogen (Step E) can be achieved by reacting intermediate VII with alkylating agents, for example alkyl bromides, alkyl iodides, alkyl tosylates, alkyl mesylates or dialkyl sulfates, in the presence of a base, for example sodium carbonate, potassium carbonate, potassium hydroxide, sodium hydroxide or cesium carbonate, in an organic solvent, N,N-dimethylformamide (DMF), N-methyl-2-pyrrolidone (NMP) or dimethylacetamide (DMA). The reaction usually takes place within 1 to 72 hours. Preferred reaction temperatures are between 50° C. and 150° C.

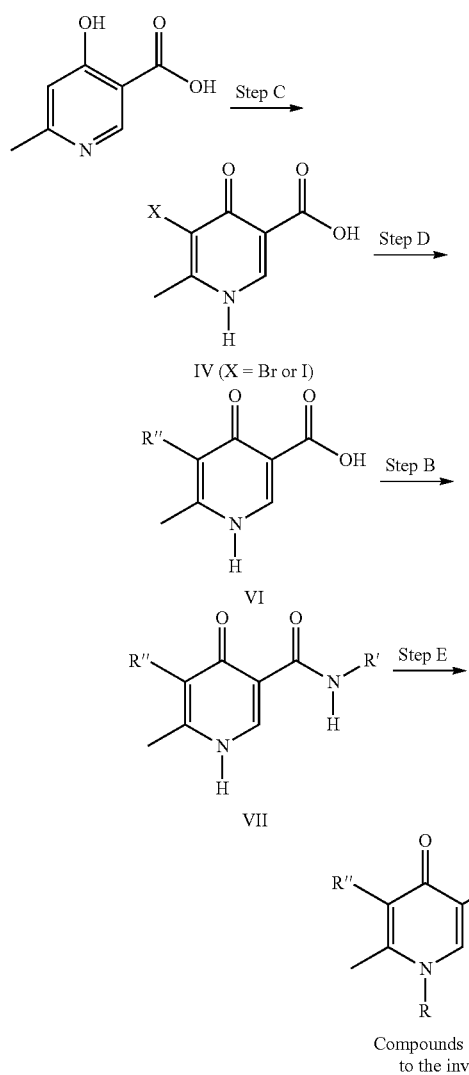

Compounds according to the invention

The intermediates for compounds according to the present invention with 2-alkyl substituents can be prepared according to Venkatramani et al., J. Het. Chem. 30, 723-738 (1993).

Preliminary Remarks:

The HPLC data given are measured under the following conditions:

| Method Name: | V003_003 |
| --- | --- |
| Column: | XBridge C18, 4.6 × 30 mm, 3.5 μm |
| Column Supplier: | Waters |

| Gradient/Solvent Time [min] | % Sol [H2O, 0.1% NH3] | % Sol [Methanol] | Flow [ml/min] | Temp [° C.] |
| --- | --- | --- | --- | --- |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

| Method Name: | Z002_002 |
| --- | --- |
| Column: | Sunfire C18, 3 × 30 mm, 2.5 μm |
| Column Supplier: | Waters |

| Gradient/Solvent Time [min] | % Sol [H2O, 0.1% TFA] | % Sol [Methanol] | Flow [ml/min] | Temp [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | Z002_005 |
| --- | --- |
| Column: | Sunfire C18, 3 × 30 mm, 2.5 μm |
| Column Supplier: | Waters |

| Gradient/Solvent Time [min] | % Sol [H2O, 0.1% TFA] | % Sol [Methanol] | Flow [ml/min] | Temp [° C.] |
| --- | --- | --- | --- | --- |
| 0.0 | 95 | 5 | 1.8 | 60 |
| 0.25 | 95 | 5 | 1.8 | 60 |
| 1.70 | 0 | 100 | 1.8 | 60 |
| 1.75 | 0 | 100 | 2.5 | 60 |
| 1.90 | 0 | 100 | 2.5 | 60 |

| Method Name: | Z002_006 |
| --- | --- |
| Column: | Sunfire C18, 3 × 30 mm, 2.5 μm |
| Column Supplier: | Waters |

| Gradient/Solvent Time [min] | % Sol [H2O, 0.1% TFA] | % Sol [Methanol] | Flow [ml/min] | Temp [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method Name: | Z002_007 |
| --- | --- |
| Column: | Sunfire C18, 3 × 30 mm, 2.5 μm |
| Column Supplier: | Waters |

| Gradient/Solvent Time [min] | % Sol [H2O, 0.1% TFA] | % Sol [Methanol] | Flow [ml/min] | Temp [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method Name: | Z003_001 |
| --- | --- |
| Column: | XBridge C18, 3 × 30 mm, 2.5 μm |
| Column Supplier: | Waters |

| Gradient/Solvent Time [min] | % Sol [H2O, 0.1% NH3] | % Sol [Methanol] | Flow [ml/min] | Temp [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method Name: | Z003_003 |
| --- | --- |
| Column: | XBridge C18, 3 × 30 mm, 2.5 μm |
| Column Supplier: | Waters |

-continued

| Method Name: | Z011_S03 |
| --- | --- |
| Column: | XBridge C18, 3 × 30 mm, 2.5 μm |
| Column Supplier: | Waters |

| Gradient/Solvent Time [min] | % Sol [H2O, 0.1% NH3] | % Sol [Methanol] | Flow [ml/min] | Temp [° C.] |
| --- | --- | --- | --- | --- |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

| Method Name: | Z011_S03 |
| --- | --- |
| Column: | XBridge C18, 3 × 30 mm, 2.5 μm |
| Column Supplier: | Waters |

| Gradient/Solvent Time [min] | % Sol [H2O, 0.1% NH3] | % Sol [Acetonitrile] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z012_S04 |
| --- | --- |
| Column: | XBridgeC18, 3 × 30 mm, 2.5 μm |
| Column Supplier: | Waters |

| Gradient/Solvent Time [min] | % Sol [H2O, 0.1% TFA] | % Sol [Acetonitril] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | Z018_S04 |
| --- | --- |
| Column: | Sunfire, 3 × 30 mm, 2.5 μm |
| Column Supplier: | Waters |

| Gradient/Solvent Time [min] | % Sol [H2O, 0.1% TFA] | % Sol [Acetonitrile] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | 001_CA04 |
| --- | --- |
| Column: | XBridge C18_4.6 × 30 mm, 3.5 μm |
| Column Supplier: | Waters |

| Gradient/Solvent Time [min] | % Sol [H2O 0.1% NH4OH] | % Sol [Methanol] | Flow [ml/min] | Temp [° C.] |
| --- | --- | --- | --- | --- |
| 0.0 | 80 | 20 | 2.0 | 60 |
| 1.7 | 0 | 100 | 2.0 | 60 |
| 2.5 | 0 | 100 | 2.0 | 60 |

| Method Name: | 002_CA04 |
| --- | --- |
| Column: | XBridge C18_4.6 × 30 mm, 3.5 μm |
| Column Supplier: | Waters |

| Method Name: | 004_CA05 |
| --- | --- |
| Column: | XBridge C18_3.0 × 30 mm, 2.5 μm |
| Column Supplier: | Waters |

| Gradient/Solvent Time [min] | % Sol [H2O 0.1% NH4OH] | % Sol [Acetonitrile] | Flow [ml/min] | Temp [° C.] |
| --- | --- | --- | --- | --- |
| 0.0 | 98 | 2 | 2.5 | 60 |
| 1.5 | 0 | 100 | 2.5 | 60 |
| 1.8 | 0 | 100 | 2.5 | 60 |

| Method Name: | 004_CA05 |
| --- | --- |
| Column: | XBridge C18_3.0 × 30 mm, 2.5 μm |
| Column Supplier: | Waters |

| Gradient/Solvent Time [min] | % Sol [H2O 0.1% NH4OH] | % Sol [Acetonitrile] | Flow [ml/min] | Temp [° C.] |
| --- | --- | --- | --- | --- |
| 0.0 | 98 | 2 | 2.0 | 60 |
| 1.2 | 0 | 100 | 2.0 | 60 |
| 1.4 | 0 | 100 | 2.0 | 60 |

| Method Name: | 004_CC_ZQ4 |
| --- | --- |
| Column: | Sunfire C18_4.6 × 50 mm, 3.5 μm |
| Column Supplier: | Waters |

| Gradient/Solvent Time [min] | % Sol [H2O 0.1% TFA] | % Sol [Methanol] | Flow [ml/min] | Temp [° C.] |
| --- | --- | --- | --- | --- |
| 0.0 | 80 | 20 | 2.0 | 60 |
| 1.7 | 0 | 100 | 2.0 | 60 |
| 2.5 | 0 | 100 | 2.0 | 60 |
| 2.6 | 80 | 20 | 2.0 | 60 |

| Method Name: | 015_CC_SQD1 |
| --- | --- |
| Column: | BEH C18_2.1 × 30 mm, 1.7 μm |
| Column Supplier: | Waters |

| Gradient/Solvent Time [min] | % Sol [H2O 0.1% NH4OH] | % So [Acetonitrile] | Flow [ml/min] | Temp [° C.] |
| --- | --- | --- | --- | --- |
| 0.0 | 95.0 | 5.0 | 1.5 | 60 |
| 0.8 | 0.1 | 99.9 | 1.5 | 60 |
| 0.9 | 0.1 | 99.9 | 1.5 | 60 |

| Method Name: | X012_S01 |
| --- | --- |
| Column: | Xbridge BEH C18, 2.1 × 30 mm, 1.7 μm |
| Column Supplier: | Waters |

| Gradient/Solvent Time [min] | % Sol [H2O, 0.1% TFA] | % Sol [Acetonitrile] | Flow [ml/min] | Temp [° C.] |
| --- | --- | --- | --- | --- |
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Method Name: | 005_CA01 |
| --- | --- |
| Column: | Sunfire C18_3.0 × 30 mm, 2.5 μm |
| Column Supplier: | Waters |

| Gradient/ Solvent Time [min] | % Sol [H2O, 0.1% TFA] | % Sol [Acetonitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| Method Name: | 001_CA07 |
|---|---|
| Column: | Sunfire C18_2.1 × 50 mm, 2.5 μm |
| Column Supplier: | Waters |

| Gradient/ Solvent Time [min] | % Sol [H2O 0.1% TFA] | % Sol [Acetonitrile 0.08% TFA] | Flow [ml/min] | Temp [° C.] |
|---|---|---|---|---|
| 0.0 | 95.0 | 5.0 | 1.5 | 60.0 |
| 0.75 | 0.0 | 100.0 | 1.5 | 60.0 |
| 0.85 | 0.0 | 100.0 | 1.5 | 60.0 |

| Method Name: | 002_CA07 |
|---|---|
| Column: | XBridge BEH C18_3.0 × 30 mm, 1.7 μm |
| Column Supplier: | Waters |

| Gradient/ Solvent Time [min] | % Sol [H2O 0.1% NH4OH] | % Sol [Acetonitrile] | Flow [ml/min] | Temp [° C.] |
|---|---|---|---|---|
| 0.0 | 95.0 | 5.0 | 1.5 | 60.0 |
| 0.7 | 0.1 | 99.9 | 1.5 | 60.0 |
| 0.8 | 0.1 | 99.9 | 1.5 | 60.0 |
| 0.81 | 95.0 | 5.0 | 1.5 | 60.0 |
| 1.1 | 95.0 | 5.0 | 1.5 | 60.0 |

| Method Name: | CD00 |
|---|---|
| Column: | XBridge Shield RP C18, 50 × 2.1 mm, 5 μm |
| Column Supplier: | Waters |

| Gradient/ Solvent Time [min] | % Sol [H2O, 10 mmol $(NH_4)_2CO_3$] | % Sol [Acetonitrile] | Flow [ml/min] | Temp [° C.] |
|---|---|---|---|---|
| 0.00 | 100 | 0 | 0.6 | 50.0 |
| 0.40 | 100 | 0 | 0.6 | 50.0 |
| 3.40 | 20 | 80 | 0.6 | 50.0 |
| 3.85 | 0 | 100 | 0.6 | 50.0 |
| 3.86 | 100 | 0 | 0.6 | 50.0 |

| Method Name: | X011_S03 |
|---|---|
| Column: | Xbridge BEH C18, 2.1 × 30 mm, 1.7 μm |
| Column Supplier: | Waters |

| Gradient/ Solvent Time [min] | % Sol [H2O, 0.1% NH3] | % Sol [Acetonitrile] | Flow [ml/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | 0-30AB |
|---|---|
| Column: | Venusil XBP-C18, 50 × 2.1 mm, 5 μm |
| Column Supplier: | Bonna Agela |

| Gradient/ Solvent Time [min] | % Sol [H2O, 0.0375% TFA] | % Sol [MeCN, 0.18% TFA] | Flow [ml/min] | Temp [° C.] |
|---|---|---|---|---|
| 0.00 | 100 | 0 | 1.0 | 50 |
| 2.60 | 70 | 30 | 1.0 | 50 |
| 2.70 | 70 | 30 | 1.0 | 50 |
| 2.71 | 100 | 0 | 1.0 | 50 |
| 3.00 | 100 | 0 | 1.0 | 50 |

| Method Name: | 0-30HPLC |
|---|---|
| Column: | XBridge Shield RP C18, 50 × 2.1 mm, 5 μm |
| Column Supplier: | Waters |

| Gradient/ Solvent Time [min] | % Sol [H2O, 10 mmol $(NH_4)_2CO_3$] | % Sol [MeCN] | Flow [ml/min] | Temp [° C.] |
|---|---|---|---|---|
| 0.00 | 100 | 0 | 0.8 | 40 |
| 4.40 | 70 | 30 | 0.8 | 40 |
| 5.20 | 70 | 30 | 0.8 | 40 |
| 5.22 | 100 | 0 | 0.8 | 40 |
| 5.90 | 100 | 0 | 0.8 | 40 |

| Method Name: | 5-95AB |
|---|---|
| Column: | Chromolith Flash RP-18e, 25 × 2 mm, 1.5 μm |
| Column Supplier: | Merck Milipore |

| Gradient/ Solvent Time [min] | % Sol [H2O, 0.0375% TFA] | % Sol [MeCN, 0.18% TFA] | Flow [ml/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

Preparation 1: 6-Methyl-4-oxo-5-(3-trifluoromethyl-phenyl)-1,4-dihydro-pyridine-3-carboxylic acid 4-methanesulfonyl-benzylamide

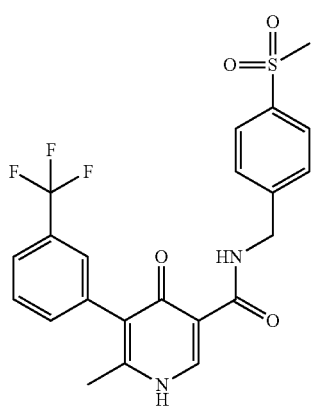 [SMILES: Cc1[nH]cc(C(=O)NCc2ccc(S(C)(=O)=O)cc2)c(=O)c1-c1cccc(C(F)(F)F)c1]

1a 5-Bromo-6-methyl-4-oxo-1,4-dihydro-pyridine-3-carboxylic acid

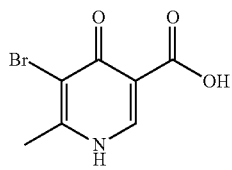

To a solution of 4-hydroxy-6-methyl-nicotinic acid (10.00 g, 65.3 mmol) in glacial acetic acid (35 mL) is added bromine (4.00 mL, 78.1 mmol). After stirring for 18 h at room temperature, additional bromine (0.5 mL) is added and the reaction mixture is stirred for an additional 24 h. The reaction mixture is evaporated under reduced pressure and the remaining residue is co-evaporated with toluene. The remaining residue is treated with a small amount of MeOH and then triturated with water. The precipitate is filtered off and dried. Yield: 13.8 g (92% of theory); ESI mass spectrum: [M+H]$^+$=232 (bromine isotope pattern); Retention time HPLC: 0.61 min (Z002_002).

1b 6-Methyl-4-oxo-5-(3-trifluoromethyl-phenyl)-1,4-dihydro-pyridine-3-carboxylic acid

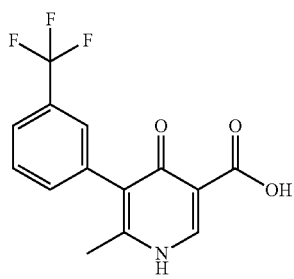 [SMILES: Cc1[nH]cc(C(=O)O)c(=O)c1-c1cccc(C(F)(F)F)c1]

To a solution of 5-bromo-6-methyl-4-oxo-1,4-dihydro-pyridine-3-carboxylic acid (preparation 1a, 12.05 g, 51.9 mmol), 3-(trifluoromethyl)phenylboronic acid (13.6 g, 71.6 mmol), 1,1'-[bis(diphenylphosphino)ferrocene]dichloropalladium(II) (3.60 g, 4.92 mmol) in acetonitrile (100 mL) is added 2 M aqueous K$_2$CO$_3$ solution (47 mL, 94 mmol). After stirring for 6 h at 75° C., the reaction mixture is filtered and the filtrate is concentrated under reduced pressure. The resulting residue is dissolved in dichloromethane and extracted several times with water. The combined aqueous layer is acidified with 4 N aqueous HCl. The formed precipitate is filtered off, washed with hexanes/ethyl acetate (4:1) and dried. Yield: 13.5 g (88% of theory); ESI mass spectrum: [M+H]$^+$=298; Retention time HPLC: 0.80 min (Z003_001).

1c 6-Methyl-4-oxo-5-(3-trifluoromethyl-phenyl)-1,4-dihydro-pyridine-3-carboxylic acid 4-methanesulfonyl-benzylamide

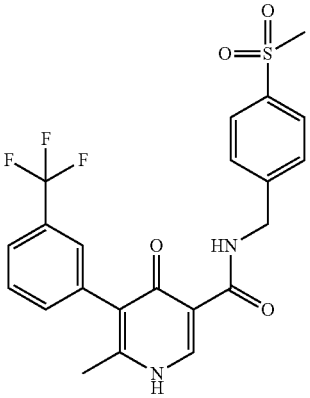 [SMILES: Cc1[nH]cc(C(=O)NCc2ccc(S(C)(=O)=O)cc2)c(=O)c1-c1cccc(C(F)(F)F)c1]

A solution of 6-methyl-4-oxo-5-(3-trifluoromethyl-phenyl)-1,4-dihydro-pyridine-3-carboxylic acid (preparation 1b, 3.00 g, 10.1 mmol), HBTU (4.00 g, 10.5 mmol) and DIPEA (5.00 mL, 29.4 mmol) in NMP (15 mL) is stirred for 30 min. Then, 4-methylsulfonylbenzylamine hydrochloride (2.46 g, 11.1 mmol) is added and the reaction mixture is stirred for 72 h at room temperature. Water is added to the reaction mixture. The formed gummy precipitate is dissolved in MeOH and purified by preparative reversed-phase HPLC (Gilson, XBridge, gradient of methanol in water, 0.3% NH$_4$OH, 60° C.). Yield: 1.50 g (32% of theory); ESI mass spectrum: [M+H]$^+$=465; Retention time HPLC: 0.89 min (Z003_001).

Preparation 2: 6-Methyl-4-oxo-5-(3-trifluoromethyl-phenyl)-1,4-dihydro-pyridine-3-carboxylic acid (5-methanesulfonyl-pyridin-2-ylmethyl)-amide

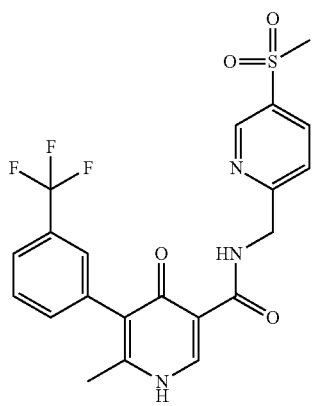 [SMILES: Cc1[nH]cc(C(=O)NCc2ccc(S(C)(=O)=O)cn2)c(=O)c1-c1cccc(C(F)(F)F)c1]

Preparation 2 is prepared following the procedure for preparation 1, substituting 4-methylsulfonylbenzylamine hydrochloride with C-(5-methanesulfonyl-pyridin-2-yl)-methylamine. ESI mass spectrum: [M+H]⁺=466; Retention time HPLC: 1.09 min (V003_003)

Preparation 3: 1-Isopropyl-6-methyl-4-oxo-5-(3-trifluoromethyl-phenyl)-1,4-dihydro-pyridine-3-carboxylic acid

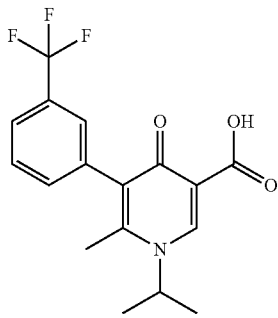 [SMILES: Cc1c(-c2cccc(C(F)(F)F)c2)c(=O)c(C(=O)O)cn1C(C)C]

3a:
3-Dimethylaminomethylene-6-methyl-pyran-2,4-dione

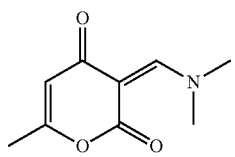

To a solution of 4-hydroxy-6-methyl-2-pyrone (11.50 g, 91.2 mmol) in toluene (30 mL) is added N,N-dimethylformamide dimethyl acetal (13.00 mL, 97.9 mmol). After stirring for 2 h at room temperature, the reaction mixture is evaporated under reduced pressure and co-evaporated with toluene several times. Yield: 18.5 g; ESI mass spectrum: [M+H]⁺= 182; Retention time HPLC: 0.72 min (Z002_007).

3b: 1-Isopropyl-6-methyl-4-oxo-1,4-dihydro-pyridine-3-carboxylic acid

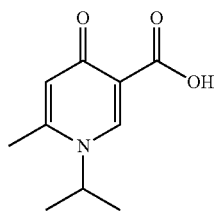

A solution of 3-dimethylaminomethylene-6-methyl-pyran-2,4-dione (preparation 3a, 10.00 g, 38.6 mmol based on 70% purity), isopropylamine (5.00 mL, 58.4 mmol) and sodium tert-butoxide (5.50 g, 57.2 mmol) in ethanol (20 mL) is heated for 18 h at 90° C. The reaction mixture is evaporated under reduced pressure, treated with water and extracted with dichloromethane. The aqueous layer is acidified with 4 N aqueous HCl and extracted with dichloromethane. The combined organic layer is washed with water, dried over Na₂SO₄ and evaporated under reduced pressure. Yield: 7.16 g; ESI mass spectrum: [M+H]⁺=196; Retention time HPLC: 0.71 min (Z002_006).

3c: 5-Bromo-1-isopropyl-6-methyl-4-oxo-1,4-dihydro-pyridine-3-carboxylic acid

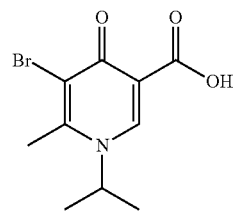

To a solution of 1-isopropyl-6-methyl-4-oxo-1,4-dihydro-pyridine-3-carboxylic acid (preparation 3b, 1.50 g, 6.92 mmol based on 90% purity) in glacial acetic acid (10 ml) is added at room temperature bromine (0.60 mL, 11.7 mmol). After stirring for 3 d at room temperature, additional bromine (1.00 mL, 19.5 mmol) is added to the reaction mixture and stirring is continued for 2 h at room temperature. The reaction mixture is diluted with water. Upon addition of dichloromethane a precipitate forms which is filtered off and dried. Yield: 2.55 g; ESI mass spectrum: [M+H]⁺=274 (bromine isotope pattern); Retention time HPLC: 0.76 min (Z002_002).

3d: 1-Isopropyl-6-methyl-4-oxo-5-(3-trifluoromethyl-phenyl)-1,4-dihydro-pyridine-3-carboxylic acid

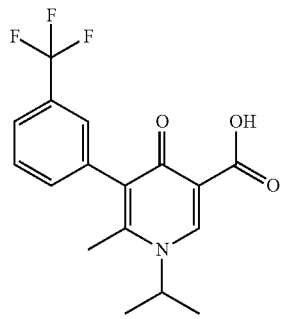

Preparation 3d is prepared following the procedure for preparation 4, substituting 3-(difluoromethyl)phenylboronic acid with 3-(trifluoromethyl)phenylboronic acid. ESI mass spectrum: [M+H]⁺=340; Retention time HPLC: 0.99 min (Z018_S04).

Preparation 4: 5-(3-Difluoromethyl-phenyl)-1-isopropyl-6-methyl-4-oxo-1,4-dihydro-pyridine-3-carboxylic acid

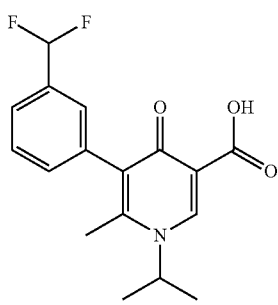 [SMILES: Cc1c(-c2cccc(C(F)F)c2)c(=O)c(C(=O)O)cn1C(C)C]

A mixture of 5-bromo-1-isopropyl-6-methyl-4-oxo-1,4-dihydro-pyridine-3-carboxylic acid (preparation 3c, 3.00 g, 8.32 mmol, based on 76% purity), 3-(difluoromethyl)-phenylboronic acid (2.30 g, 13 mmol), 1,1'-[bis(diphenylphosphino)ferrocene]-dichloropalladium(II) (690 mg, 0.94 mmol) and 2 M aqueous $K_2CO_3$ solution (10 mL, 20 mmol) in acetonitrile (20 mL) is heated for 2 h at 75° C. The reaction mixture is diluted with methanol and purified by preparative reversed phase HPLC (XBridge, gradient of acetonitrile in water, 0.3% $NH_4OH$, 30° C.). Yield: 1.46 g (55% of theory); ESI mass spectrum: $[M+H]^+=322$; Retention time HPLC: 0.92 min (Z018_S04).

Preparation 5: 5-Bromo-1-isopropyl-6-methyl-4-oxo-1,4-dihydro-pyridine-3-carboxylic acid 4-methanesulfonyl-benzylamide

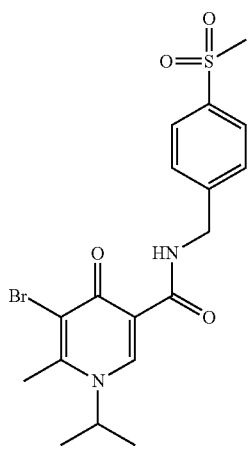 [SMILES: Cc1c(Br)c(=O)c(C(=O)NCc2ccc(S(C)(=O)=O)cc2)cn1C(C)C]

A solution of 5-bromo-1-isopropyl-6-methyl-4-oxo-1,4-dihydro-pyridine-3-carboxylic acid (preparation 3c, 0.50 g, 1.82 mmol), HBTU (0.77 g, 2.03 mmol), DIPEA (0.76 mL, 4.47 mmol) in DMF (2 mL) is stirred for 10 min. Then, 4-methylsulfonylbenzylamine hydrochloride (0.64 g, 2.89 mmol) is added and the reaction mixture is stirred for 72 h at room temperature. The reaction mixture is diluted with methanol, acidified with acetic acid and purified by preparative reversed-phase HPLC (XBridge, gradient of methanol in water, 0.1% TFA, 60° C.). Yield: 0.25 g (31% of theory); ESI mass spectrum: $[M+H]^+=441$ (bromine isotope pattern); Retention time HPLC: 1.16 min (Z002_006).

Preparation 6: 1-Cyclopropyl-6-methyl-4-oxo-5-(3-trifluoromethyl-phenyl)-1,4-dihydro-pyridine-3-carboxylic acid

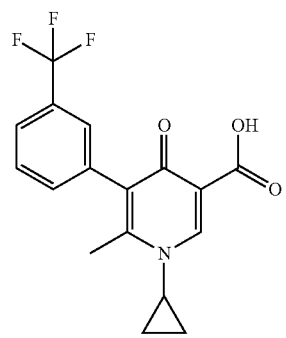 [SMILES: Cc1c(-c2cccc(C(F)(F)F)c2)c(=O)c(C(=O)O)cn1C1CC1]

6a: 1-Cyclopropyl-6-methyl-4-oxo-1,4-dihydro-pyridine-3-carboxylic acid

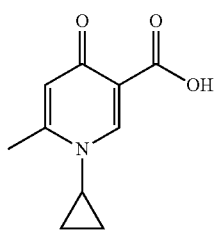

Preparation 6a is prepared following the procedure for preparation 3b, substituting isopropylamine with cyclopropylamine. ESI mass spectrum: $[M+H]^+=194$; Retention time HPLC: 0.53 min (Z002_002).

6b: 5-Bromo-1-cyclopropyl-6-methyl-4-oxo-1,4-dihydro-pyridine-3-carboxylic acid

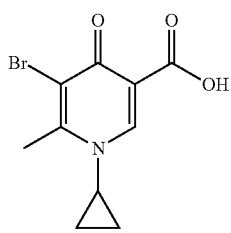

Preparation 6b is prepared following the procedure for preparation 3c, substituting preparation 3b with preparation 6a. ESI mass spectrum: [M+H]⁺=272 (bromine isotope pattern); Retention time HPLC: 0.79 min (Z002_002).

6c: 1-Cyclopropyl-6-methyl-4-oxo-5-(3-trifluoromethyl-phenyl)-1,4-dihydro-pyridine-3-carboxylic acid

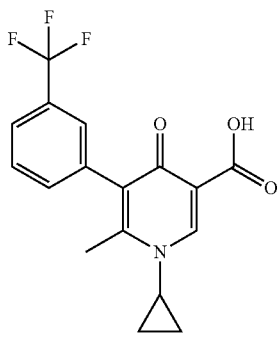 [SMILES: Cc1c(-c2cccc(C(F)(F)F)c2)c(=O)c(C(=O)O)cn1C1CC1]

Preparation 6c is prepared following the procedure for preparation 4, substituting preparation 3c with preparation 6b and 3-(difluoromethyl)phenylboronic acid with 3-(trifluoromethyl)phenylboronic acid. ESI mass spectrum: [M+H]⁺=338; Retention time HPLC: 0.63 min (Z003_001).

Preparation 7: 1-Cyclobutyl-6-methyl-4-oxo-5-(3-trifluoromethyl-phenyl)-1,4-dihydro-pyridine-3-carboxylic acid

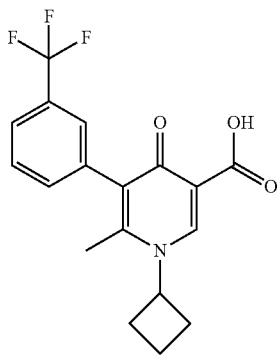 [SMILES: Cc1c(-c2cccc(C(F)(F)F)c2)c(=O)c(C(=O)O)cn1C1CCC1]

7a: 1-Cyclobutyl-6-methyl-4-oxo-1,4-dihydro-pyridine-3-carboxylic acid

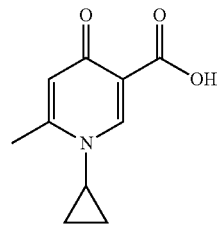

Preparation 7a is prepared following the procedure for preparation 3b, substituting isopropylamine with cyclobutylamine. ESI mass spectrum: [M+H]⁺=208; Retention time HPLC: 0.62 min (Z002_002).

7b: 5-Bromo-1-cyclobutyl-6-methyl-4-oxo-1,4-dihydro-pyridine-3-carboxylic acid

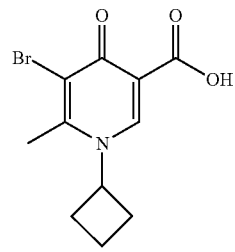 [SMILES: Cc1c(Br)c(=O)c(C(=O)O)cn1C1CCC1]

Preparation 7b is prepared following the procedure for preparation 3c, substituting preparation 3b with preparation 7a. ESI mass spectrum: [M+H]⁺=286 (bromine isotope pattern); Retention time HPLC: 0.86 min (Z002_002).

7c: 1-Cyclobutyl-6-methyl-4-oxo-5-(3-trifluoromethyl-phenyl)-1,4-dihydro-pyridine-3-carboxylic acid

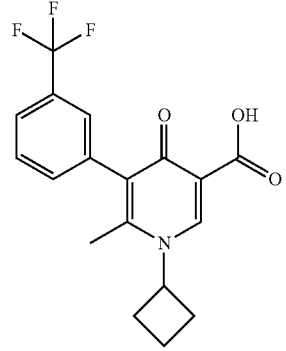

Preparation 7c is prepared following the procedure for preparation 4, substituting preparation 3c with preparation 7b and 3-(difluoromethyl)phenylboronic acid with 3-(trifluoromethyl)phenylboronic acid. ESI mass spectrum: [M+H]⁺=352; Retention time HPLC: 0.67 min (Z003_001).

Preparation 8: 1-Cyclopentyl-6-methyl-4-oxo-5-(3-trifluoromethyl-phenyl)-1,4-dihydro-pyridine-3-carboxylic acid

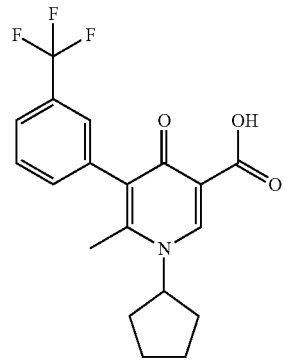 [SMILES: Cc1c(-c2cccc(C(F)(F)F)c2)c(=O)c(C(=O)O)cn1C1CCCC1]

8a: 1-Cyclopentyl-6-methyl-4-oxo-1,4-dihydro-pyridine-3-carboxylic acid

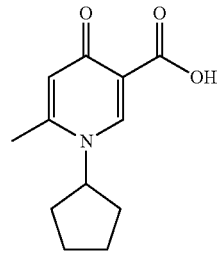 [SMILES: Cc1cc(=O)c(C(=O)O)cn1C1CCCC1]

Preparation 8a is prepared following the procedure for preparation 3b, substituting isopropylamine with cyclopentylamine. ESI mass spectrum: [M+H]$^+$=222; Retention time HPLC: 0.72 min (Z002_002).

8b: 5-Bromo-1-cyclopentyl-6-methyl-4-oxo-1,4-dihydro-pyridine-3-carboxylic acid

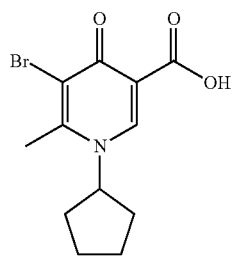 [SMILES: Cc1c(Br)c(=O)c(C(=O)O)cn1C1CCCC1]

Preparation 8b is prepared following the procedure for preparation 3c, substituting preparation 3b with preparation 8a. ESI mass spectrum: [M+H]$^+$=300 (bromine isotope pattern); Retention time HPLC: 0.90 min (Z002_002).

8c: 1-Cyclopentyl-6-methyl-4-oxo-5-(3-trifluoromethyl-phenyl)-1,4-dihydro-pyridine-3-carboxylic acid

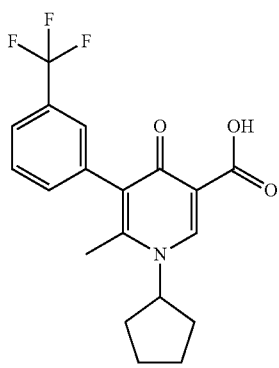 [SMILES: Cc1c(-c2cccc(C(F)(F)F)c2)c(=O)c(C(=O)O)cn1C1CCCC1]

Preparation 8c is prepared following the procedure for preparation 4, substituting preparation 3c with preparation 8b and 3-(difluoromethyl)phenylboronic acid with 3-(trifluoromethyl)phenylboronic acid. ESI mass spectrum: [M+H]$^+$= 366; Retention time HPLC: 0.71 min (Z003_001).

Preparation 9: 1-Cyclopentyl-5-(3-difluoromethyl-phenyl)-6-methyl-4-oxo-1,4-dihydro-pyridine-3-carboxylic acid

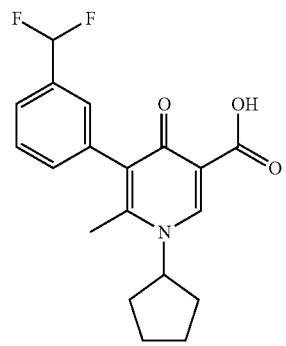 [SMILES: Cc1c(-c2cccc(C(F)F)c2)c(=O)c(C(=O)O)cn1C1CCCC1]

Preparation 9 is prepared following the procedure for preparation 4, substituting preparation 3c with preparation 8b. ESI mass spectrum: [M+H]$^+$=348; Retention time HPLC: 0.61 min (Z003_001).

Preparation 10: 5-Bromo-1-ethyl-6-methyl-4-oxo-1,4-dihydro-pyridine-3-carboxylic acid 4-methanesulfonyl-benzylamide

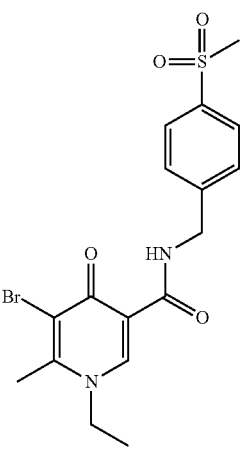 [SMILES: CCn1cc(C(=O)NCc2ccc(S(C)(=O)=O)cc2)c(=O)c(Br)c1C]

10a: 1-Ethyl-6-methyl-4-oxo-1,4-dihydro-pyridine-3-carboxylic acid

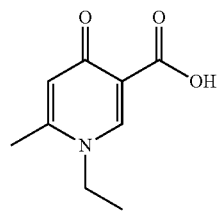

Preparation 10a is prepared following the procedure for preparation 3b, substituting isopropylamine with ethylamine. ESI mass spectrum: [M+H]$^+$=182; Retention time HPLC: 0.63 min (Z002_006).

10b: 5-Bromo-1-ethyl-6-methyl-4-oxo-1,4-dihydro-pyridine-3-carboxylic acid

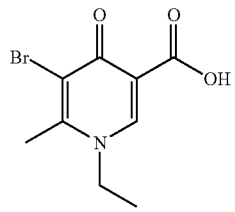

Preparation 10b is prepared following the procedure for preparation 3c, substituting preparation 3b with preparation 10a. ESI mass spectrum: $[M+H]^+=260$ (bromine isotope pattern); Retention time HPLC: 0.89 min (Z002_007).

10c: 5-Bromo-1-ethyl-6-methyl-4-oxo-1,4-dihydro-pyridine-3-carboxylic acid 4-methanesulfonyl-benzylamide

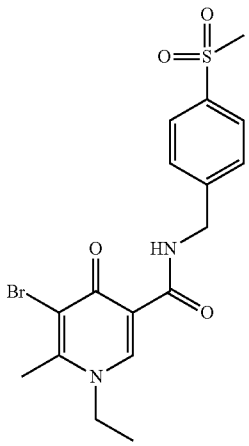 [SMILES: CCn1cc(C(=O)NCc2ccc(S(C)(=O)=O)cc2)c(=O)c(Br)c1C]

Preparation 10c is prepared following the procedure for preparation 5, substituting preparation 3c with preparation 10b. ESI mass spectrum: $[M+H]^+=427$ (bromine isotope pattern); Retention time HPLC: 0.77 min (Z003_001).

Preparation 11: (R)-5-Bromo-1-sec-butyl-6-methyl-4-oxo-1,4-dihydro-pyridine-3-carboxylic acid 4-methanesulfonyl-benzylamide

11a: (R)-1-sec-Butyl-6-methyl-4-oxo-1,4-dihydro-pyridine-3-carboxylic acid

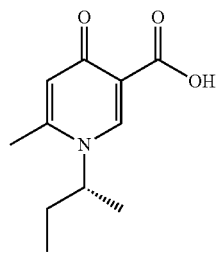

Preparation 11a is prepared following the procedure for preparation 3b, substituting isopropylamine with (R)-2-aminobutane. ESI mass spectrum: $[M+H]^+=210$; Retention time HPLC: 0.86 min (Z002_006).

11b: (R)-5-Bromo-1-sec-butyl-6-methyl-4-oxo-1,4-dihydro-pyridine-3-carboxylic acid

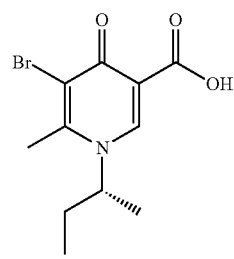

Preparation 11b is prepared following the procedure for preparation 3c, substituting preparation 3b with preparation 11a. ESI mass spectrum: $[M+H]^+=288$ (bromine isotope pattern); Retention time HPLC: 1.08 min (Z002_006).

11c: (R)-5-Bromo-1-sec-butyl-6-methyl-4-oxo-1,4-dihydro-pyridine-3-carboxylic acid 4-methanesulfonyl-benzylamide

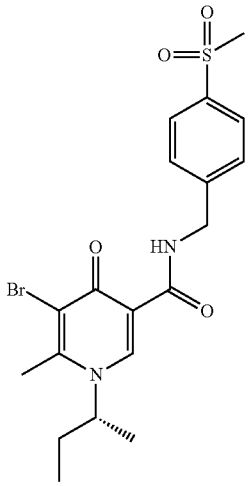 [SMILES: CC[C@@H](C)n1cc(C(=O)NCc2ccc(S(C)(=O)=O)cc2)c(=O)c(Br)c1C]

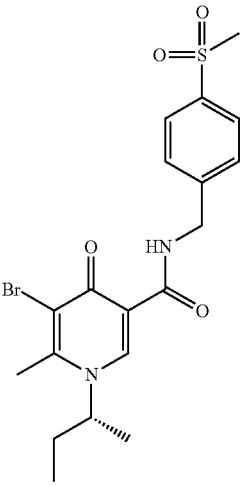

Preparation 11c is prepared following the procedure for preparation 5, substituting preparation 3c with preparation 11b. ESI mass spectrum: [M+H]⁺=455 (bromine isotope pattern); Retention time HPLC: 0.93 min (Z018_S04).

Preparation 12: (S)-5-Bromo-1-sec-butyl-6-methyl-4-oxo-1,4-dihydro-pyridine-3-carboxylic acid 4-methanesulfonyl-benzylamide

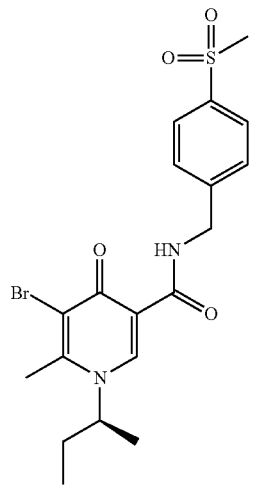 [SMILES: CC[C@H](C)n1cc(C(=O)NCc2ccc(S(C)(=O)=O)cc2)c(=O)c(Br)c1C]

12a: (S)-1-sec-Butyl-6-methyl-4-oxo-1,4-dihydro-pyridine-3-carboxylic acid

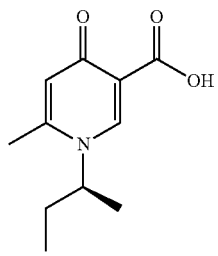

Preparation 12a is prepared following the procedure for preparation 3b, substituting isopropylamine with (S)-2-aminobutane. ESI mass spectrum: [M+H]⁺=210; Retention time HPLC: 0.86 min (Z002_006).

12b: (S)-5-Bromo-1-sec-butyl-6-methyl-4-oxo-1,4-dihydro-pyridine-3-carboxylic acid

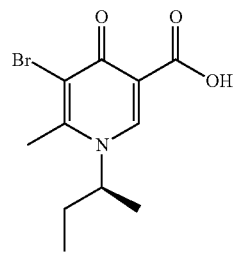 [SMILES: CC[C@H](C)n1cc(C(=O)O)c(=O)c(Br)c1C]

Preparation 12b is prepared following the procedure for preparation 3c, substituting preparation 3b with preparation 12a. ESI mass spectrum: [M+H]⁺=288 (bromine isotope pattern); Retention time HPLC: 1.08 min (Z002_006).

12c: (S)-5-Bromo-1-sec-butyl-6-methyl-4-oxo-1,4-dihydro-pyridine-3-carboxylic acid 4-methanesulfonyl-benzylamide

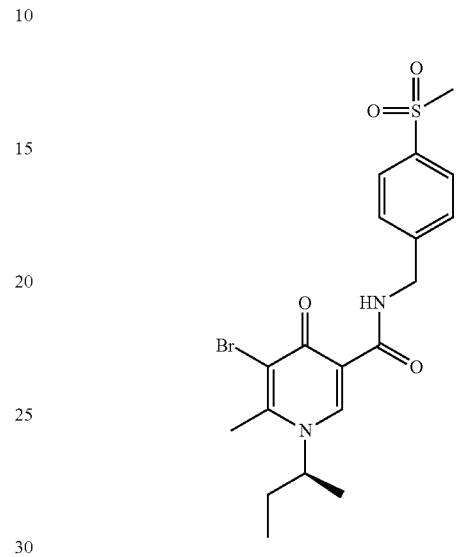

Preparation 12c is prepared following the procedure for preparation 5, substituting preparation 3c with preparation 12b. ESI mass spectrum: [M+H]⁺=455 (bromine isotope pattern); Retention time HPLC: 0.93 min (Z018_S04).

Preparation 13: 5-Iodo-1-(2-methoxy-ethyl)-6-methyl-4-oxo-1,4-dihydro-pyridine-3-carboxylic acid 4-methanesulfonyl-benzylamide

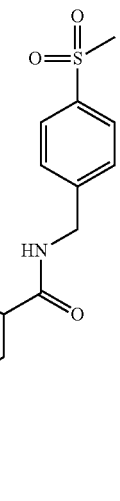

13a: 1-(2-Methoxy-ethyl)-6-methyl-4-oxo-1,4-dihydro-pyridine-3-carboxylic acid

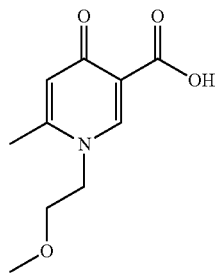

Preparation 13a is prepared following the procedure for preparation 3b, substituting isopropylamine with 2-methoxyethylamine. ESI mass spectrum: [M+H]⁺=212; Retention time HPLC: 0.65 min (Z002_005).

13b: 5-Iodo-1-(2-methoxy-ethyl)-6-methyl-4-oxo-1,4-dihydro-pyridine-3-carboxylic acid

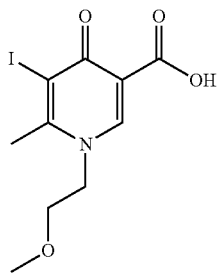 [SMILES: COCCn1cc(C(=O)O)c(=O)c(I)c1C]

A solution 1-(2-methoxy-ethyl)-6-methyl-4-oxo-1,4-dihydro-pyridine-3-carboxylic acid (150 mg, 0.71 mmol) and N-iodosuccinimide (200 mg, 0.89 mmol) in TFA (1 mL) and dichloromethane (1 mL) is stirred for 5 days at room temperature. The reaction mixture is diluted with water and extracted with dichloromethane. The organic layer is evaporate under reduced pressure. ESI mass spectrum: [M+H]⁺=338; Retention time HPLC: 0.95 min (Z002_005).

13c: 5-Iodo-1-(2-methoxy-ethyl)-6-methyl-4-oxo-1,4-dihydro-pyridine-3-carboxylic acid 4-methanesulfonyl-benzylamide

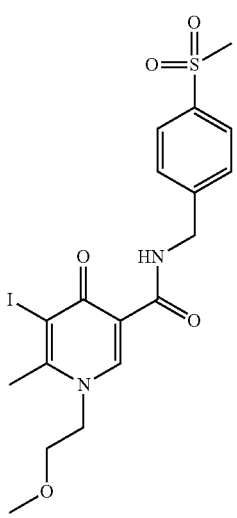 [SMILES: COCCn1cc(C(=O)NCc2ccc(S(C)(=O)=O)cc2)c(=O)c(I)c1C]

Preparation 13c is prepared following the procedure for preparation 5, substituting preparation 3c with preparation 13b and HTBU with TBTU as coupling reagent. ESI mass spectrum: [M+H]⁺=505; Retention time HPLC: 1.11 min (Z002_005).

Preparation 14: 5-Bromo-6-methyl-4-oxo-1-(tetrahydro-furan-3-yl)-1,4-dihydro-pyridine-3-carboxylic acid 4-methanesulfonyl-benzylamide

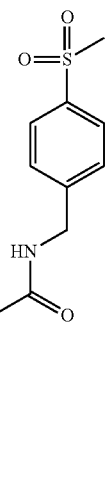

14a: 6-Methyl-4-oxo-1-(tetrahydro-furan-3-yl)-1,4-dihydro-pyridine-3-carboxylic acid

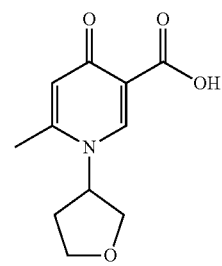 [SMILES: Cc1cc(=O)c(C(=O)O)cn1C1CCOC1]

Preparation 14a is prepared following the procedure for preparation 3b, substituting isopropylamine with tetrahydro-furan-3-ylamine. ESI mass spectrum: [M+H]⁺=224; Retention time HPLC: 0.55 min (Z002_006).

14b: 5-Bromo-6-methyl-4-oxo-1-(tetrahydro-furan-3-yl)-1,4-dihydro-pyridine-3-carboxylic acid

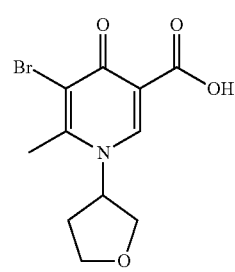 [SMILES: Cc1c(Br)c(=O)c(C(=O)O)cn1C1CCOC1]

Preparation 14b is prepared following the procedure for preparation 3c, substituting preparation 3b with preparation 14a. ESI mass spectrum: [M+H]$^+$=302 (bromine isotope pattern); Retention time HPLC: 0.71 min (Z018_S04).

14c: 5-Bromo-6-methyl-4-oxo-1-(tetrahydro-furan-3-yl)-1,4-dihydro-pyridine-3-carboxylic acid 4-methanesulfonyl-benzylamide

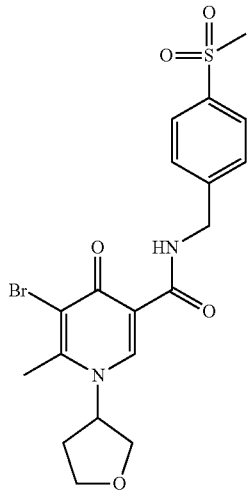 [SMILES: Cc1c(Br)c(=O)c(C(=O)NCc2ccc(S(C)(=O)=O)cc2)cn1C1CCOC1]

Preparation 14c is prepared following the procedure for preparation 5, substituting preparation 3c with preparation 14b. ESI mass spectrum: [M+H]$^+$=469 (bromine isotope pattern); Retention time HPLC: 0.82 min (Z018_S04).

Preparation 15: 5-Bromo-1-(1-ethyl-propyl)-6-methyl-4-oxo-1,4-dihydro-pyridine-3-carboxylic acid 4-methanesulfonyl-benzylamide

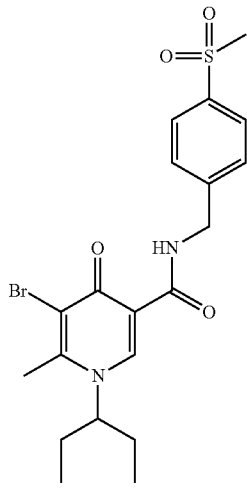 [SMILES: CCC(CC)n1cc(C(=O)NCc2ccc(S(C)(=O)=O)cc2)c(=O)c(Br)c1C]

15a: 1-(1-Ethyl-propyl)-6-methyl-4-oxo-1,4-dihydro-pyridine-3-carboxylic acid

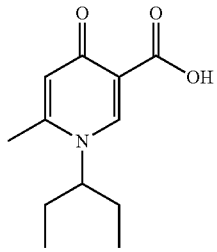 [SMILES: CCC(CC)n1cc(C(=O)O)c(=O)cc1C]

Preparation 15a is prepared following the procedure for preparation 3b, substituting isopropylamine with 3-aminopentane. ESI mass spectrum: [M+H]$^+$=224; Retention time HPLC: 0.76 min (Z018_S04).

15b: 5-Bromo-1-(1-ethyl-propyl)-6-methyl-4-oxo-1,4-dihydro-pyridine-3-carboxylic acid

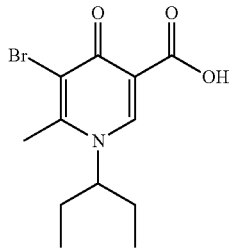

Preparation 15b is prepared following the procedure for preparation 3c, substituting preparation 3b with preparation 15a. ESI mass spectrum: [M+H]$^+$=302 (bromine isotope pattern); Retention time HPLC: 0.91 min (Z018_S04).

15c: 5-Bromo-1-(1-ethyl-propyl)-6-methyl-4-oxo-1,4-dihydro-pyridine-3-carboxylic acid 4-methanesulfonyl-benzylamide

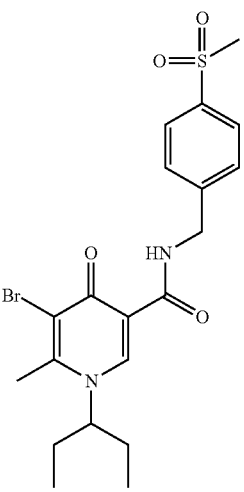

Preparation 15c is prepared following the procedure for preparation 5, substituting preparation 3c with preparation 15b. ESI mass spectrum: [M+H]⁺=469 (bromine isotope pattern); Retention time HPLC: 0.94 min (Z018_S04).

Preparation 17: 5-Bromo-1-isopropyl-6-methyl-4-oxo-1,4-dihydro-pyridine-3-carboxylic acid (5-methanesulfonyl-pyridin-2-ylmethyl)-amide

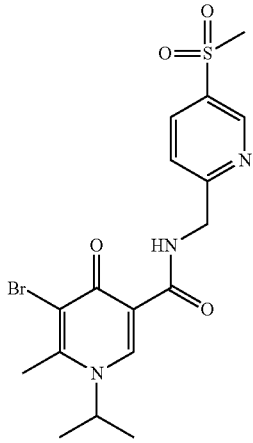 [SMILES: Cc1c(Br)c(=O)c(C(=O)NCc2ccc(S(C)(=O)=O)cn2)cn1C(C)C]

Preparation 17 is prepared following the procedure for preparation 5, substituting 4-methylsulfonylbenzylamine hydrochloride with C-(5-methanesulfonyl-pyridin-2-yl)-methylamine. ESI mass spectrum: [M+H]⁺=442 (bromine isotope pattern); Retention time HPLC: 0.66 min (Z011_S03).

Preparation 18: 5-Bromo-1-cyclobutyl-6-methyl-4-oxo-1,4-dihydro-pyridine-3-carboxylic acid (5-methanesulfonyl-pyridin-2-ylmethyl)-amide

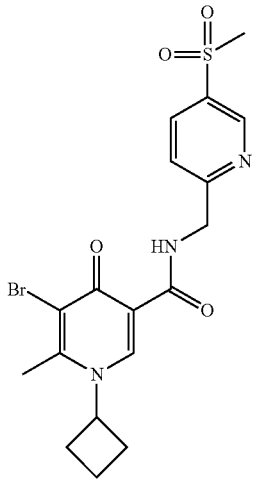 [SMILES: Cc1c(Br)c(=O)c(C(=O)NCc2ccc(S(C)(=O)=O)cn2)cn1C1CCC1]

Preparation 18 is prepared following the procedure for preparation 5, substituting preparation 3c with preparation 7b and 4-methylsulfonylbenzylamine hydrochloride with C-(5-methanesulfonyl-pyridin-2-yl)-methylamine. ESI mass spectrum: [M+H]⁺=454 (bromine isotope pattern); Retention time HPLC: 1.14 min (Z002_006).

Preparation 19: (R)-5-Bromo-1-sec-butyl-6-methyl-4-oxo-1,4-dihydro-pyridine-3-carboxylic acid (5-methanesulfonyl-pyridin-2-ylmethyl)-amide

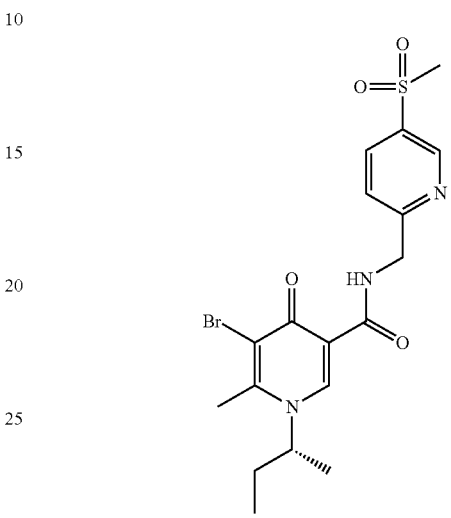

Preparation 19 is prepared following the procedure for preparation 5, substituting preparation 3c with preparation 11b and 4-methylsulfonylbenzylamine hydrochloride with C-(5-methanesulfonyl-pyridin-2-yl)-methylamine. ESI mass spectrum: [M+H]⁺=456 (bromine isotope pattern); Retention time HPLC: 0.87 min (Z018_S04).

Preparation 20: (S)-5-Bromo-1-sec-butyl-6-methyl-4-oxo-1,4-dihydro-pyridine-3-carboxylic acid (5-methanesulfonyl-pyridin-2-ylmethyl)-amide

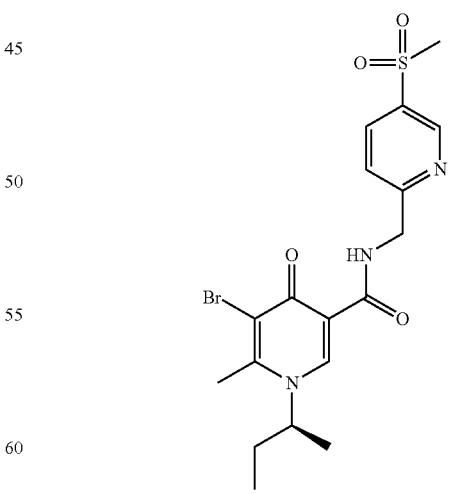

Preparation 20 is prepared following the procedure for preparation 5, substituting preparation 3c with preparation 12b and 4-methylsulfonylbenzylamine hydrochloride with C-(5-methanesulfonyl-pyridin-2-yl)-methylamine. ESI mass spectrum: [M+H]⁺=456 (bromine isotope pattern); Retention time HPLC: 0.87 min (Z018_S04).

Preparation 21: 5-Iodo-1-(2-methoxy-ethyl)-6-methyl-4-oxo-1,4-dihydro-pyridine-3-carboxylic acid (5-methanesulfonyl-pyridin-2-ylmethyl)-amide

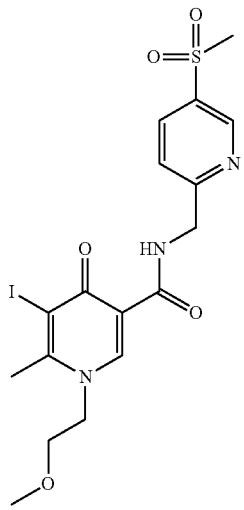 [SMILES: COCCn1cc(C(=O)NCc2ccc(S(C)(=O)=O)cn2)c(=O)c(I)c1C]

Preparation 22 is prepared following the procedure for preparation 5, substituting preparation 3c with preparation 13b, 4-methylsulfonylbenzylamine hydrochloride with C-(5-methanesulfonyl-pyridin-2-yl)-methylamine and HBTU with TBTU. ESI mass spectrum: [M+H]⁺=506; Retention time HPLC: 0.90 min (Z003_003).

Preparation 22: 5-Bromo-6-methyl-4-oxo-1-(tetrahydro-furan-3-yl)-1,4-dihydro-pyridine-3-carboxylic acid (5-methanesulfonyl-pyridin-2-ylmethyl)-amide

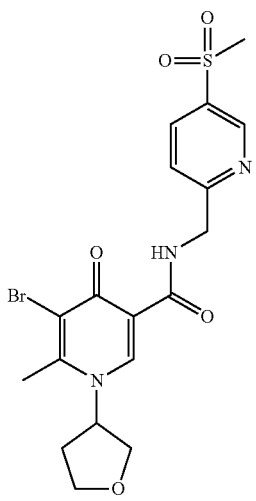 [SMILES: Cc1c(Br)c(=O)c(C(=O)NCc2ccc(S(C)(=O)=O)cn2)cn1C1CCOC1]

Preparation 22 is prepared following the procedure for preparation 5, substituting preparation 3c with preparation 14b and 4-methylsulfonylbenzylamine hydrochloride with C-(5-methanesulfonyl-pyridin-2-yl)-methylamine. ESI mass spectrum: [M+H]⁺=470 (bromine isotope pattern); Retention time HPLC: 0.77 min (Z018_S04).

Preparation 23: 5-Bromo-1-(1-ethyl-propyl)-6-methyl-4-oxo-1,4-dihydro-pyridine-3-carboxylic acid (5-methanesulfonyl-pyridin-2-ylmethyl)-amide

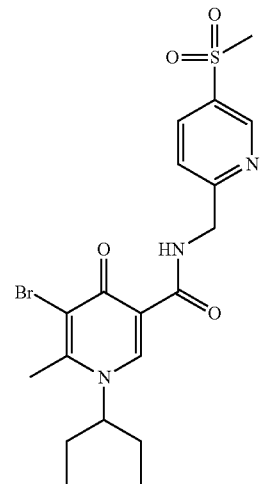 [SMILES: CCC(CC)n1cc(C(=O)NCc2ccc(S(C)(=O)=O)cn2)c(=O)c(Br)c1C]

Preparation 23 is prepared following the procedure for preparation 5, substituting preparation 3c with preparation 15b and 4-methylsulfonylbenzylamine hydrochloride with C-(5-methanesulfonyl-pyridin-2-yl)-methylamine. ESI mass spectrum: [M+H]⁺=470 (bromine isotope pattern); Retention time HPLC: 0.91 min (Z018_S04).

Preparation 24: 5-Bromo-1-cyclobutyl-6-methyl-4-oxo-1,4-dihydro-pyridine-3-carboxylic acid (5-methyl-[1,3,4]oxadiazol-2-ylmethyl)-amide

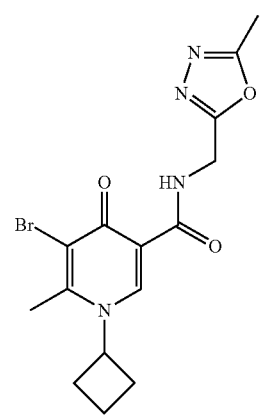 [SMILES: Cc1nnc(CNC(=O)c2cn(C3CCC3)c(C)c(Br)c2=O)o1]

Preparation 24 is prepared following the procedure for preparation 5, substituting preparation 3c with preparation 7b and 4-methylsulfonylbenzylamine hydrochloride with C-(5- methyl-[1,3,4]oxadiazol-2-yl)-methylamine. ESI mass spectrum: [M+H]$^+$=381 (bromine isotope pattern); Retention time HPLC: 0.69 min (Z003_001).

Preparation 25: (R)-5-Bromo-1-sec-butyl-6-methyl-4-oxo-1,4-dihydro-pyridine-3-carboxylic acid (5-methyl-[1,3,4]oxadiazol-2-ylmethyl)-amide

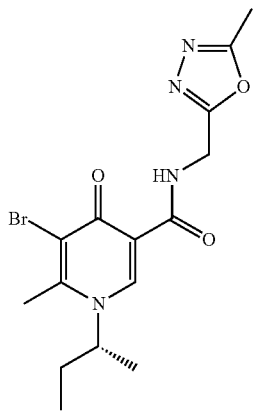 [SMILES: CC[C@@H](C)n1cc(C(=O)NCc2nnc(C)o2)c(=O)c(Br)c1C]

Preparation 25 is prepared following the procedure for preparation 5, substituting preparation 3c with preparation 11b and 4-methylsulfonylbenzylamine hydrochloride with C-(5-methyl-[1,3,4]oxadiazol-2-yl)-methylamine. ESI mass spectrum: [M+H]$^+$=383 (bromine isotope pattern); Retention time HPLC: 0.83 min (Z018_S04).

Preparation 26: (S)-5-Bromo-1-sec-butyl-6-methyl-4-oxo-1,4-dihydro-pyridine-3-carboxylic acid (5-methyl-[1,3,4]oxadiazol-2-ylmethyl)-amide

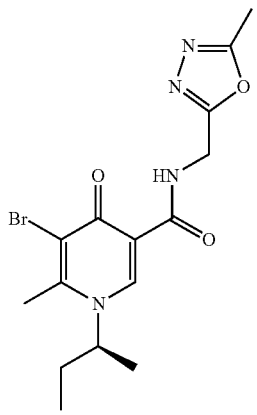 [SMILES: CC[C@H](C)n1cc(C(=O)NCc2nnc(C)o2)c(=O)c(Br)c1C]

Preparation 26 is prepared following the procedure for preparation 5, substituting preparation 3c with preparation 12b and 4-methylsulfonylbenzylamine hydrochloride with C-(5-methyl-[1,3,4]oxadiazol-2-yl)-methylamine. ESI mass spectrum: [M+H]$^+$=383 (bromine isotope pattern); Retention time HPLC: 0.83 min (Z018_S04).

Preparation 27: 5-Bromo-1-isopropyl-6-methyl-4-oxo-1,4-dihydro-pyridine-3-carboxylic acid 4-methanesulfinyl-benzylamide

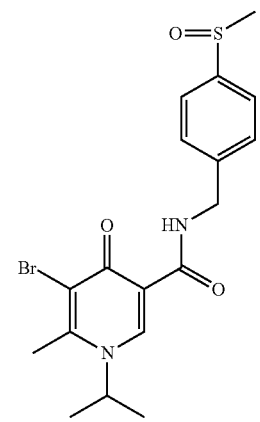 [SMILES: Cc1c(Br)c(=O)c(C(=O)NCc2ccc(S(C)=O)cc2)cn1C(C)C]

Preparation 17 is prepared following the procedure for preparation 5, substituting 4-methylsulfonylbenzylamine hydrochloride with 4-methylsulfinylbenzylamine hydrochloride (Array, A1176-1). ESI mass spectrum: [M+H]$^+$=425 (bromine isotope pattern); Retention time HPLC: 0.74 min (Z003_001).

Preparation 28: 5-Bromo-1-isopropyl-6-methyl-4-oxo-1,4-dihydro-pyridine-3-carboxylic acid 4-methanesulfonyl-3-methyl-benzylamide

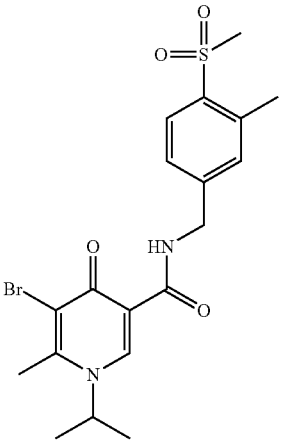 [SMILES: Cc1cc(CNC(=O)c2cn(C(C)C)c(C)c(Br)c2=O)ccc1S(C)(=O)=O]

Preparation 28 is prepared following the procedure for preparation 5, substituting 4-methylsulfonylbenzylamine hydrochloride with 4-methanesulfonyl-3-methyl-benzylamine (FCHGROUP). ESI mass spectrum: [M+H]⁺=455 (bromine isotope pattern); Retention time HPLC: 0.74 min (Z011_S03).

Preparation 29: 5-Bromo-1-isopropyl-6-methyl-4-oxo-1,4-dihydro-pyridine-3-carboxylic acid (1,1-dioxo-2,3-dihydro-1H-1λ⁶-benzo[b]thiophen-5-ylmethyl)-amide

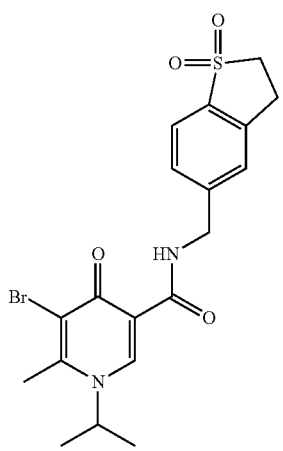 [SMILES: Cc1c(Br)c(=O)c(C(=O)NCc2ccc3c(c2)CCS3(=O)=O)cn1C(C)C]

Preparation 29 is prepared following the procedure for preparation 5, substituting 4-methylsulfonylbenzylamine hydrochloride with C-(1,1-dioxo-2,3-dihydro-1H-1λ⁶-benzo[b]thiophen-5-yl)-methylamine (FCHGROUP). ESI mass spectrum: [M+H]⁺=453 (bromine isotope pattern); Retention time HPLC: 0.71 min (Z011_S03).

Example 1.1

1-Ethyl-6-methyl-4-oxo-5-(3-trifluoromethyl-phenyl)-1,4-dihydro-pyridine-3-carboxylic acid 4-methanesulfonyl-benzylamide

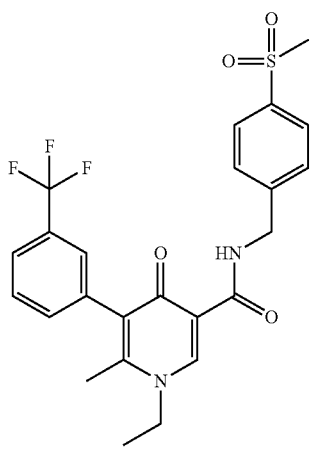 [SMILES: CCn1cc(C(=O)NCc2ccc(S(C)(=O)=O)cc2)c(=O)c(-c2cccc(C(F)(F)F)c2)c1C]

A mixture of 6-methyl-4-oxo-5-(3-trifluoromethyl-phenyl)-1,4-dihydro-pyridine-3-carboxylic acid 4-methanesulfonyl-benzylamide (preparation 1, 100 mg, 0.215 mmol), K₂CO₃ (48 mg, 0.344 mmol) and iodoethane (20 μL, 0.250 mmol) in DMF (1 mL) is stirred for 30 min at 80° C. (microwave). The reaction mixture is diluted with MeOH, filtered and purified by preparative reversed-phase HPLC (XBridge, gradient of methanol in water, 0.3% NH₄OH, 60° C.). Yield: 52 mg (49% of theory); ESI mass spectrum: [M+H]⁺=493; Retention time HPLC: 1.03 min (Z003_001).

The following Examples are prepared as described for Example 1.1, employing the corresponding alkylating agents instead of iodoethane, respectively.

| Example | Alkylating agent | Rᵃ | MS [M + H]⁺ | Retention time HPLC/Method |
|---|---|---|---|---|
| 1.2 | isopropyl-Br | isopropyl | 507 | 1.06 min Z003_001 |
| 1.3 | n-propyl-Br | n-propyl | 507 | 1.09 min Z003_001 |
| 1.4 | cyclopropylmethyl-Br | cyclopropylmethyl | 519 | 1.09 min Z003_001 |
| 1.5 | isobutyl-Br | isobutyl | 521 | 1.13 min Z003_001 |
| 1.6 | (tetrahydrofuran-3-yl)methyl-Br | (tetrahydrofuran-3-yl)methyl | 549 | 1.03 min Z003_001 |
| 1.7 | (2,2-difluorocyclopropyl)methyl-Br | (2,2-difluorocyclopropyl)methyl | 555 | 1.04 min Z003_001 |

The following examples are prepared as described for Example 1.1, substituting preparation 1 with preparation 2 and employing the corresponding alkylating agents instead of iodoethane, respectively.

mL) is stirred for 15 min at room temperature. C-(5-Methyl-[1,3,4]oxadiazol-2-yl)-methylamine (24 mg, 0.211 mmol) is added and the reaction mixture is stirred for 18 h at room temperature. The reaction mixture is purified by preparative reversed-phase HPLC (Sunfire, gradient of acetonitrile in water, 0.1% TFA, 60° C.). Yield: 6 mg (7% of theory); ESI mass spectrum: [M+H]⁺=435; Retention time HPLC: 0.86 min (Z018_S04).

The following examples are prepared as described for Example 3.1, substituting N-methylmorpholine with triethylamine and employing the appropriate amines, respectively.

| Example | Alkylating agent | $R^b$ | MS [M + H]⁺ | Retention time HPLC/ Method |
|---|---|---|---|---|
| 2.1 | (Br, ethyl) | ethyl | 494 | 1.00 min Z003_001 |
| 2.2 | (Br, propyl) | propyl | 508 | 1.05 min Z003_001 |
| 2.3 | (Br, isobutyl) | isobutyl | 522 | 1.09 min Z003_001 |
| 2.4 | (Br, tetrahydrofuranylmethyl) | tetrahydrofuranylmethyl | 550 | 0.99 min Z003_001 |

Example 3.1

1-Isopropyl-6-methyl-4-oxo-5-(3-trifluoromethyl-phenyl)-1,4-dihydro-pyridine-3-carboxylic acid (5-methyl-[1,3,4]oxadiazol-2-ylmethyl)-amide

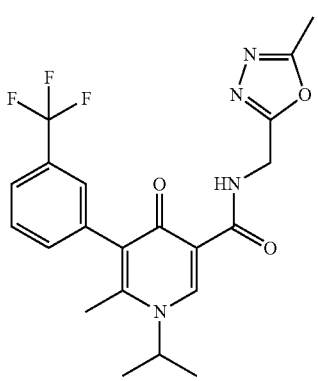 [SMILES: Cc1nnc(CNC(=O)c2cn(C(C)C)c(C)c(-c3cccc(C(F)(F)F)c3)c2=O)o1]

A solution of 1-isopropyl-6-methyl-4-oxo-5-(3-trifluoromethyl-phenyl)-1,4-dihydro-pyridine-3-carboxylic acid (preparation 3, 65 mg, 0.192 mmol), TBTU (75 mg, 0.232 mmol), N-methylmorpholine (42 µL, 0.383 mmol) in DMF (1

| Example | $R^cR^dN$— | MS [M + H]⁺ | Retention time HPLC/ Method |
|---|---|---|---|
| 3.2 | (pyridin-4-ylmethyl)amino | 430 | 0.69 min 004_CA05 |
| 3.3 | (pyridazin-3-ylmethyl)amino | 431 | 0.65 min 004_CA05 |
| 3.4 | (1-methyl-1H-pyrazol-4-ylmethyl)amino | 433 | 0.68 min 004_CA05 |
| 3.5 | (4-cyanobenzyl)amino | 454 | 0.80 min 004_CA05 |
| 3.6 | (3-methylsulfonylbenzyl)amino | 507 | 0.74 min 004_CA05 |
| 3.7 | (4-sulfamoylbenzyl)amino | 508 | 0.66 min 004_CA05 |

| Example | $R^cR^dN-$ | MS [M + H]+ | Retention time HPLC/Method |
|---|---|---|---|
| 3.8 | (4-(2-oxoimidazolidin-1-yl)benzyl)amino | 513 | 0.71 min 004_CA05 |
| 3.9 | (4-((2-oxopyrrolidin-1-yl)methyl)benzyl)amino | 526 | 0.75 min 004_CA05 |

The following examples are prepared as described for Example 3.1, substituting preparation 3 with preparation 4, substituting N-methylmorpholine with triethylamine and employing the appropriate amines, respectively.

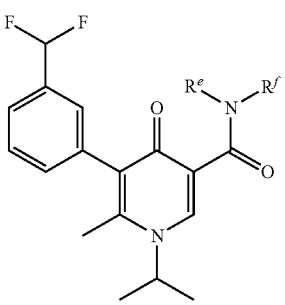

| Example | $R^eR^fN-$ | MS [M + H]+ | Retention time HPLC/Method |
|---|---|---|---|
| 4.1 | (pyridazin-3-ylmethyl)amino | 413 | 0.87 min 002_CA04 |
| 4.2 | ((1-methyl-1H-pyrazol-4-yl)methyl)amino | 415 | 0.91 min 002_CA04 |
| 4.3 | ((5-methyl-1,3,4-oxadiazol-2-yl)methyl)amino | 417 | 0.90 min 002_CA04 |
| 4.4 | ((6-oxo-1,6-dihydropyridin-2-yl)methyl)amino | 428 | 0.86 min 002_CA04 |
| 4.5 | (4-cyanobenzyl)amino | 436 | 1.10 min 002_CA04 |
| 4.6 | (imidazo[1,2-a]pyridin-2-ylmethyl)amino | 451 | 0.96 min 002_CA04 |
| 4.7 | ((1-methyl-1H-indazol-5-yl)methyl)amino | 465 | 1.05 min 002_CA04 |
| 4.8 | (4-(methylsulfinyl)benzyl)amino | 473 | 0.93 min 002_CA04 |
| 4.9 | (3-(methylsulfonyl)benzyl)amino | 489 | 1.02 min 002_CA04 |
| 4.10 | (4-sulfamoylbenzyl)amino | 490 | 0.75 min 002_CA04 |
| 4.11 | (4-((1H-imidazol-1-yl)methyl)benzyl)amino | 491 | 1.00 min 002_CA04 |
| 4.12 | (4-(2-oxoimidazolidin-1-yl)benzyl)amino | 495 | 0.97 min 002_CA04 |
| 4.13 | (4-((2-oxopyrrolidin-1-yl)methyl)benzyl)amino | 508 | 1.01 min 002_CA04 |
| 4.14 | (4-(methylsulfonyl)benzyl)amino | 489 | 0.93 min Z003_001 |

Example 5.1

1-Isopropyl-2-methyl-4-oxo-2'-trifluoromethyl-1,4-dihydro-[3,4]bipyridinyl-5-carboxylic acid 4-methanesulfonyl-benzylamide

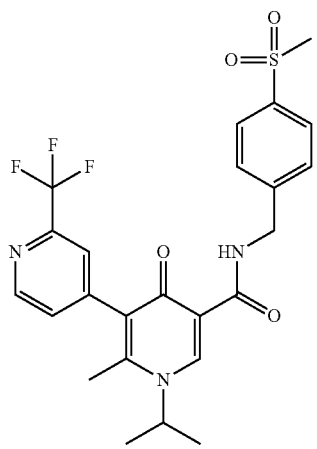 [SMILES: Cc1c(-c2ccnc(C(F)(F)F)c2)c(=O)c(C(=O)NCc2ccc(S(C)(=O)=O)cc2)cn1C(C)C]

To a solution of 5-bromo-1-isopropyl-6-methyl-4-oxo-1,4-dihydro-pyridine-3-carboxylic acid 4-methanesulfonyl-benzylamide (preparation 5, 24 mg, 0.054 mmol), 2-(trifluoromethyl)pyridine-4-boronic acid (13 mg, 0.068 mmol), 1,1'-[bis(diphenylphosphino)ferrocene]dichloropalladium(II) (5 mg, 0.007 mmol) in acetonitrile (0.15 mL) is added 2 M aqueous $K_2CO_3$ solution (0.055 mL, 0.11 mmol). After stirring for 18 h at 75° C., the reaction mixture is filtered and purified by preparative reversed-phase HPLC (XBridge, gradient of methanol in water, 0.3% $NH_4OH$, 60° C.). Yield: 4 mg (15% of theory); ESI mass spectrum: $[M+H]^+$=508; Retention time HPLC: 0.88 min (Z003_001).

The following examples are prepared as described for Example 5.1, employing the appropriate aryl- or heteroaryl-boronic acids.

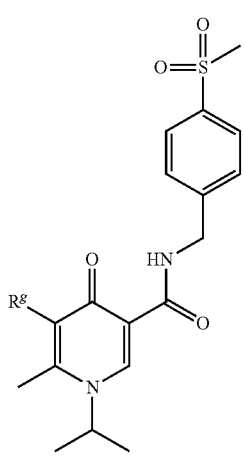

| Example | $R^g$ | MS $[M + H]^+$ | Retention time HPLC/Method |
|---|---|---|---|
| 5.2 | ![3-CF3, 4-F phenyl] | 525 | 1.01 min Z012_S04 |
| 5.3 | ![3-CF3, 5-Cl phenyl] | 541 | 0.93 min Z011_S03 |
| 5.4 | ![2-CHF2, 3-F phenyl] | 507 | 0.96 min Z012_S04 |
| 5.5 | ![5-CF3-pyridin-3-yl] | 508 | 0.90 min Z003_001 |

Example 6

1-Cyclopropyl-6-methyl-4-oxo-5-(3-trifluoromethyl-phenyl)-1,4-dihydro-pyridine-3-carboxylic acid 4-methanesulfonyl-benzylamide

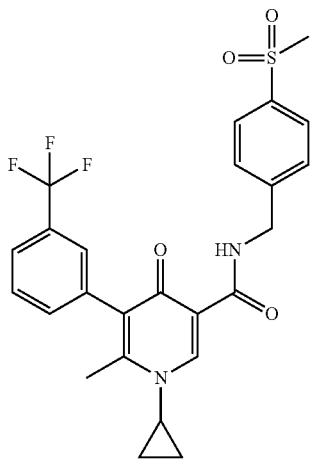 [SMILES: Cc1c(-c2cccc(C(F)(F)F)c2)c(=O)c(C(=O)NCc2ccc(S(C)(=O)=O)cc2)cn1C1CC1]

Example 6 is prepared as described for Example 3.1, substituting preparation 3 with preparation 6 and substituting C-(5-methyl-1,3,4-oxadiazol-2-yl)-methylamine with 4-methylsulfonylbenzylamine hydrochloride. ESI mass spectrum: [M+H]⁺=505; Retention time HPLC: 0.60 min (Z003_001).

Example 7

1-Cyclobutyl-6-methyl-4-oxo-5-(3-trifluoromethyl-phenyl)-1,4-dihydro-pyridine-3-carboxylic acid 4-methanesulfonyl-benzylamide

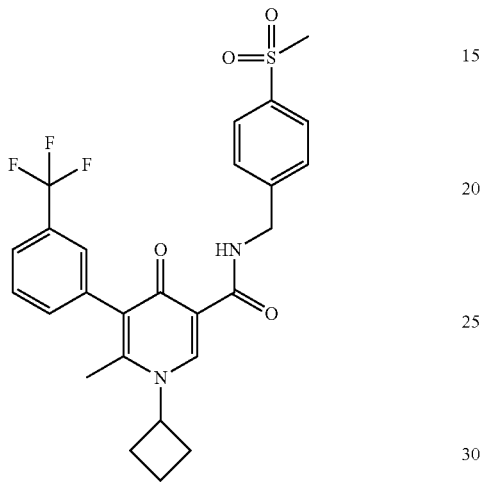

Example 7 is prepared as described for Example 9, substituting preparation 3 with preparation 7 and substituting C-(5-methyl-1,3,4-oxadiazol-2-yl)-methylamine with 4-methylsulfonylbenzylamine hydrochloride. ESI mass spectrum: [M+H]⁺=519; Retention time HPLC: 1.06 min (Z003_001).

Example 8.1

1-Cyclopentyl-6-methyl-4-oxo-5-(3-trifluoromethyl-phenyl)-1,4-dihydro-pyridine-3-carboxylic acid (5-methyl-[1,3,4]oxadiazol-2-ylmethyl)-amide

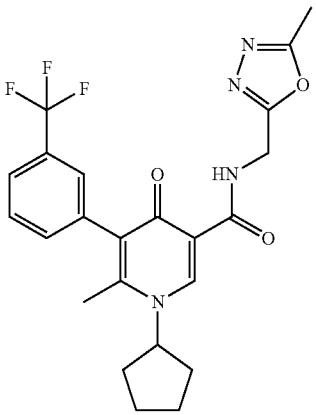 [SMILES: Cc1nnc(CNC(=O)c2cn(C3CCCC3)c(C)c(-c3cccc(C(F)(F)F)c3)c2=O)o1]

Example 8.1 is prepared following the procedure for Example 3.1, substituting preparation 3 with preparation 8. ESI mass spectrum: [M+H]⁺=461; Retention time HPLC: 1.03 min (Z003_001).

Example 8.2

1-Cyclopentyl-6-methyl-4-oxo-5-(3-trifluoromethyl-phenyl)-1,4-dihydro-pyridine-3-carboxylic acid 4-methanesulfonyl-benzylamide

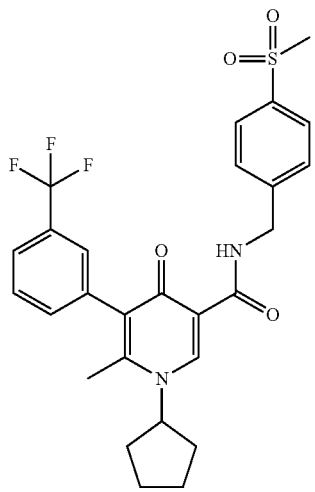 [SMILES: Cc1c(-c2cccc(C(F)(F)F)c2)c(=O)c(C(=O)NCc2ccc(S(C)(=O)=O)cc2)cn1C1CCCC1]

Example 9.2 is prepared as described for Example 3.1, substituting preparation 3 with preparation 8 and substituting C-(5-methyl-1,3,4-oxadiazol-2-yl)-methylamine with 4-methylsulfonylbenzylamine hydrochloride. ESI mass spectrum: [M+H]⁺=533; Retention time HPLC: 1.08 min (Z003_001).

Example 9.1

1-Cyclopentyl-5-(3-difluoromethyl-phenyl)-6-methyl-4-oxo-1,4-dihydro-pyridine-3-carboxylic acid (5-methyl-[1,3,4]oxadiazol-2-ylmethyl)-amide

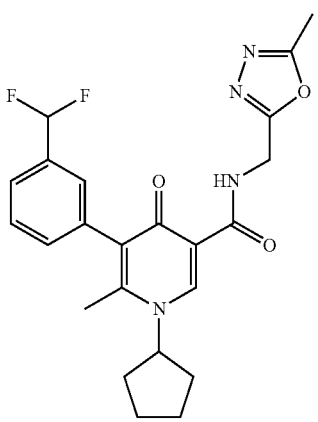 [SMILES: Cc1nnc(CNC(=O)c2cn(C3CCCC3)c(C)c(-c3cccc(C(F)F)c3)c2=O)o1]

A solution of 1-cyclopentyl-5-(3-difluoromethyl-phenyl)-6-methyl-4-oxo-1,4-dihydro-pyridine-3-carboxylic acid (preparation 9, 116 mg, 0.334 mmol), HBTU (140 mg, 0.369 mmol), DIPEA (116 μL, 0.668 mmol) in DMF (1 mL) is stirred for 15 min at room temperature. C-(5-methyl-1,3,4-oxadiazol-2-yl)-methylamine (46 mg, 0.407 mmol) is added and the reaction mixture is stirred for 72 h at room temperature. The reaction mixture is purified by preparative reversed-phase HPLC (XBridge, gradient of methanol in water, 0.3% NH$_4$OH, 60° C.). Yield: 67 mg (45% of theory); ESI mass spectrum: [M+H]$^+$=443; Retention time HPLC: 0.98 min (Z003_001).

Example 9.2

1-Cyclopentyl-5-(3-difluoromethyl-phenyl)-6-methyl-4-oxo-1,4-dihydro-pyridine-3-carboxylic acid 4-methanesulfonyl-benzylamide

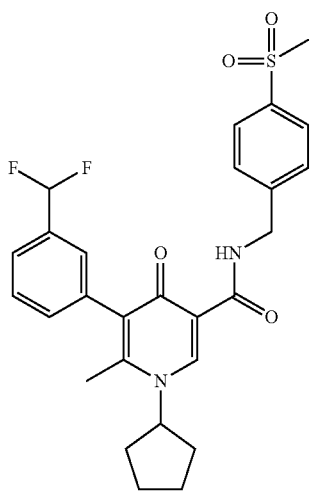 [SMILES: Cc1c(-c2cccc(C(F)F)c2)c(=O)c(C(=O)NCc2ccc(S(C)(=O)=O)cc2)cn1C1CCCC1]

Example 9.2 is prepared as described for Example 3.1, substituting preparation 3 with preparation 9 and substituting C-(5-methyl-1,3,4-oxadiazol-2-yl)-methylamine with 4-methylsulfonylbenzylamine hydrochloride. ESI mass spectrum: [M+H]$^+$=515; Retention time HPLC: 1.02 min (Z003_001).

Example 10

5-(3-Difluoromethyl-phenyl)-1-ethyl-6-methyl-4-oxo-1,4-dihydro-pyridine-3-carboxylic acid 4-methanesulfonyl-benzylamide

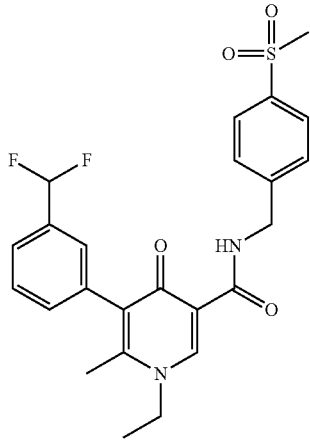 [SMILES: CCn1cc(C(=O)NCc2ccc(S(C)(=O)=O)cc2)c(=O)c(-c2cccc(C(F)F)c2)c1C]

Example 10 is prepared following the procedure for Example 24.1, substituting preparation 24 with preparation 10 and 3-(trifluoromethyl)phenylboronic acid with 3-(difluoromethyl)phenylboronic acid. ESI mass spectrum: [M+H]$^+$=475; Retention time HPLC: 0.95 min (Z003_001).

Example 11.1

(R)-1-sec-Butyl-5-(3-difluoromethyl-phenyl)-6-methyl-4-oxo-1,4-dihydro-pyridine-3-carboxylic acid 4-methanesulfonyl-benzylamide

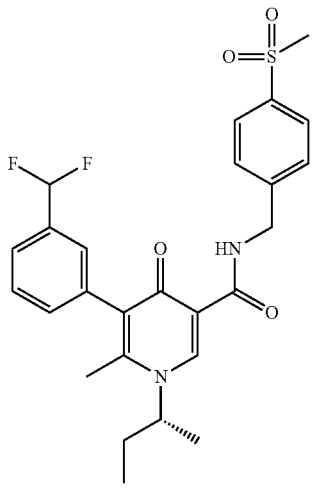 [SMILES: CC[C@@H](C)n1cc(C(=O)NCc2ccc(S(C)(=O)=O)cc2)c(=O)c(-c2cccc(C(F)F)c2)c1C]

Example 11.1 is prepared following the procedure for Example 24.1, substituting preparation 24 with preparation 11 and 3-(trifluoromethyl)phenylboronic acid with 3-(difluoromethyl)phenylboronic acid. ESI mass spectrum: [M+H]$^+$=503; Retention time HPLC: 0.96 min (Z003_001).

Example 11.2

(R)-1-sec-Butyl-2-methyl-4-oxo-2'-trifluoromethyl-1,4-dihydro-[3,4]bipyridinyl-5-carboxylic acid 4-methanesulfonyl-benzylamide

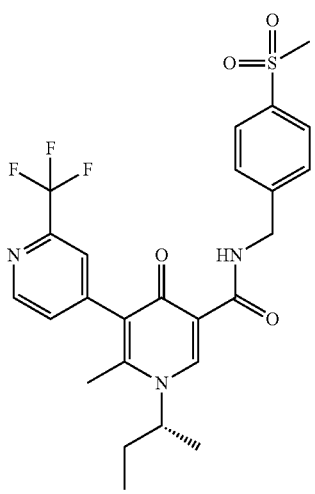 [SMILES: CC[C@@H](C)n1cc(C(=O)NCc2ccc(S(C)(=O)=O)cc2)c(=O)c(-c2ccnc(C(F)(F)F)c2)c1C]

Example 11.2 is prepared following the procedure for Example 24.1, substituting preparation 24 with preparation 11 and 3-(trifluoromethyl)phenylboronic acid with 2-(trifluoromethyl)pyridine-4-boronic acid. ESI mass spectrum: [M+H]$^+$=522; Retention time HPLC: 0.92 min (Z003_001).

Example 12.1

(S)-1-sec-Butyl-6-methyl-4-oxo-5-(3-trifluoromethyl-phenyl)-1,4-dihydro-pyridine-3-carboxylic acid 4-methanesulfonyl-benzylamide

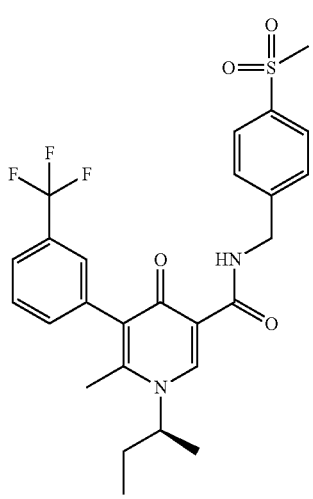 [SMILES: CC[C@H](C)n1cc(C(=O)NCc2ccc(S(C)(=O)=O)cc2)c(=O)c(-c2cccc(C(F)(F)F)c2)c1C]

Example 12.1 is prepared following the procedure for Example 24.1, substituting preparation 24 with preparation 12. ESI mass spectrum: [M+H]$^+$=521; Retention time HPLC: 1.05 min (Z003_001).

Example 12.2

(S)-1-sec-Butyl-5-(3-difluoromethyl-phenyl)-6-methyl-4-oxo-1,4-dihydro-pyridine-3-carboxylic acid 4-methanesulfonyl-benzylamide

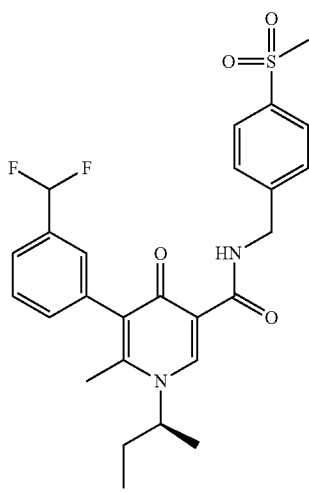 [SMILES: CC[C@H](C)n1cc(C(=O)NCc2ccc(S(C)(=O)=O)cc2)c(=O)c(-c2cccc(C(F)F)c2)c1C]

Example 12.2 is prepared following the procedure for Example 24.1, substituting preparation 24 with preparation 12 and 3-(trifluoromethyl)phenylboronic acid with 3-(difluoromethyl)phenylboronic acid. ESI mass spectrum: [M+H]$^+$=503; Retention time HPLC: 0.96 min (Z003_001).

Example 12.3

(S)-1-sec-Butyl-2-methyl-4-oxo-2'-trifluoromethyl-1,4-dihydro-[3,4]bipyridinyl-5-carboxylic acid 4-methanesulfonyl-benzylamide

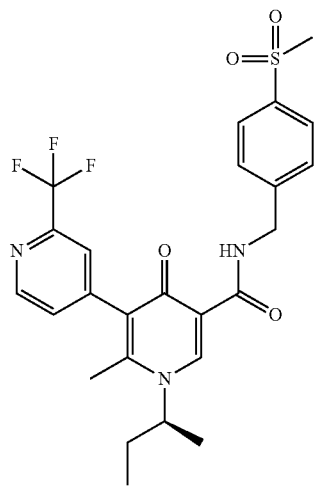 [SMILES: CC[C@H](C)n1cc(C(=O)NCc2ccc(S(C)(=O)=O)cc2)c(=O)c(-c2ccnc(C(F)(F)F)c2)c1C]

Example 12.3 is prepared following the procedure for Example 24.1, substituting preparation 24 with preparation 12 and 3-(trifluoromethyl)phenylboronic acid with 2-(trifluoromethyl)pyridine-4-boronic acid. ESI mass spectrum: [M+H]$^+$=522; Retention time HPLC: 0.92 min (Z003_001).

Example 13

1-(2-Methoxy-ethyl)-6-methyl-4-oxo-5-(3-trifluoromethyl-phenyl)-1,4-dihydro-pyridine-3-carboxylic acid 4-methanesulfonyl-benzylamide

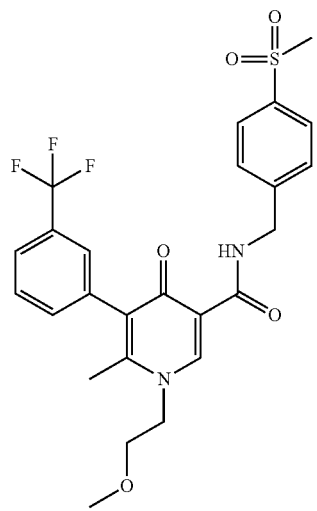

Example 13 is prepared following the procedure for Example 24.1, substituting preparation 24 with preparation 13. ESI mass spectrum: [M+H]⁺=523; Retention time HPLC: 1.18 min (Z003_003).

Example 14.1

6-Methyl-4-oxo-1-(tetrahydro-furan-3-yl)-5-(3-trifluoromethyl-phenyl)-1,4-dihydro-pyridine-3-carboxylic acid 4-methanesulfonyl-benzylamide

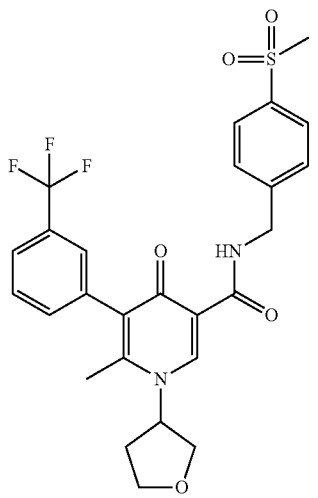 [SMILES: Cc1c(-c2cccc(C(F)(F)F)c2)c(=O)c(C(=O)NCc2ccc(S(C)(=O)=O)cc2)cn1C1CCOC1]

Example 14.1 is prepared following the procedure for Example 24.1, substituting preparation 24 with preparation 14. ESI mass spectrum: [M+H]⁺=517; Retention time HPLC: 0.77 min (Z011_S03).

Example 14.2

5-(3-Difluoromethyl-phenyl)-6-methyl-4-oxo-1-(tetrahydro-furan-3-yl)-1,4-dihydro-pyridine-3-carboxylic acid 4-methanesulfonyl-benzylamide

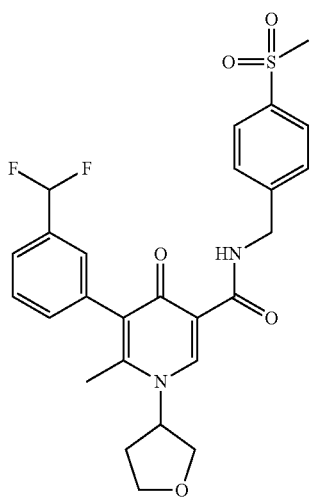 [SMILES: Cc1c(-c2cccc(C(F)F)c2)c(=O)c(C(=O)NCc2ccc(S(C)(=O)=O)cc2)cn1C1CCOC1]

Example 14.2 is prepared following the procedure for Example 24.1, substituting preparation 24 with preparation 14 and 3-(trifluoromethyl)phenylboronic acid with 3-(difluoromethyl)phenylboronic acid. ESI mass spectrum: [M+H]⁺= 535; Retention time HPLC: 0.94 min (Z003_001).

Example 15.1

1-(1-Ethyl-propyl)-6-methyl-4-oxo-5-(3-trifluoromethyl-phenyl)-1,4-dihydro-pyridine-3-carboxylic acid 4-methanesulfonyl-benzylamide

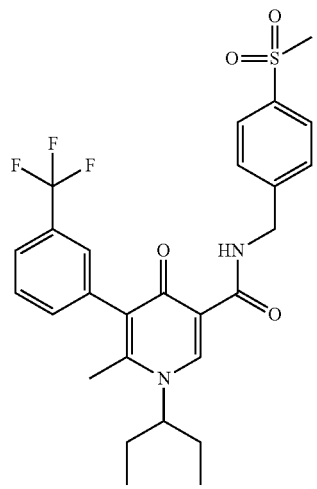 [SMILES: CCC(CC)n1cc(C(=O)NCc2ccc(S(C)(=O)=O)cc2)c(=O)c(-c2cccc(C(F)(F)F)c2)c1C]

Example 15.1 is prepared following the procedure for Example 24.1, substituting preparation 24 with preparation 15. ESI mass spectrum: [M+H]⁺=535; Retention time HPLC: 1.11 min (Z018_S04).

Example 15.2

5-(3-Difluoromethyl-phenyl)-1-(1-ethyl-propyl)-6-methyl-4-oxo-1,4-dihydro-pyridine-3-carboxylic acid 4-methanesulfonyl-benzylamide

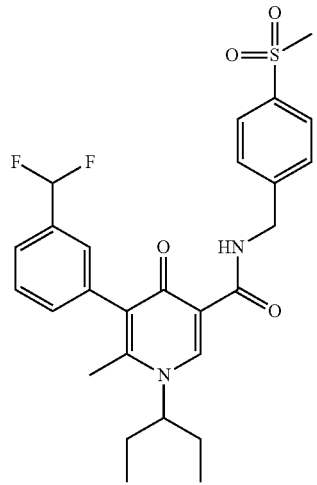 [SMILES: CCC(CC)n1cc(C(=O)NCc2ccc(S(C)(=O)=O)cc2)c(=O)c(-c2cccc(C(F)F)c2)c1C]

Example 15.2 is prepared following the procedure for Example 24.1, substituting preparation 24 with preparation 15 and 3-(trifluoromethyl)phenylboronic acid with 3-(difluoromethyl)phenylboronic acid. ESI mass spectrum: [M+H]$^+$= 517; Retention time HPLC: 1.06 min (Z018_S04).

Example 15.3

1-(1-Ethyl-propyl)-2-methyl-4-oxo-2'-trifluoromethyl-1,4-dihydro-[3,4]bipyridinyl-5-carboxylic acid 4-methanesulfonyl-benzylamide

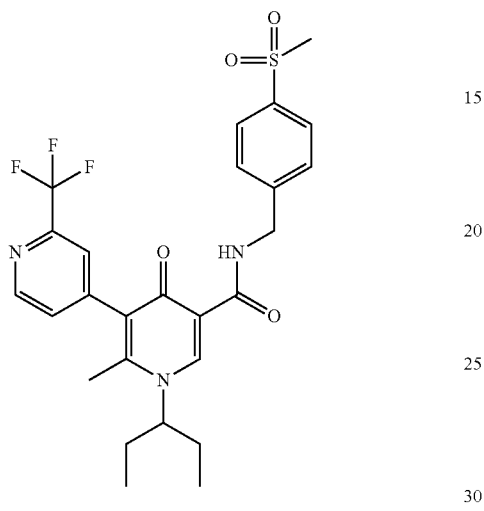

Example 15.3 is prepared following the procedure for Example 24.1, substituting preparation 24 with preparation 15 and 3-(trifluoromethyl)phenylboronic acid with 2-(trifluoromethyl)pyridine-4-boronic acid. ESI mass spectrum: [M+H]$^+$=536; Retention time HPLC: 1.02 min (Z018_S04).

Example 16

1-(2-Methoxy-ethyl)-6-methyl-4-oxo-5-(3-trifluoromethyl-phenyl)-1,4-dihydro-pyridine-3-carboxylic acid (5-methanesulfonyl-1-oxy-pyridin-2-ylmethyl)-amide

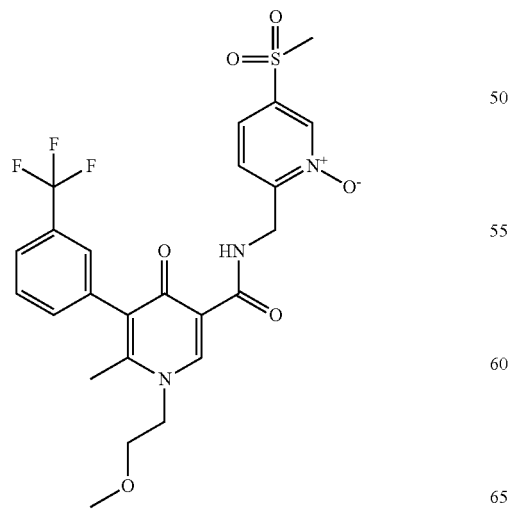

To a solution of 1-(2-methoxy-ethyl)-6-methyl-4-oxo-5-(3-trifluoromethyl-phenyl)-1,4-dihydro-pyridine-3-carboxylic acid (5-methanesulfonyl-pyridin-2-ylmethyl)-amide (Example 21, 40 mg, 0.076 mmol) in dichloromethane (1 mL) is added 3-chloroperoxybenzoic acid (MCPBA, 88 mg, 0.357 mmol). After stirring for 1 day at room temperature, the reaction mixture is purified by preparative reversed-phase HPLC (XBridge, gradient of methanol in water, 0.1% NH$_4$OH, 60° C.). Yield: 17 mg (37% of theory); ESI mass spectrum: [M+H]$^+$=540; Retention time HPLC: 1.08 min (Z003_003).

Example 17.1

1-Isopropyl-6-methyl-4-oxo-5-(3-trifluoromethyl-phenyl)-1,4-dihydro-pyridine-3-carboxylic acid (5-methanesulfonyl-pyridin-2-ylmethyl)-amide

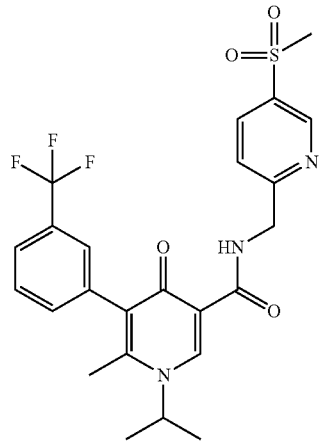 [SMILES: Cc1c(-c2cccc(C(F)(F)F)c2)c(=O)c(C(=O)NCc2ccc(S(C)(=O)=O)cn2)cn1C(C)C]

Example 17.1 is prepared following the procedure for Example 24.1, substituting preparation 24 with preparation 17. ESI mass spectrum: [M+H]$^+$=508; Retention time HPLC: 1.03 min (Z003_001).

Example 17.2

5-(3-Difluoromethyl-phenyl)-1-isopropyl-6-methyl-4-oxo-1,4-dihydro-pyridine-3-carboxylic acid (5-methanesulfonyl-pyridin-2-ylmethyl)-amide

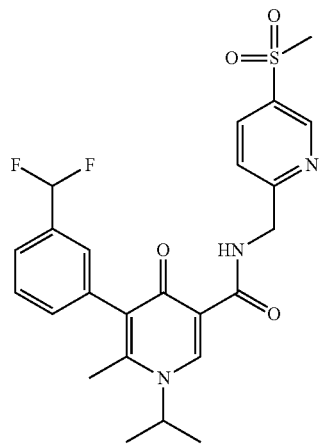 [SMILES: Cc1c(-c2cccc(C(F)F)c2)c(=O)c(C(=O)NCc2ccc(S(C)(=O)=O)cn2)cn1C(C)C]

Example 17.2 is prepared following the procedure for Example 24.1, substituting preparation 24 with preparation 17 and 3-(trifluoromethyl)phenylboronic acid with 3-(difluoromethyl)phenylboronic acid. ESI mass spectrum: [M+H]$^+$=490; Retention time HPLC: 0.86 min (Z003_001).

Example 17.3

1-Isopropyl-2-methyl-4-oxo-2'-trifluoromethyl-1,4-dihydro-[3,4]bipyridinyl-5-carboxylic acid (5-methanesulfonyl-pyridin-2-ylmethyl)-amide

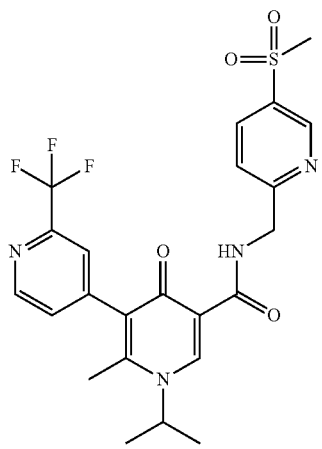

Example 17.3 is prepared following the procedure for Example 24.1, substituting preparation 24 with preparation 17 and 3-(trifluoromethyl)phenylboronic acid with 2-(trifluoromethyl)pyridine-4-boronic acid. ESI mass spectrum: [M+H]$^+$=509; Retention time HPLC: 0.81 min (Z003_001).

Example 18.1

1-Cyclobutyl-6-methyl-4-oxo-5-(3-trifluoromethyl-phenyl)-1,4-dihydro-pyridine-3-carboxylic acid (5-methanesulfonyl-pyridin-2-ylmethyl)-amide

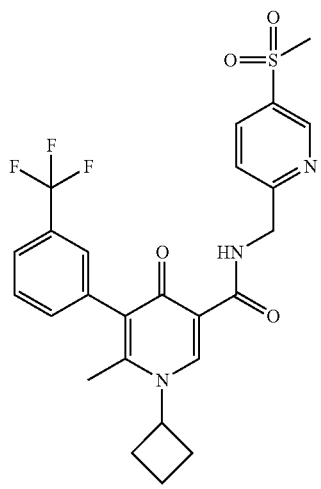

Example 18.1 is prepared following the procedure for Example 24.1, substituting preparation 24 with preparation 18. ESI mass spectrum: [M+H]$^+$=520; Retention time HPLC: 1.06 min (Z003_001).

Example 18.2

1-Cyclobutyl-5-(3-difluoromethyl-phenyl)-6-methyl-4-oxo-1,4-dihydro-pyridine-3-carboxylic acid (5-methanesulfonyl-pyridin-2-ylmethyl)-amide

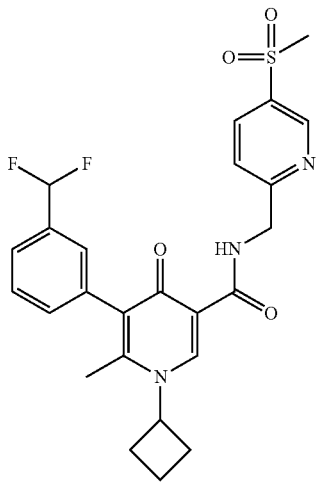 [SMILES: Cc1c(-c2cccc(C(F)F)c2)c(=O)c(C(=O)NCc2ccc(S(C)(=O)=O)cn2)cn1C1CCC1]

Example 18.2 is prepared following the procedure for Example 24.1, substituting preparation 24 with preparation 18 and 3-(trifluoromethyl)phenylboronic acid with 3-(difluoromethyl)phenylboronic acid. ESI mass spectrum: [M+H]$^+$=502; Retention time HPLC: 0.91 min (Z003_001).

Example 19.1

(R)-1-sec-Butyl-6-methyl-4-oxo-5-(3-trifluoromethyl-phenyl)-1,4-dihydro-pyridine-3-carboxylic acid (5-methanesulfonyl-pyridin-2-ylmethyl)-amide

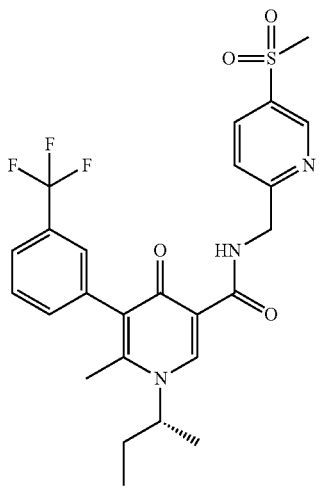 [SMILES: CC[C@@H](C)n1cc(C(=O)NCc2ccc(S(C)(=O)=O)cn2)c(=O)c(-c2cccc(C(F)(F)F)c2)c1C]

Example 19.1 is prepared following the procedure for Example 24.1, substituting preparation 24 with preparation 19. ESI mass spectrum: [M+H]⁺=522; Retention time HPLC: 1.01 min (Z003_001).

Example 19.2

(R)-1-sec-Butyl-5-(3-difluoromethyl-phenyl)-6-methyl-4-oxo-1,4-dihydro-pyridine-3-carboxylic acid (5-methanesulfonyl-pyridin-2-ylmethyl)-amide

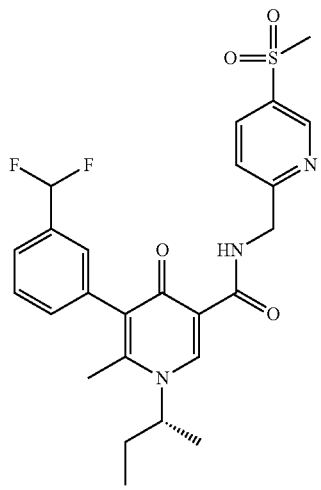 [SMILES: CC[C@@H](C)n1cc(C(=O)NCc2ccc(S(C)(=O)=O)cn2)c(=O)c(-c2cccc(C(F)F)c2)c1C]

Example 19.2 is prepared following the procedure for Example 24.1, substituting preparation 24 with preparation 19 and 3-(trifluoromethyl)phenylboronic acid with 3-(difluoromethyl)phenylboronic acid. ESI mass spectrum: [M+H]⁺=504; Retention time HPLC: 0.91 min (Z003_001).

Example 19.3

(R)-1-sec-Butyl-2-methyl-4-oxo-2'-trifluoromethyl-1,4-dihydro-[3,4']bipyridinyl-5-carboxylic acid (5-methanesulfonyl-pyridin-2-ylmethyl)-amide

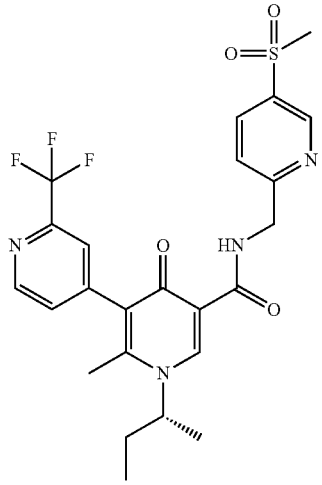 [SMILES: CC[C@@H](C)n1cc(C(=O)NCc2ccc(S(C)(=O)=O)cn2)c(=O)c(-c2ccnc(C(F)(F)F)c2)c1C]

Example 19.3 is prepared following the procedure for Example 24.1, substituting preparation 24 with preparation 19 and 3-(trifluoromethyl)phenylboronic acid with 2-(trifluoromethyl)pyridine-4-boronic acid. ESI mass spectrum: [M+H]⁺=523; Retention time HPLC: 0.87 min (Z003_001).

Example 20.1

(S)-1-sec-Butyl-6-methyl-4-oxo-5-(3-trifluoromethyl-phenyl)-1,4-dihydro-pyridine-3-carboxylic acid (5-methanesulfonyl-pyridin-2-ylmethyl)-amide

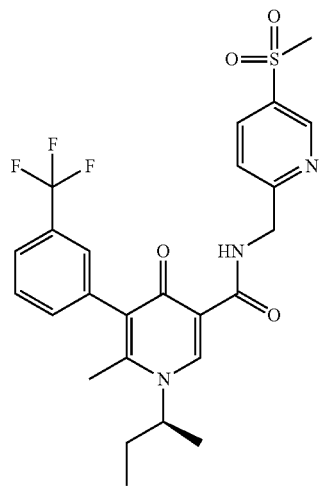 [SMILES: CC[C@H](C)n1cc(C(=O)NCc2ccc(S(C)(=O)=O)cn2)c(=O)c(-c2cccc(C(F)(F)F)c2)c1C]

Example 20.1 is prepared following the procedure for Example 24.1, substituting preparation 24 with preparation 20. ESI mass spectrum: [M+H]⁺=522; Retention time HPLC: 1.01 min (Z003_001).

Example 20.2

(S)-1-sec-Butyl-5-(3-difluoromethyl-phenyl)-6-methyl-4-oxo-1,4-dihydro-pyridine-3-carboxylic acid (5-methanesulfonyl-pyridin-2-ylmethyl)-amide

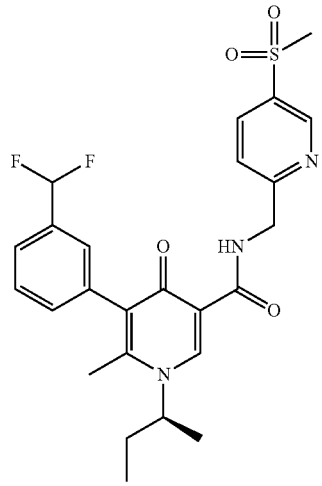 [SMILES: CC[C@H](C)n1cc(C(=O)NCc2ccc(S(C)(=O)=O)cn2)c(=O)c(-c2cccc(C(F)F)c2)c1C]

Example 20.2 is prepared following the procedure for Example 24.1, substituting preparation 24 with preparation 20 and 3-(trifluoromethyl)phenylboronic acid with 3-(difluoromethyl)phenylboronic acid. ESI mass spectrum: [M+H]$^+$=504; Retention time HPLC: 0.92 min (Z002_006).

Example 20.3

(S)-1-sec-Butyl-2-methyl-4-oxo-2'-trifluoromethyl-1,4-dihydro-[3,4]bipyridinyl-5-carboxylic acid (5-methanesulfonyl-pyridin-2-ylmethyl)-amide

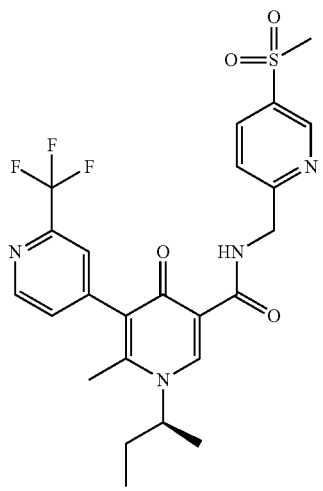 [SMILES: CC[C@H](C)n1cc(C(=O)NCc2ccc(S(C)(=O)=O)cn2)c(=O)c(-c2ccnc(C(F)(F)F)c2)c1C]

Example 20.3 is prepared following the procedure for Example 24.1, substituting preparation 24 with preparation 20 and 3-(trifluoromethyl)phenylboronic acid with 2-(trifluoromethyl)pyridine-4-boronic acid. ESI mass spectrum: [M+H]$^+$=523; Retention time HPLC: 0.87 min (Z003_001).

Example 21

1-(2-Methoxy-ethyl)-6-methyl-4-oxo-5-(3-trifluoromethyl-phenyl)-1,4-dihydro-pyridine-3-carboxylic acid (5-methanesulfonyl-pyridin-2-ylmethyl)-amide

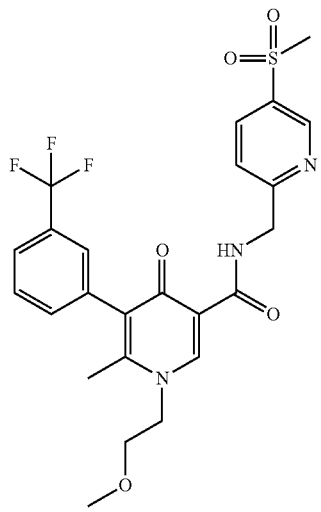 [SMILES: COCCn1cc(C(=O)NCc2ccc(S(C)(=O)=O)cn2)c(=O)c(-c2cccc(C(F)(F)F)c2)c1C]

Example 21 is prepared following the procedure for Example 24.1, substituting preparation 24 with preparation 21. ESI mass spectrum: [M+H]$^+$=524; Retention time HPLC: 1.30 min (Z002_005).

Example 22

6-Methyl-4-oxo-1-(tetrahydro-furan-3-yl)-5-(3-trifluoromethyl-phenyl)-1,4-dihydro-pyridine-3-carboxylic acid (5-methanesulfonyl-pyridin-2-ylmethyl)-amide

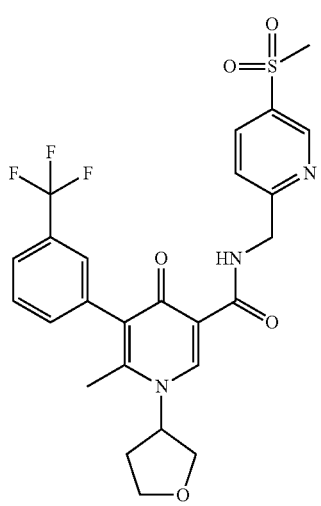 [SMILES: Cc1c(-c2cccc(C(F)(F)F)c2)c(=O)c(C(=O)NCc2ccc(S(C)(=O)=O)cn2)cn1C1CCOC1]

Example 22 is prepared following the procedure for Example 24.1, substituting preparation 24 with preparation 22. ESI mass spectrum: [M+H]$^+$=518; Retention time HPLC: 0.74 min (Z011_S03).

Example 23.1

1-(1-Ethyl-propyl)-6-methyl-4-oxo-5-(3-trifluoromethyl-phenyl)-1,4-dihydro-pyridine-3-carboxylic acid (5-methanesulfonyl-pyridin-2-ylmethyl)-amide

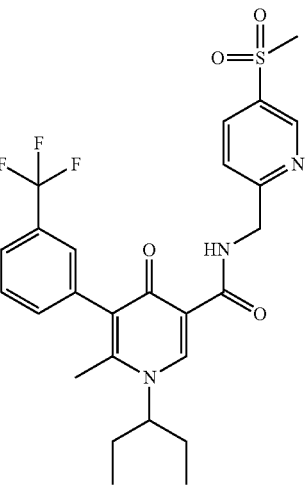

Example 23.1 is prepared following the procedure for Example 24.1, substituting preparation 24 with preparation 23. ESI mass spectrum: [M+H]$^+$=536; Retention time HPLC: 1.00 min (Z018_S04).

Example 23.2

5-(3-Difluoromethyl-phenyl)-1-(1-ethyl-propyl)-6-methyl-4-oxo-1,4-dihydro-pyridine-3-carboxylic acid (5-methanesulfonyl-pyridin-2-ylmethyl)-amide

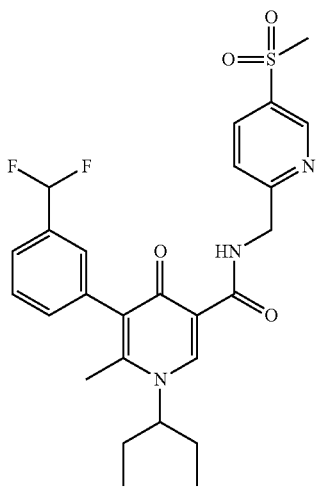 [SMILES: CCC(CC)n1cc(C(=O)NCc2ccc(S(C)(=O)=O)cn2)c(=O)c(-c2cccc(C(F)F)c2)c1C]

Example 23.2 is prepared following the procedure for Example 24.1, substituting preparation 24 with preparation 23 and 3-(trifluoromethyl)phenylboronic acid with 3-(difluoromethyl)phenylboronic acid. ESI mass spectrum: [M+H]$^+$=518; Retention time HPLC: 1.01 min (Z018_S04).

Example 23.3

1-(1-Ethyl-propyl)-2-methyl-4-oxo-2'-trifluoromethyl-1,4-dihydro-[3,4]bipyridinyl-5-carboxylic acid (5-methanesulfonyl-pyridin-2-ylmethyl)-amide

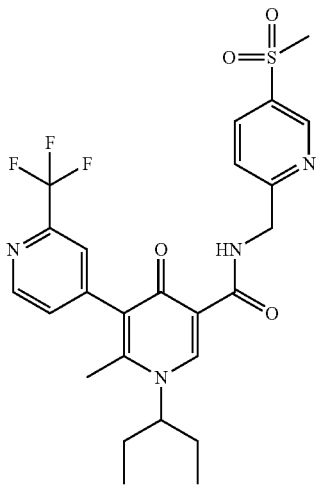 [SMILES: CCC(CC)n1cc(C(=O)NCc2ccc(S(C)(=O)=O)cn2)c(=O)c(-c2ccnc(C(F)(F)F)c2)c1C]

Example 23.3 is prepared following the procedure for Example 24.1, substituting preparation 24 with preparation 23 and 3-(trifluoromethyl)phenylboronic acid with 2-(trifluoromethyl)pyridine-4-boronic acid. ESI mass spectrum: [M+H]$^+$=537; Retention time HPLC: 0.98 min (Z018_S04).

Example 24.1

1-Cyclobutyl-6-methyl-4-oxo-5-(3-trifluoromethyl-phenyl)-1,4-dihydro-pyridine-3-carboxylic acid (5-methyl-[1,3,4]oxadiazol-2-ylmethyl)-amide

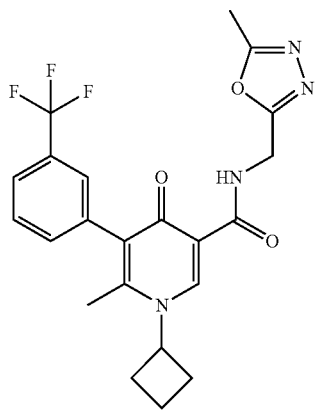 [SMILES: Cc1nnc(CNC(=O)c2cn(C3CCC3)c(C)c(-c3cccc(C(F)(F)F)c3)c2=O)o1]

To a solution of 5-bromo-1-cyclobutyl-6-methyl-4-oxo-1,4-dihydro-pyridine-3-carboxylic acid (5-methyl-[1,3,4]oxadiazol-2-ylmethyl)-amide (preparation 24, 44 mg, 0.115 mmol), 3-(trifluoromethyl)phenyl-boronic acid (26 mg, 0.137 mmol), 1,1'-[bis(diphenylphosphino)ferrocene]dichloropalladium(II) (13 mg, 0.018 mmol) in acetonitrile (0.5 mL) is added 2 M aqueous K$_2$CO$_3$ solution (0.10 mL, 0.20 mmol). After stirring for 18 h at 75° C., the reaction mixture is filtered and purified by preparative reversed-phase HPLC (XBridge, gradient of methanol in water, 0.3% NH$_4$OH, 60° C.). Yield: 40 mg (78% of theory); ESI mass spectrum: [M+H]$^+$=447; Retention time HPLC: 1.09 min (Z003_001).

Example 24.2

1-Cyclobutyl-5-(3-difluoromethyl-phenyl)-6-methyl-4-oxo-1,4-dihydro-pyridine-3-carboxylic acid (5-methyl-[1,3,4]oxadiazol-2-ylmethyl)-amide

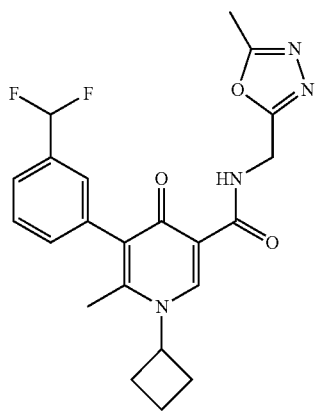 [SMILES: Cc1nnc(CNC(=O)c2cn(C3CCC3)c(C)c(-c3cccc(C(F)F)c3)c2=O)o1]

Example 24.2 is prepared following the procedure for Example 24.1, substituting 3-(trifluoromethyl)phenylboronic acid with 3-(difluoromethyl)phenylboronic acid. ESI mass spectrum: [M+H]⁺=429; Retention time HPLC: 0.89 min (Z003_001).

Example 25.1

(R)-1-sec-Butyl-6-methyl-4-oxo-5-(3-trifluoromethyl-phenyl)-1,4-dihydro-pyridine-3-carboxylic acid (5-methyl-[1,3,4]oxadiazol-2-ylmethyl)-amide

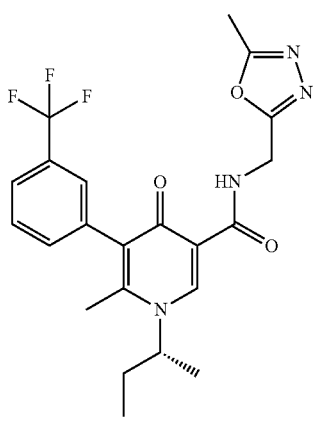 [SMILES: CC[C@@H](C)n1cc(C(=O)NCc2nnc(C)o2)c(=O)c(-c2cccc(C(F)(F)F)c2)c1C]

Example 25.1 is prepared following the procedure for Example 24.1, substituting preparation 24 with preparation 25. ESI mass spectrum: [M+H]⁺=449; Retention time HPLC: 1.03 min (Z003_001).

Example 25.2

(R)-1-sec-Butyl-5-(3-difluoromethyl-phenyl)-6-methyl-4-oxo-1,4-dihydro-pyridine-3-carboxylic acid (5-methyl-[1,3,4]oxadiazol-2-ylmethyl)-amide

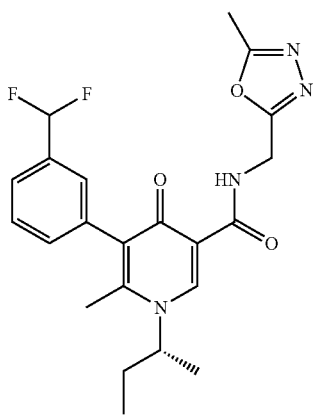 [SMILES: CC[C@@H](C)n1cc(C(=O)NCc2nnc(C)o2)c(=O)c(-c2cccc(C(F)F)c2)c1C]

Example 25.2 is prepared following the procedure for Example 24.1, substituting preparation 24 with preparation 25 and 3-(trifluoromethyl)phenylboronic acid with 3-(difluo-romethyl)phenylboronic acid. ESI mass spectrum: [M+H]⁺=431; Retention time HPLC: 0.90 min (Z003_001).

Example 26

(S)-1-sec-Butyl-5-(3-difluoromethyl-phenyl)-6-methyl-4-oxo-1,4-dihydro-pyridine-3-carboxylic acid (5-methyl-[1,3,4]oxadiazol-2-ylmethyl)-amide

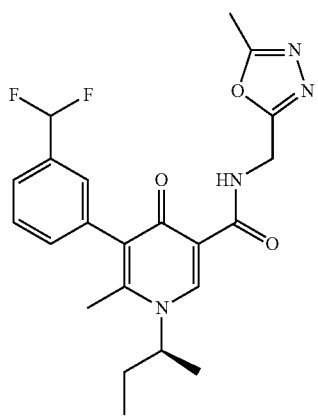 [SMILES: CC[C@H](C)n1cc(C(=O)NCc2nnc(C)o2)c(=O)c(-c2cccc(C(F)F)c2)c1C]

Example 26 is prepared following the procedure for Example 24.1, substituting preparation 24 with preparation 26 and 3-(trifluoromethyl)phenylboronic acid with 3-(difluoromethyl)phenylboronic acid. ESI mass spectrum: [M+H]⁺=431; Retention time HPLC: 0.90 min (Z003_001).

Example 27.1

1-Isopropyl-6-methyl-4-oxo-5-(3-trifluoromethyl-phenyl)-1,4-dihydro-pyridine-3-carboxylic acid 4-methanesulfinyl-benzylamide

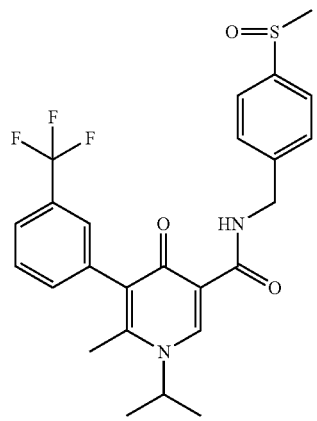 [SMILES: Cc1c(-c2cccc(C(F)(F)F)c2)c(=O)c(C(=O)NCc2ccc(S(C)=O)cc2)cn1C(C)C]

Example 27.1 is prepared following the procedure for Example 24.1, substituting preparation 24 with preparation 27. ESI mass spectrum: [M+H]$^+$=491; Retention time HPLC: 1.41 min (Z002_006).

Example 27.2

1-Isopropyl-2-methyl-4-oxo-2'-trifluoromethyl-1,4-dihydro-[3,4']bipyridinyl-5-carboxylic acid 4-methanesulfinyl-benzylamide

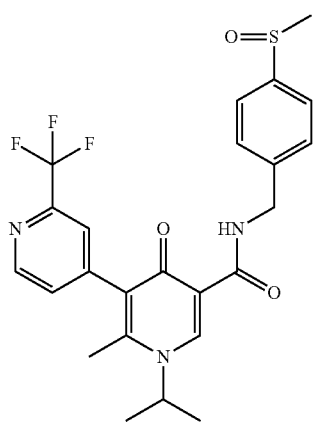 [SMILES: Cc1c(-c2ccnc(C(F)(F)F)c2)c(=O)c(C(=O)NCc2ccc(S(C)=O)cc2)cn1C(C)C]

Example 27.2 is prepared following the procedure for Example 24.1, substituting preparation 24 with preparation 27 and 3-(trifluoromethyl)phenylboronic acid with 2-(trifluoromethyl)pyridine-4-boronic acid. ESI mass spectrum: [M+H]$^+$=492; Retention time HPLC: 1.28 min (Z002_006).

Example 28.1

1-Isopropyl-6-methyl-4-oxo-5-(3-trifluoromethylphenyl)-1,4-dihydro-pyridine-3-carboxylic acid 4-methanesulfonyl-3-methyl-benzylamide

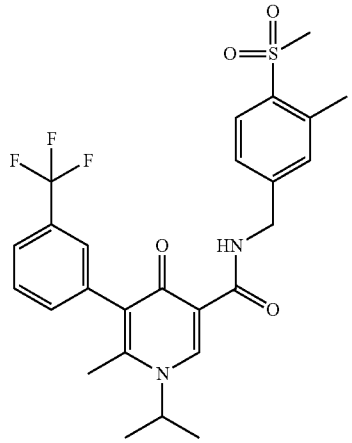 [SMILES: Cc1cc(CNC(=O)c2cn(C(C)C)c(C)c(-c3cccc(C(F)(F)F)c3)c2=O)ccc1S(C)(=O)=O]

Example 28.1 is prepared following the procedure for Example 24.1, substituting preparation 24 with preparation 28. ESI mass spectrum: [M+H]$^+$=521; Retention time HPLC: 0.90 min (Z011_S03).

Example 28.2

5-(3-Difluoromethyl-phenyl)-1-isopropyl-6-methyl-4-oxo-1,4-dihydro-pyridine-3-carboxylic acid 4-methanesulfonyl-3-methyl-benzylamide

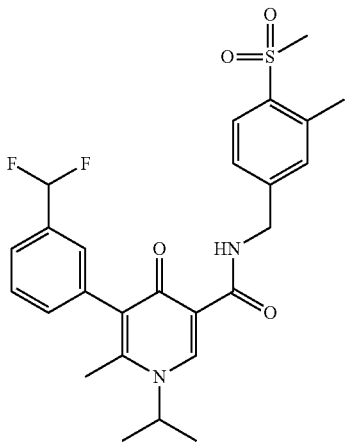

Example 28.2 is prepared following the procedure for Example 24.1, substituting preparation 24 with preparation 28 and 3-(trifluoromethyl)phenylboronic acid with 3-(difluoromethyl)phenylboronic acid. ESI mass spectrum: [M+H]$^+$=503; Retention time HPLC: 0.84 min (Z011_S03).

Example 28.3

1-Isopropyl-2-methyl-4-oxo-2'-trifluoromethyl-1,4-dihydro-[3,4]bipyridinyl-5-carboxylic acid 4-methanesulfonyl-3-methyl-benzylamide

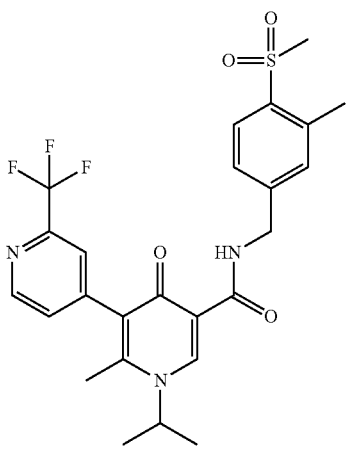

Example 28.3 is prepared following the procedure for Example 24.1, substituting preparation 24 with preparation 28 and 3-(trifluoromethyl)phenylboronic acid with 2-(trifluoromethyl)pyridine-4-boronic acid. ESI mass spectrum: [M+H]⁺=522; Retention time HPLC: 0.81 min (Z011_S03).

Example 29.1

1-Isopropyl-6-methyl-4-oxo-5-(3-trifluoromethyl-phenyl)-1,4-dihydro-pyridine-3-carboxylic acid (1,1-dioxo-2,3-dihydro-1H-1λ⁶-benzo[b]thiophen-5-ylmethyl)-amide

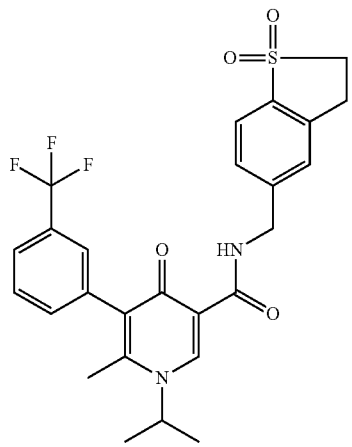 [SMILES: Cc1c(-c2cccc(C(F)(F)F)c2)c(=O)c(C(=O)NCc2ccc3c(c2)CCS3(=O)=O)cn1C(C)C]

Example 29.1 is prepared following the procedure for Example 24.1, substituting preparation 24 with preparation 29. ESI mass spectrum: [M+H]⁺=519; Retention time HPLC: 0.87 min (Z011_S03).

Example 29.2

5-(3-Difluoromethyl-phenyl)-1-isopropyl-6-methyl-4-oxo-1,4-dihydro-pyridine-3-carboxylic acid (1,1-dioxo-2,3-dihydro-1H-1λ⁶-benzo[b]thiophen-5-ylmethyl)-amide

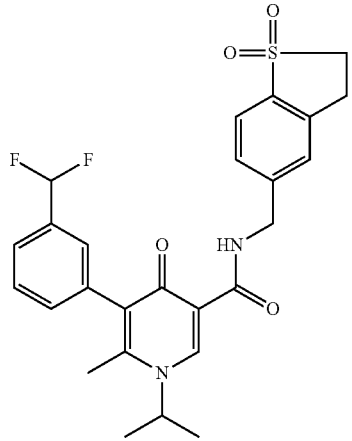 [SMILES: Cc1c(-c2cccc(C(F)F)c2)c(=O)c(C(=O)NCc2ccc3c(c2)CCS3(=O)=O)cn1C(C)C]

Example 29.2 is prepared following the procedure for Example 24.1, substituting preparation 24 with preparation 29 and 3-(trifluoromethyl)phenylboronic acid with 3-(difluoromethyl)phenylboronic acid. ESI mass spectrum: [M+H]⁺=501; Retention time HPLC: 0.81 min (Z011_S03).

Example 29.3

1-Isopropyl-2-methyl-4-oxo-2'-trifluoromethyl-1,4-dihydro-[3,4]bipyridinyl-5-carboxylic acid (1,1-dioxo-2,3-dihydro-1H-1λ⁶-benzo[b]thiophen-5-ylmethyl)-amide

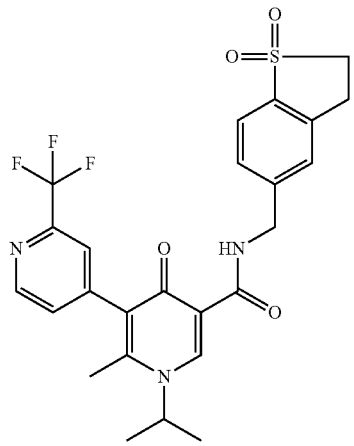 [SMILES: Cc1c(-c2ccnc(C(F)(F)F)c2)c(=O)c(C(=O)NCc2ccc3c(c2)CCS3(=O)=O)cn1C(C)C]

Example 29.3 is prepared following the procedure for Example 24.1, substituting preparation 24 with preparation 29 and 3-(trifluoromethyl)phenylboronic acid with 2-(trifluoromethyl)pyridine-4-boronic acid. ESI mass spectrum: [M+H]⁺=520; Retention time HPLC: 0.79 min (Z011_S03).

Example 30.1

1-Isopropyl-6-methyl-4-oxo-5-(3-trifluoromethyl-phenyl)-1,4-dihydro-pyridine-3-carboxylic acid 4-ethanesulfonyl-benzylamide

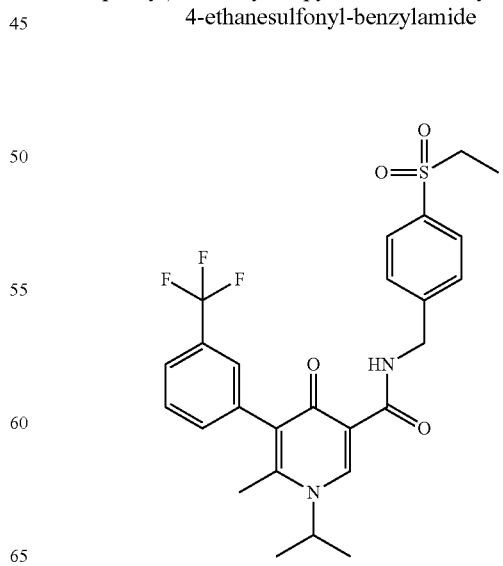

Example 30.2

6-Ethyl-1-isopropyl-4-oxo-5-(3-trifluoromethyl-phenyl)-1,4-dihydro-pyridine-3-carboxylic acid 4-ethanesulfonyl-benzylamide

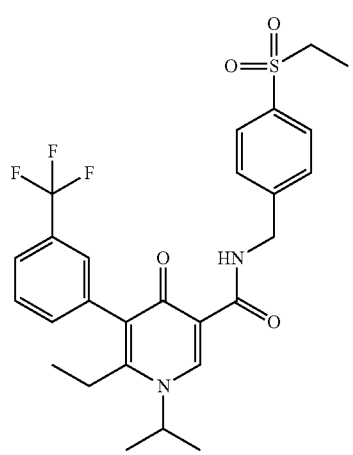 [SMILES: CCc1c(-c2cccc(C(F)(F)F)c2)c(=O)c(C(=O)NCc2ccc(S(=O)(=O)CC)cc2)cn1C(C)C]

To a solution of 1-isopropyl-6-methyl-4-oxo-5-(3-trifluoromethyl-phenyl)-1,4-dihydro-pyridine-3-carboxylic acid 4-methanesulfonyl-benzylamide (Example 1.2, 120 mg, 0.237 mmol) in THF (5 mL) is added at −65° C. n-butyl lithium (0.37 mL of 1.6 M solution in hexanes, 0.592 mmol). After stirring for 1 h at −65° C., iodomethane (22 μL, 0.355 mmol) is added and the reaction mixture is stirred for 2 h at −65° C. After stirring overnight at room temperature, the reaction mixture is quenched with water and extracted several times with ethyl acetate. The combined organic layer is dried over $Na_2SO_4$, evaporated under reduced pressure and the purified by preparative reversed-phase HPLC (XBridge, gradient of acetonitrile in water, 0.1% TFA, 60° C.) to yield 10 mg of Example 30.1; ESI mass spectrum: [M+H]$^+$=521; Retention time HPLC: 1.03 min (Z012_S04); 6 mg of Example 30.2; ESI mass spectrum: [M+H]$^+$=535; Retention time HPLC: 1.06 min (Z012_S04).

Example 27.1A and Example 27.1B

Enantiomers of Example 27.1

147 mg of racemic example 27.1 are separated by chiral HPLC (Daicel IB, 250 mm×20 mm, 10% MeOH+0.2% diethylamine in supercritical $CO_2$, 40° C.).

Early eluting enantiomer (Example 27.1A): Retention time chiral HPLC=7.36 min (Daicel Chiralpak®ODH, 4.6 mm×250 mm 5 μm, 4 ml/min, 10 min, 15% MeOH+0.2% diethylamine in supercritical $CO_2$, 40° C., 150 bar back pressure); ESI mass spectrum: [M+H]$^+$=491. Yield: 33 mg Late eluting enantiomer (Example 27.1B): Retention time chiral HPLC=7.92 min (Daicel Chiralpak®ODH, 4.6 mm×250 mm 5 μm, 4 ml/min, 10 min, 15% MeOH+0.2% diethylamine in supercritical $CO_2$, 40° C., 150 bar back pressure); ESI mass spectrum: [M+H]$^+$=491. Yield: 32 mg

Example 31

1-Isopropyl-6-methyl-4-oxo-5-(3-trifluoromethyl-phenyl)-1,4-dihydro-pyridine-3-carboxylic acid 4-cyclopropanesulfonyl-benzylamide

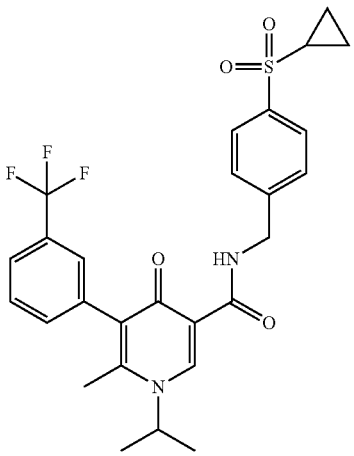 [SMILES: Cc1c(-c2cccc(C(F)(F)F)c2)c(=O)c(C(=O)NCc2ccc(S(=O)(=O)C3CC3)cc2)cn1C(C)C]

31a: 4-Cyclopropylsulfanyl-benzamide

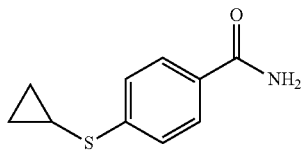 [SMILES: NC(=O)c1ccc(SC2CC2)cc1]

Thionylchloride (342 μL, 4.7 mmol) is added to a solution of 4-cyclopropylsulfanyl-benzoic acid (prepared as described in WO07003960, 190 mg, 0.98 mmol) in dichloro-methane (1.9 mL). The mixture is heated at reflux for 30 min and concentrated under reduced pressure. The residue is treated with toluene, and all volatiles are evaporated. The residue is dissolved in chloroform (1.9 mL) and treated with concentrated aqueous ammonia (770 μL, 9.8 mmol). The mixture is stirred at room temperature for 1 h and then extracted with water. The organic layer is dried over $Na_2SO_4$ and concentrated under reduced pressure. Yield: 137 mg (72% of theory); ESI mass spectrum: [M+H]$^+$=194; Retention time HPLC: 0.45 min (X011_S03).

31b: 4-Cyclopropylsulfanyl-benzylamine

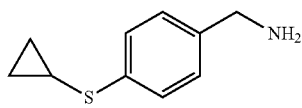 [SMILES: NCc1ccc(SC2CC2)cc1]

A solution of 4-cyclopropylsulfanyl-benzamide (preparation 31a, 137 mg, 0.71 mmol) in dry tetrahydrofuran (1.0 mL) is added at 0° C. to a solution of lithium aluminium hydride in tetrahydrofuran (1 M, 2.1 mL, 2.1 mmol). The mixture is stirred at 0° C. for 1 h and heated at reflux for 1 h. The mixture is cooled at room temperature and stirred for 1.5 h. Water is added, and the mixture is extracted twice with dichloromethane. The combined organic layers are dried over $Na_2SO_4$ and concentrated under reduced pressure. Yield: 75 mg (60% of theory); ESI mass spectrum: $[M+H]^+=180$; Retention time HPLC: 0.51 min (X011_S03).

31c 1-Isopropyl-6-methyl-4-oxo-5-(3-trifluoromethyl-phenyl)-1,4-dihydro-pyridine-3-carboxylic acid 4-cyclopropylsulfanyl-benzylamide

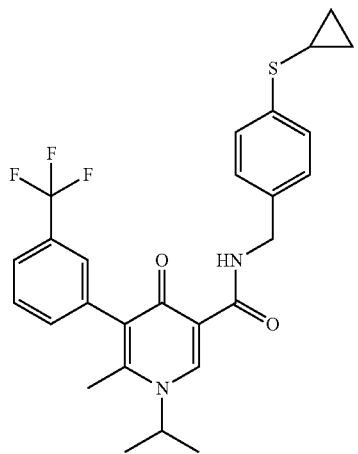 [SMILES: Cc1c(-c2cccc(C(F)(F)F)c2)c(=O)c(C(=O)NCc2ccc(SC3CC3)cc2)cn1C(C)C]

Preparation 31c is prepared as described for Example 3.1, substituting N-methylmorpholine with triethylamine and substituting C-(5-methyl-[1,3,4]oxadiazol-2-yl)-methylamine with 4-cyclopropanesulfonyl-benzylamine (preparation 31b). ESI mass spectrum: $[M+H]^+=501$; Retention time HPLC: 0.77 min (X012_S01).

Example 31

1-Isopropyl-6-methyl-4-oxo-5-(3-trifluoromethyl-phenyl)-1,4-dihydro-pyridine-3-carboxylic acid 4-cyclopropanesulfonyl-benzylamide

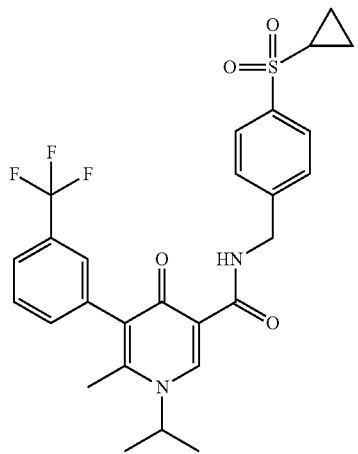 [SMILES: Cc1c(-c2cccc(C(F)(F)F)c2)c(=O)c(C(=O)NCc2ccc(S(=O)(=O)C3CC3)cc2)cn1C(C)C]

3-Chloroperoxybenzoic acid (45 mg, 77%, 0.201 mmol) is added to a solution of preparation 31c (50 mg, 0.100 mmol) in dichloromethane (1 mL). The reaction mixture is stirred for 1 h at room temperature. The reaction mixture is quenched with aqueous sodium thiosulfate solution and extracted with dichloromethane. After drying of the organic phase, the volatiles are removed under reduced pressure and the remaining residue is purified by preparative reversed-phase HPLC (Sunfire, gradient of acetonitrile in water, 0.1% TFA, 60° C.). Yield: 31 mg (59% of theory); ESI mass spectrum: $[M+H]^+=533$; Retention time HPLC: 0.89 min (005_CA01).

Example 32

1-Isopropyl-6-methyl-4-oxo-5-(3-trifluoromethyl-phenyl)-1,4-dihydro-pyridine-3-carboxylic acid 3-fluoro-4-methanesulfonyl-benzylamide

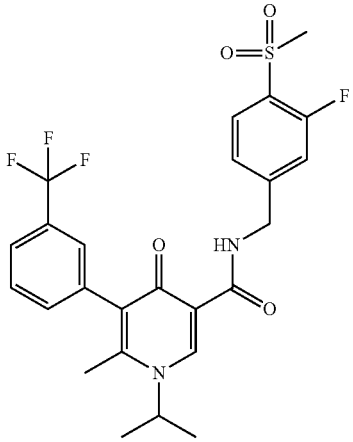 [SMILES: Cc1c(-c2cccc(C(F)(F)F)c2)c(=O)c(C(=O)NCc2ccc(S(C)(=O)=O)c(F)c2)cn1C(C)C]

32a: 2-(3-Fluoro-4-methylsulfanyl-benzyl)-isoindole-1,3-dione

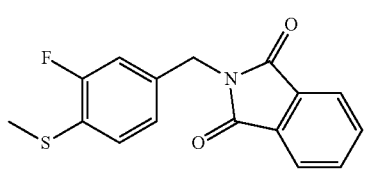 [SMILES: CSc1ccc(CN2C(=O)c3ccccc3C2=O)cc1F]

A mixture of 3-fluoro-4-methylsulfanyl-benzonitrile (6.00 g, 34.1 mmol), Raney-Nickel (100 mg) and concentrated aqueous ammonia (30 mL) in methanol (300 mL) is treated with hydrogen (3.4 bar) at room temperature for 3 h. The mixture is filtered through a pad of silica gel, and the filtrate is concentrated under reduced pressure.

The residue is dissolved in toluene (250 mL), and the mixture is treated with phthalic anhydride (4.0 g, 26.3 mmol) and triethylamine (0.98 g, 9.50 mmol) and heated at reflux over night. All volatiles are removed, and the residue is recrystallized from ethanol. Yield: 4.50 g (43% of theory). ESI mass spectrum: [M+H]⁺=302; Retention time HPLC: 0.67 min (X012_S01).

32b: 3-Fluoro-4-methanesulfonyl-benzylamine

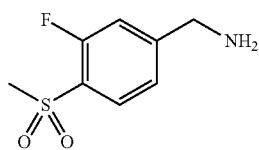

3-Chloroperoxybenzoic acid (77%, 8.3 g, 37.2 mmol) is added to a mixture of 2-(3-fluoro-4-methylsulfanyl-benzyl)-isoindole-1,3-dione (preparation 32a, 6.00 g, 18.9 mmol) and dichloromethane (580 mL). After 1 h saturated aqueous sodium thiosulfate solution is added, and the mixture is extracted with dichloromethane. The organic layer is dried under reduced pressure, and the residue is purified by flash chromatography on silica (cyclohexane/ethyl acetate 5:1).

The purified intermediate 2-(3-fluoro-4-methylsulfonyl-benzyl)-isoindole-1,3-dione (5.50 g, 15.6 mmol) is dissolved in a mixture of methanol (250 mL) and dichloromethane (250 mL). Hydrazine hydrate (4.6 g, 78.4 mmol) is added, and the mixture is stirred at 60° C. for 3 h. The mixture is filtered, and the filtrate is treated with water. The mixture is extracted with ethyl acetate, and the organic layer is dried over Na₂SO₄ and concentrated under reduced pressure. The residue is purified by preparative reversed-phase HPLC (Luna C18 250*50 mm, gradient of acetonitrile in water, 0.1% TFA). Yield: 3.1 g (81% of theory); ESI mass spectrum: [M+H]⁺=204; Retention time HPLC: 0.17 min (X012_S01).

Example 32

1-Isopropyl-6-methyl-4-oxo-5-(3-trifluoromethyl-phenyl)-1,4-dihydro-pyridine-3-carboxylic acid 3-fluoro-4-methanesulfonyl-benzylamide

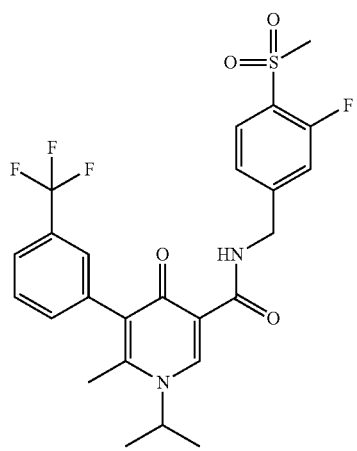 [SMILES: Cc1c(-c2cccc(C(F)(F)F)c2)c(=O)c(C(=O)NCc2ccc(S(C)(=O)=O)c(F)c2)cn1C(C)C]

To a solution of 1-isopropyl-6-methyl-4-oxo-5-(3-trifluoromethyl-phenyl)-1,4-dihydro-pyridine-3-carboxylic acid (preparation 3, 60 mg, 0.177 mmol), preparation 32b (72 mg, 0.354 mmol), N-methylmorpholine (0.10 mL, 0.910 mmol) in dichloromethane (1 mL) is added at 0° C. 1-propanephosphonic acid cyclic anhydride in ethyl acetate (0.31 mL, 50%, 0.53 mmol). The reaction mixture is stirred for 18 h at room temperature. The volatiles are evaporated under reduced pressure and the remaining residue is purified by preparative reversed-phase HPLC (Sunfire, gradient of acetonitrile in water, 0.1% TFA, 60° C.). Yield: 24 mg (26% of theory); ESI mass spectrum: [M+H]⁺=525; Retention time HPLC: 0.86 min (005_CA01).

Example 33

5-(3-Difluoromethyl-phenyl)-1-isopropyl-6-methyl-4-oxo-1,4-dihydro-pyridine-3-carboxylic acid 3-fluoro-4-methanesulfonyl-benzylamide

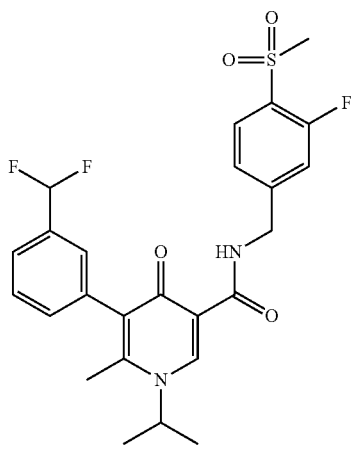 [SMILES: Cc1c(-c2cccc(C(F)F)c2)c(=O)c(C(=O)NCc2ccc(S(C)(=O)=O)c(F)c2)cn1C(C)C]

Example 33 is prepared as described for Example 32, substituting preparation 3 with preparation 4. ESI mass spectrum: [M+H]⁺=507; Retention time HPLC: 0.54 min (001_CA07).

Example 34

1-Isopropyl-6-methyl-4-oxo-5-(3-trifluoromethyl-phenyl)-1,4-dihydro-pyridine-3-carboxylic acid 2-fluoro-4-methanesulfonyl-benzylamide

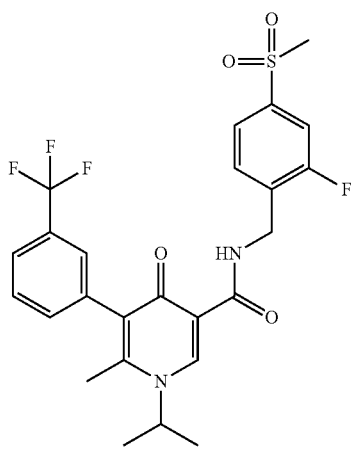

34a: 2-Fluoro-4-methylsulfanyl-benzylamine

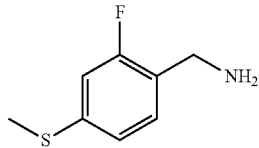

A mixture of 2-fluoro-4-methylsulfanyl-benzonitrile (8.0 g, 45.5 mmol), Raney-Nickel (20.0 g) and concentrated aqueous ammonia (300 mL) in methanol (3.0 L) is treated with hydrogen (3.4 bar) at room temperature and stirred over night. The mixture is filtered through a pad of silica gel, and the filtrate is concentrated under reduced pressure. Yield: 6.3 g (81% of theory); ESI mass spectrum: $[M+H—NH_3]^+=155$; Retention time HPLC: 1.38 min (0-30AB).

34b: 2-(2-Fluoro-4-methylsulfanyl-benzyl)-isoindole-1,3-dione

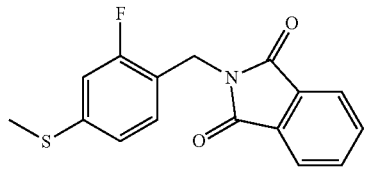 [SMILES: CSc1ccc(CN2C(=O)c3ccccc3C2=O)c(F)c1]

A mixture of 2-fluoro-4-methylsulfanyl-benzylamine (preparation 34a, 10.0 g, 52.6 mmol) and phthalic anhydride (7.94 g, 52.6 mmol) in toluene (510 mL) is heated at reflux over night. All volatiles are removed under reduced pressure, and the residue is recrystallized from hot ethanol. Yield: 9.2 g (55% of theory); ESI mass spectrum: $[M+Na]^+=302$; Retention time HPLC: 0.67 min (X012_S01).

34c: 2-Fluoro-4-methanesulfonyl-benzylamine

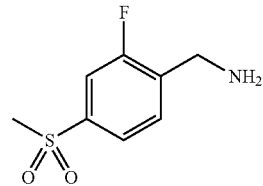

Preparation 34c is prepared in analogy to preparation 32b, using 2-(2-fluoro-4-methylsulfanyl-benzyl)-isoindole-1,3-dione (preparation 34b) as starting material. ESI mass spectrum: $[M+H]^+=204$; Retention time HPLC: 1.40 min (0-30HPLC).

Example 34

1-Isopropyl-6-methyl-4-oxo-5-(3-trifluoromethyl-phenyl)-1,4-dihydro-pyridine-3-carboxylic acid 2-fluoro-4-methanesulfonyl-benzylamide

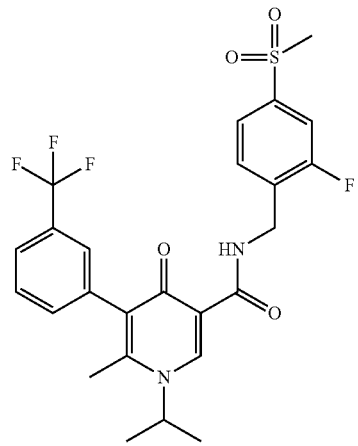

Example 34 is prepared as described for Example 32, substituting preparation 32b with preparation 34c. ESI mass spectrum: $[M+H]^+=525$; Retention time HPLC: 0.86 min (005_CA01).

Example 35

5-(3-Difluoromethyl-phenyl)-1-isopropyl-6-methyl-4-oxo-1,4-dihydro-pyridine-3-carboxylic acid 2-fluoro-4-methanesulfonyl-benzylamide

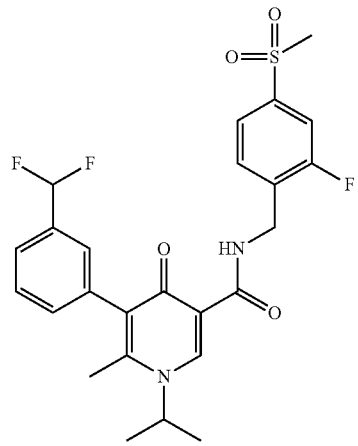 [SMILES: Cc1c(-c2cccc(C(F)F)c2)c(=O)c(C(=O)NCc2ccc(S(C)(=O)=O)cc2F)cn1C(C)C]

Example 35 is prepared as described for Example 32, substituting preparation 32b with preparation 34c and substituting preparation 3 with preparation 4. ESI mass spectrum: [M+H]$^+$=507; Retention time HPLC: 0.53 min (002_CA07).

Example 36

1-Isopropyl-6-methyl-4-oxo-5-(3-trifluoromethyl-phenyl)-1,4-dihydro-pyridine-3-carboxylic acid 4-methanesulfonyl-2-methyl-benzylamide

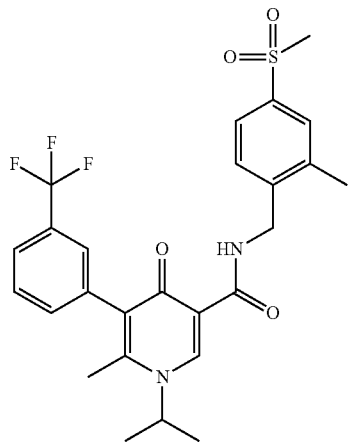 [SMILES: Cc1cc(S(C)(=O)=O)ccc1CNC(=O)c1cn(C(C)C)c(C)c(-c2cccc(C(F)(F)F)c2)c1=O]

36a: 2-(4-Methanesulfanyl-2-methyl-benzyl)-isoindole-1,3-dione

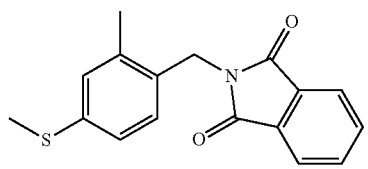 [SMILES: CSc1ccc(CN2C(=O)c3ccccc3C2=O)c(C)c1]

A mixture of 2-methyl-4-methylsulfanyl-benzonitrile (prepared as described in WO09126863, 2.3 g, 14 mmol), Raney-Nickel (1.0 g) and concentrated aqueous ammonia (50 mL) in methanol (200 mL) is treated with hydrogen (3.4 bar) at room temperature over night. The mixture is filtered, and all volatiles are removed under reduced pressure. The residue (2.3 g, 11.0 mmol based on 80% purity) is mixed with phthalic anhydride (1.66 g, 11.0 mmol), triethylamine (450 mg, 4.40 mmol) and toluene (100 mL), and the mixture is heated at 90° C. over night. All volatiles were removed under reduced pressure, and the residue is recrystallized from hot ethanol. Yield: 1.30 g (31% of theory); ESI mass spectrum: [M+H]$^+$=298; Retention time HPLC: 0.70 min (X011_S03).

36b: 4-Methanesulfonyl-2-methyl-benzylamine

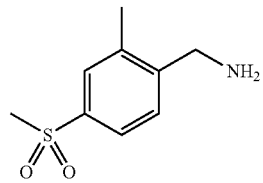

Preparation 36b is prepared in analogy to preparation 32b, using 2-(4-methanesulfanyl-2-methyl-benzyl)-isoindole-1, 3-dione (preparation 36a) as starting material. ESI mass spectrum: [M+H]$^+$=200; Retention time HPLC: 2.12 min (CD00).

Example 36

1-Isopropyl-6-methyl-4-oxo-5-(3-trifluoromethyl-phenyl)-1,4-dihydro-pyridine-3-carboxylic acid 4-methanesulfonyl-2-methyl-benzylamide

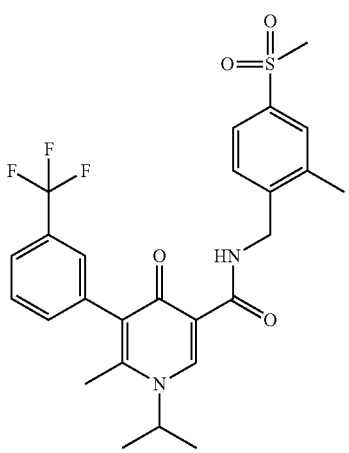 [SMILES: Cc1cc(S(C)(=O)=O)ccc1CNC(=O)c1cn(C(C)C)c(C)c(-c2cccc(C(F)(F)F)c2)c1=O]

Example 36 is prepared as described for Example 32, substituting preparation 32b with preparation 36b. ESI mass spectrum: [M+H]$^+$=521; Retention time HPLC: 0.86 min (005_CA01).

Example 37

5-(3-Difluoromethyl-phenyl)-1-isopropyl-6-methyl-4-oxo-1,4-dihydro-pyridine-3-carboxylic acid 4-methanesulfonyl-2-methyl-benzylamide

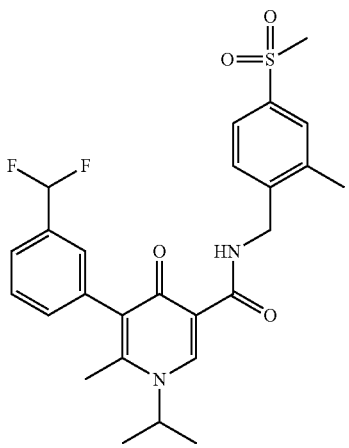 [SMILES: Cc1cc(S(C)(=O)=O)ccc1CNC(=O)c1cn(C(C)C)c(C)c(-c2cccc(C(F)F)c2)c1=O]

Example 37 is prepared as described for Example 32, substituting preparation 32b with preparation 36b and substituting preparation 3 with preparation 4. ESI mass spectrum: [M+H]⁺=503; Retention time HPLC: 0.54 min (001_CA07).

Example 38

1-Isopropyl-6-methyl-4-oxo-5-(3-trifluoromethyl-phenyl)-1,4-dihydro-pyridine-3-carboxylic acid (1,1-dioxo-2,3-dihydro-1H-1λ⁶-imidazo[2,1-b]thiazol-6-ylmethyl)-amide

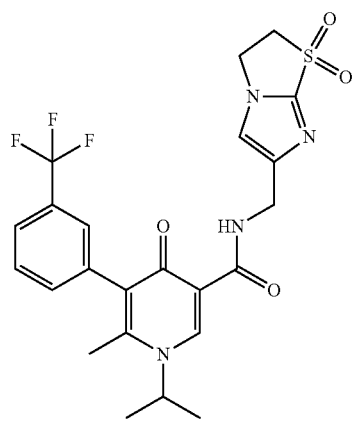 [SMILES: Cc1c(-c2cccc(C(F)(F)F)c2)c(=O)c(C(=O)NCc2cn3c(n2)S(=O)(=O)CC3)cn1C(C)C]

38a 1-Isopropyl-6-methyl-4-oxo-5-(3-trifluoromethyl-phenyl)-1,4-dihydro-pyridine-3-carboxylic acid (2,3-dihydro-imidazo[2,1-b]thiazol-6-ylmethyl)-amide

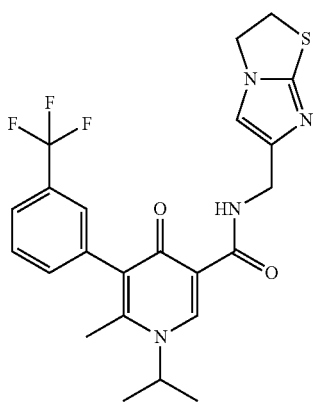 [SMILES: Cc1c(-c2cccc(C(F)(F)F)c2)c(=O)c(C(=O)NCc2cn3c(n2)SCC3)cn1C(C)C]

Preparation 38a is prepared as described for Preparation 5, substituting preparation 3c with preparation 3 and substituting 4-methylsulfonylbenzylamine hydrochloride with 5,7-dihydroimidazo[1,2-C]thiazol-2-ylmethanamine (Chem-bridge). ESI mass spectrum: [M+H]⁺=477; Retention time HPLC: 0.59 min (005_CA01).

Example 38

1-Isopropyl-6-methyl-4-oxo-5-(3-trifluoromethyl-phenyl)-1,4-dihydro-pyridine-3-carboxylic acid (1,1-dioxo-2,3-dihydro-1H-1λ⁶-imidazo[2,1-b]thiazol-6-ylmethyl)-amide

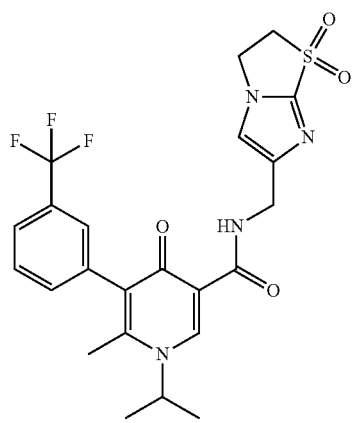 [SMILES: Cc1c(-c2cccc(C(F)(F)F)c2)c(=O)c(C(=O)NCc2cn3c(n2)S(=O)(=O)CC3)cn1C(C)C]

3-Chloroperoxybenzoic acid (26 mg, 0.15 mmol) is added to a solution of preparation 38a (33 mg, 0.069 mmol) in dichloromethane (3 mL). The reaction mixture is stirred for 6 h at room temperature. The volatiles are removed under reduced pressure and the remaining residue is purified by preparative reversed-phase HPLC. Yield: 6 mg (17% of theory); ESI mass spectrum: [M+H]⁺=509; Retention time HPLC: 0.96 min (Z018_S04).

Example 39

1-Isopropyl-6-methyl-4-oxo-5-(3-trifluoromethyl-phenyl)-1,4-dihydro-pyridine-3-carboxylic acid (5-methanesulfonyl-thiophen-2-ylmethyl)-amide

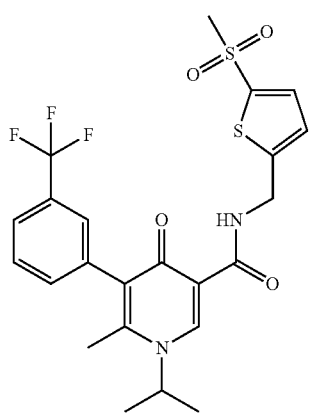 [SMILES: Cc1c(-c2cccc(C(F)(F)F)c2)c(=O)c(C(=O)NCc2ccc(S(C)(=O)=O)s2)cn1C(C)C]

39a 5-Bromo-1-isopropyl-6-methyl-4-oxo-1,4-dihydro-pyridine-3-carboxylic acid (5-methanesulfonyl-thiophen-2-ylmethyl)-amide

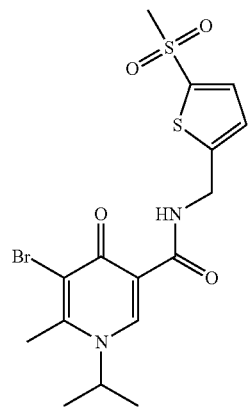 [SMILES: Cc1c(Br)c(=O)c(C(=O)NCc2ccc(S(C)(=O)=O)s2)cn1C(C)C]

Preparation 39a is prepared following the procedure for preparation 5, substituting 4-methylsulfonylbenzylamine hydrochloride with (5-methanesulfonylthiophen-2-yl)methanamine hydrochloride (Enamine) ESI mass spectrum: [M+H]+=447 (bromine isotope pattern); Retention time HPLC: 0.71 min (Z011_S03).

Example 39

1-Isopropyl-6-methyl-4-oxo-5-(3-trifluoromethyl-phenyl)-1,4-dihydro-pyridine-3-carboxylic acid (5-methanesulfonyl-thiophen-2-ylmethyl)-amide

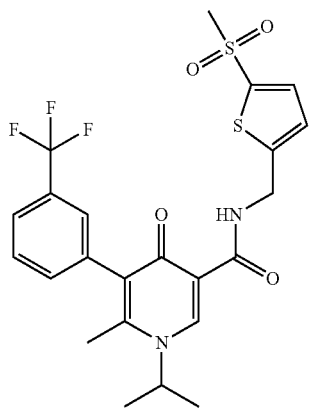 [SMILES: Cc1c(-c2cccc(C(F)(F)F)c2)c(=O)c(C(=O)NCc2ccc(S(C)(=O)=O)s2)cn1C(C)C]

Example 39 is prepared following the procedure for Example 24.1, substituting preparation 24 with preparation 39a. ESI mass spectrum: [M+H]$^+$=513; Retention time HPLC: 0.89 min (Z011_S03).

Example 40

5-(3-Difluoromethyl-phenyl)-1-isopropyl-6-methyl-4-oxo-1,4-dihydro-pyridine-3-carboxylic acid (5-methanesulfonyl-thiophen-2-ylmethyl)-amide

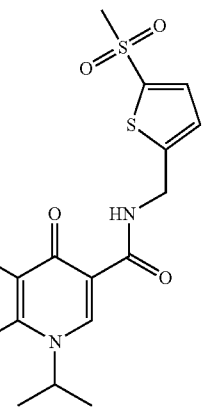

Example 40 is prepared following the procedure for Example 24.1, substituting preparation 24 with preparation 39a and replacing 3-(trifluoromethyl)phenylboronic acid with 3-(difluoromethyl)phenylboronic acid. ESI mass spectrum: [M+H]$^+$=495; Retention time HPLC: 0.82 min (Z011_S03).

Example 41

(S)-1-(2-Methoxy-1-methyl-ethyl)-6-methyl-4-oxo-5-(3-trifluoromethyl-phenyl)-1,4-dihydro-pyridine-3-carboxylic acid 4-methanesulfonyl-benzylamide

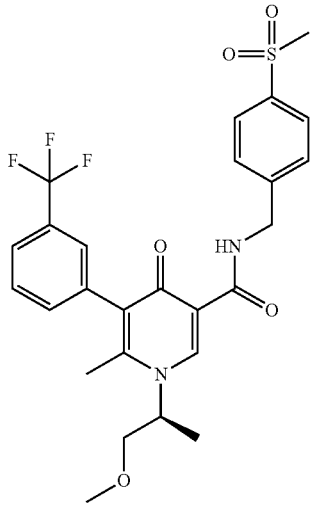 [SMILES: COC[C@H](C)n1cc(C(=O)NCc2ccc(S(C)(=O)=O)cc2)c(=O)c(-c2cccc(C(F)(F)F)c2)c1C]

41a (S)-1-(2-Methoxy-1-methyl-ethyl)-6-methyl-4-oxo-1,4-dihydro-pyridine-3-carboxylic acid

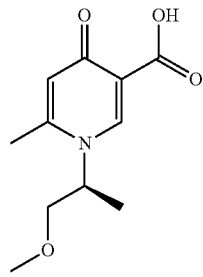 [SMILES: COC[C@H](C)n1cc(C(=O)O)c(=O)cc1C]

Preparation 41a is prepared following the procedure for preparation 3b, substituting isopropylamine with (S)-1-methoxy-2-propylamine. ESI mass spectrum: [M+H]$^+$=226; Retention time HPLC: 0.65 min (Z018_S04).

41b (S)-5-Bromo-1-(2-methoxy-1-methyl-ethyl)-6-methyl-4-oxo-1,4-dihydro-pyridine-3-carboxylic acid

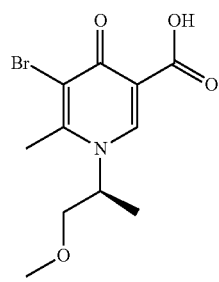 [SMILES: COC[C@H](C)n1cc(C(=O)O)c(=O)c(Br)c1C]

Preparation 41b is prepared following the procedure for preparation 3c, substituting preparation 3b with preparation 41a. ESI mass spectrum: [M+H]$^+$=304 (bromine isotope pattern); Retention time HPLC: 0.81 min (Z018_S04).

41c (S)-5-Bromo-1-(2-methoxy-1-methyl-ethyl)-6-methyl-4-oxo-1,4-dihydro-pyridine-3-carboxylic acid 4-methanesulfonyl-benzylamide

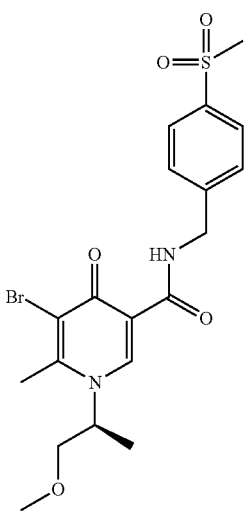 [SMILES: COC[C@H](C)n1cc(C(=O)NCc2ccc(S(C)(=O)=O)cc2)c(=O)c(Br)c1C]

Preparation 41c is prepared following the procedure for preparation 5, substituting preparation 3c with preparation 41b. ESI mass spectrum: [M+H]$^+$=471 (bromine isotope pattern); Retention time HPLC: 0.88 min (Z018_S04).

Example 41

(S)-1-(2-Methoxy-1-methyl-ethyl)-6-methyl-4-oxo-5-(3-trifluoromethyl-phenyl)-1,4-dihydro-pyridine-3-carboxylic acid 4-methanesulfonyl-benzylamide

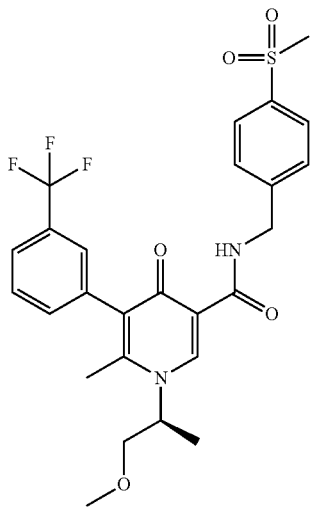 [SMILES: COC[C@H](C)n1cc(C(=O)NCc2ccc(S(C)(=O)=O)cc2)c(=O)c(-c2cccc(C(F)(F)F)c2)c1C]

Example 41 is prepared following the procedure for Example 24.1, substituting preparation 24 with preparation 41c. ESI mass spectrum: [M+H]$^+$=537; Retention time HPLC: 1.02 min (Z018_S04).

Example 42

(S)-5-(3-Difluoromethyl-phenyl)-1-(2-methoxy-1-methyl-ethyl)-6-methyl-4-oxo-1,4-dihydro-pyridine-3-carboxylic acid 4-methanesulfonyl-benzylamide

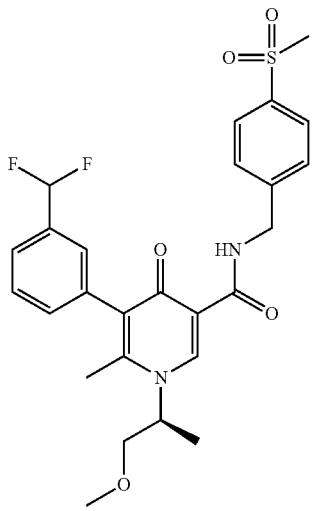 [SMILES: COC[C@H](C)n1cc(C(=O)NCc2ccc(S(C)(=O)=O)cc2)c(=O)c(-c2cccc(C(F)F)c2)c1C]

Example 42 is prepared following the procedure for Example 24.1, substituting preparation 24 with preparation 41c and replacing 3-(trifluoromethyl)phenylboronic acid with 3-(difluoromethyl)phenylboronic acid. ESI mass spectrum: [M+H]$^+$=519; Retention time HPLC: 0.97 min (Z018_S04).

Example 43

(R)-1-(2-Methoxy-1-methyl-ethyl)-6-methyl-4-oxo-5-(3-trifluoromethyl-phenyl)-1,4-dihydro-pyridine-3-carboxylic acid 4-methanesulfonyl-benzylamide

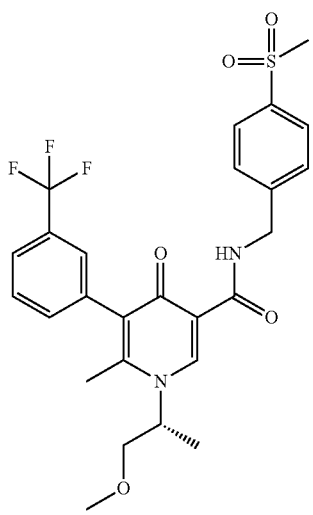

43a (R)-1-(2-Methoxy-1-methyl-ethyl)-6-methyl-4-oxo-1,4-dihydro-pyridine-3-carboxylic acid

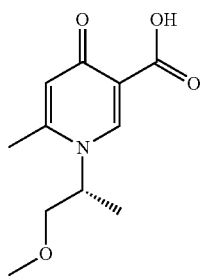 [SMILES: COC[C@@H](C)n1cc(C(=O)O)c(=O)cc1C]

Preparation 43a is prepared following the procedure for preparation 3b, substituting isopropylamine with (R)-1-methoxy-2-propylamine. ESI mass spectrum: [M+H]$^+$=226; Retention time HPLC: 0.65 min (Z018_S04).

43b (R)-5-Bromo-1-(2-methoxy-1-methyl-ethyl)-6-methyl-4-oxo-1,4-dihydro-pyridine-3-carboxylic acid

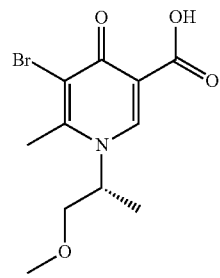 [SMILES: COC[C@@H](C)n1cc(C(=O)O)c(=O)c(Br)c1C]

Preparation 43b is prepared following the procedure for preparation 3c, substituting preparation 3b with preparation 43a. ESI mass spectrum: [M+H]$^+$=304 (bromine isotope pattern); Retention time HPLC: 0.81 min (Z018_S04).

43c (R)-5-Bromo-1-(2-methoxy-1-methyl-ethyl)-6-methyl-4-oxo-1,4-dihydro-pyridine-3-carboxylic acid 4-methanesulfonyl-benzylamide

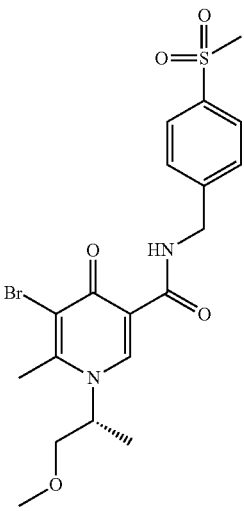

Preparation 43c is prepared following the procedure for preparation 5, substituting preparation 3c with preparation 43b. ESI mass spectrum: [M+H]⁺=471 (bromine isotope pattern); Retention time HPLC: 0.88 min (Z018_S04).

Example 43

(R)-1-(2-Methoxy-1-methyl-ethyl)-6-methyl-4-oxo-5-(3-trifluoromethyl-phenyl)-1,4-dihydro-pyridine-3-carboxylic acid 4-methanesulfonyl-benzylamide

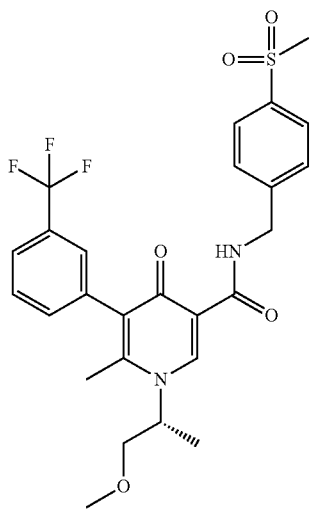 [SMILES: COC[C@@H](C)n1cc(C(=O)NCc2ccc(S(C)(=O)=O)cc2)c(=O)c(-c2cccc(C(F)(F)F)c2)c1C]

Example 43 is prepared following the procedure for Example 24.1, substituting preparation 24 with preparation 43c. ESI mass spectrum: [M+H]⁺=537; Retention time HPLC: 1.04 min (Z018_S04).

Example 44

(R)-5-(3-Difluoromethyl-phenyl)-1-(2-methoxy-1-methyl-ethyl)-6-methyl-4-oxo-1,4-dihydro-pyridine-3-carboxylic acid 4-methanesulfonyl-benzylamide

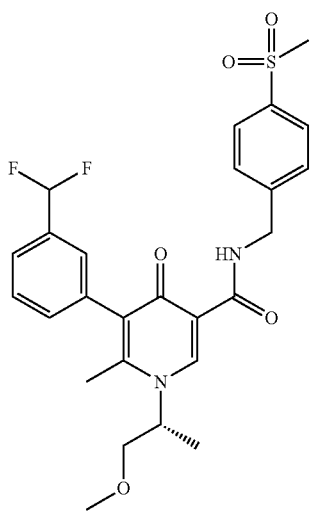 [SMILES: COC[C@@H](C)n1cc(C(=O)NCc2ccc(S(C)(=O)=O)cc2)c(=O)c(-c2cccc(C(F)F)c2)c1C]

Example 44 is prepared following the procedure for Example 24.1, substituting preparation 24 with preparation 43c and replacing 3-(trifluoromethyl)phenylboronic acid with 3-(difluoromethyl)phenylboronic acid. ESI mass spectrum: [M+H]⁺=519; Retention time HPLC: 0.97 min (Z018_S04).

Example 45

1-(2-Fluoro-ethyl)-6-methyl-4-oxo-5-(3-trifluoromethyl-phenyl)-1,4-dihydro-pyridine-3-carboxylic acid 4-methanesulfonyl-benzylamide

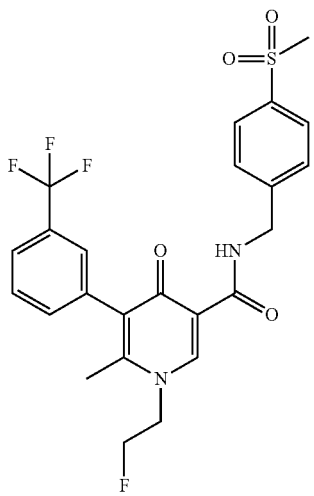 [SMILES: Cc1c(-c2cccc(C(F)(F)F)c2)c(=O)c(C(=O)NCc2ccc(S(C)(=O)=O)cc2)cn1CCF]

Example 45 is prepared as described for Example 1.1, substituting iodoethane with 1-bromo-2-fluoroethane and substituting DMF with NMP. ESI mass spectrum: [M+H]⁺= 511; Retention time HPLC: 0.99 min (Z018_S04).

Example 46

1-(2,2-Difluoro-ethyl)-6-methyl-4-oxo-5-(3-trifluoromethyl-phenyl)-1,4-dihydro-pyridine-3-carboxylic acid 4-methanesulfonyl-benzylamide

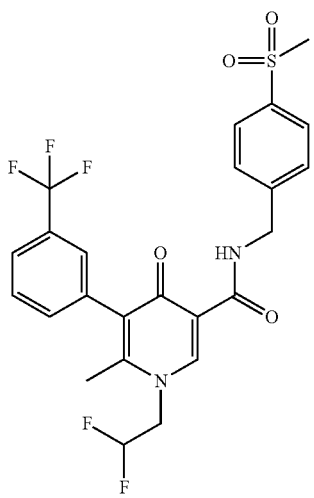 [SMILES: Cc1c(-c2cccc(C(F)(F)F)c2)c(=O)c(C(=O)NCc2ccc(S(C)(=O)=O)cc2)cn1CC(F)F]

Example 46 is prepared as described for Example 1.1, substituting iodoethane with 2-bromo-1,1-difluoroethane and substituting DMF with NMP. ESI mass spectrum: [M+H]$^+$=529; Retention time HPLC: 0.86 min (Z011_S03).

Example 47

1-Isopropyl-6-methyl-4-oxo-5-(3-trifluoromethyl-phenyl)-1,4-dihydro-pyridine-3-carboxylic acid 4-methanesulfonyl-2-methoxy-benzylamide

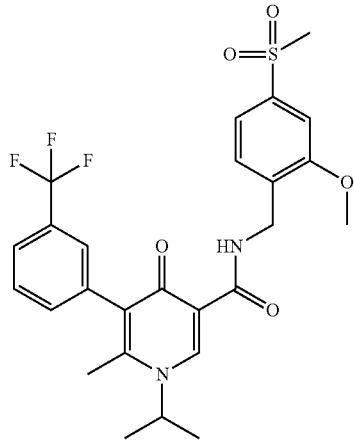 [SMILES: COc1cc(S(C)(=O)=O)ccc1CNC(=O)c1cn(C(C)C)c(C)c(-c2cccc(C(F)(F)F)c2)c1=O]

Example 47 is prepared as described for Example 32, substituting preparation 32b with 4-methanesulfonyl-2-methoxy-benzylamine (preparation described in WO2006/67462). ESI mass spectrum: [M+H]$^+$=537; Retention time HPLC: 1.03 min (Z017_S04).

Example 48

1-Isopropyl-6-methyl-4-oxo-5-(3-trifluoromethyl-phenyl)-1,4-dihydro-pyridine-3-carboxylic acid (1,1-dioxo-1H-1λ$^6$-benzo[b]thiophen-5-ylmethyl)-amide

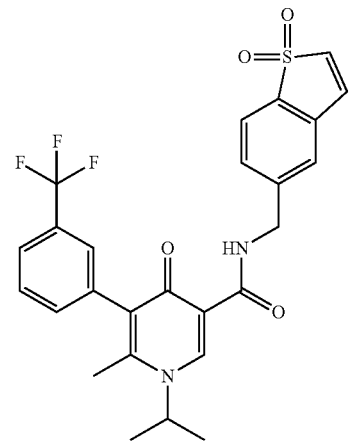

48a: Benzo[b]thiophen-5-ylmethyl-carbamic acid tert-butyl ester

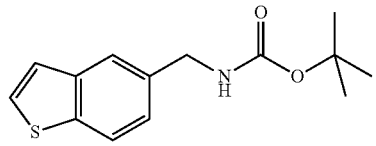 [SMILES: CC(C)(C)OC(=O)NCc1ccc2sccc2c1]

Di-tert-butyl dicarbonate (3.88 g, 17.5 mmol) is added to a solution of benzo[b]thiophen-5-ylmethanamine (prepared as described in WO01068652, 2.00 g, 11.6 mmol) and triethylamine (1.78 g, 17.5 mmol) in dichloromethane (40 mL), and the mixture is stirred at room temperature for 1 h. Water is added, and the mixture is extracted three times with dichloromethane. The combined organic layers are dried over Na$_2$SO$_4$, concentrated under reduced pressure. The residue is crystallized from hot petroleum ether. Yield: 1.26 g; ESI mass spectrum: [M–C$_4$H$_8$+H]$^+$=208; Retention time HPLC: 0.84 min (5-95AB).

48b: (1,1-Dioxo-1H-1$^6$-benzo[b]thiophen-5-ylmethyl)-carbamic acid tert-butyl ester

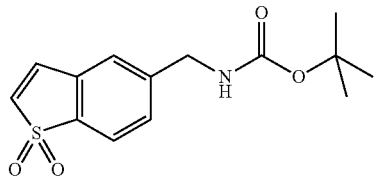 [SMILES: CC(C)(C)OC(=O)NCc1ccc2c(c1)C=CS2(=O)=O]

3-Chloroperoxybenzoic acid (77%, 1.58 g, 7.1 mmol) is added to a mixture of benzo[b]thiophen-5-ylmethyl-carbamic acid tert-butyl ester (preparation 48a, 1.00 g, 3.60 mmol) in dichloromethane, and the mixture is stirred at room temperature for 1 h. Saturated aqueous sodium thiosulfate solution is added, and the mixture is extracted three times with dichloromethane. The combined organic layers are dried over Na$_2$SO$_4$ and concentrated under reduced pressure. The residue is purified by flash chromatography on silica (petroleum gradient: ether/ethyl acetate 4:1 to 2:1). Yield: 770 mg (72% of theory). ESI mass spectrum: [M–C$_4$H$_8$+H]$^+$=240; Retention time HPLC: 0.72 min (5-95AB).

48c: C-(1,1-Dioxo-1H-1$^6$-benzo[b]thiophen-5-yl)-methylamine

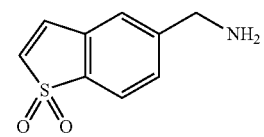 [SMILES: NCc1ccc2c(c1)C=CS2(=O)=O]

A solution of hydrogen chloride in ethyl acetate (4.0 M, 20 mL, 80 mmol) is added to a solution of (1,1-dioxo-1H-1$^6$-benzo[b]thiophen-5-ylmethyl)-carbamic acid tert-butyl ester (preparation 48b, 800 mg, 2.10 mmol) in dichloromethane (5 mL), and the mixture was stirred at room temperature for 1 h. The mixture was filtered, and the precipitate was washed twice with ethyl acetate. Yield: 480 mg (97% of theory); ESI mass spectrum: [M+H]⁺=196; Retention time HPLC: 0.13 min (5-95AB).

Example 48

1-Isopropyl-6-methyl-4-oxo-5-(3-trifluoromethyl-phenyl)-1,4-dihydro-pyridine-3-carboxylic acid (1,1-dioxo-1H-1⁶-benzo[b]thiophen-5-ylmethyl)-amide

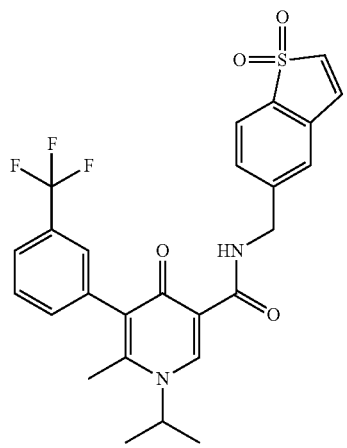 [SMILES: Cc1c(-c2cccc(C(F)(F)F)c2)c(=O)c(C(=O)NCc2ccc3c(c2)C=CS3(=O)=O)cn1C(C)C]

Example 48 is prepared as described for Example 3.1, substituting C-(5-Methyl-[1,3,4]oxadiazol-2-yl)-methylamine with preparation 48c and substituting N-methylmorpholine with triethylamine. ESI mass spectrum: [M+H]⁺=517; Retention time HPLC: 0.85 min (005_CA01).

Example 49

1-Isopropyl-6-methyl-4-oxo-5-(3-trifluoromethyl-phenyl)-1,4-dihydro-pyridine-3-carboxylic acid 4-methanesulfonyl-3-methoxy-benzylamide

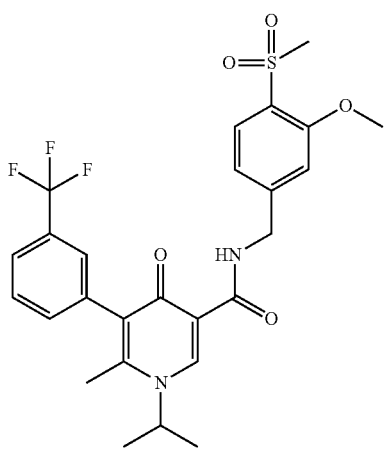 [SMILES: COc1cc(CNC(=O)c2cn(C(C)C)c(C)c(-c3cccc(C(F)(F)F)c3)c2=O)ccc1S(C)(=O)=O]

Example 49 is prepared as described for Example 32, substituting preparation 32b with 4-methanesulfonyl-3-methoxy-benzylamine (preparation described in WO2004/43924). ESI mass spectrum: [M+H]⁺=537; Retention time HPLC: 1.03 min (Z018_S04).

Example 50

5-(3-Difluoromethyl-phenyl)-1-isopropyl-6-methyl-4-oxo-1,4-dihydro-pyridine-3-carboxylic acid (1,1-dioxo-1H-1λ⁶-benzo[b]thiophen-5-ylmethyl)-amide1

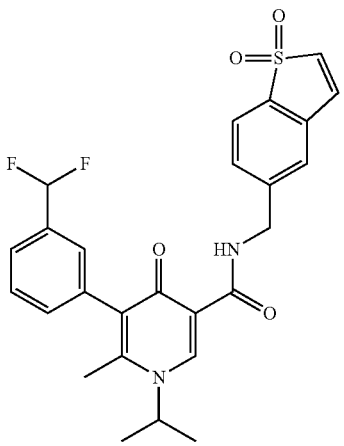 [SMILES: Cc1c(-c2cccc(C(F)F)c2)c(=O)c(C(=O)NCc2ccc3c(c2)C=CS3(=O)=O)cn1C(C)C]

Example 50 is prepared as described for Example 32, substituting preparation 3 with preparation 4 and substituting preparation 32b with preparation 48c. ESI mass spectrum: [M+H]⁺=499; Retention time HPLC: 0.54 min (001_CA07).

EXAMPLES

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat. No.: 324681) and the elastase substrate MeOSuc-Ala-Ala-Pro-Val-AMC from Bachem (Cat. No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 µL of these compound dilutions were mixed with 10 µl Neutrophil elastase (9 ng/ml in assay buffer) in a black 384 well OptiPlate (Perkin Elmer, Cat No.: 6007270) and incubated for 15 min at room temperature. Subsequently 10 µL substrate solution in assay buffer were added (250 µM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). IC50 values were estimated using a sigmoidal concentration response curve with variable slope. Means of low values were taken as 0%, means of high values as 100%. IC50 values of selected compound in the Neutrophil Elastase assay:

| Example | IC50 [nM] |
|---|---|
| 1.1 | 33 |
| 1.2 | 12 |
| 1.3 | 28 |
| 1.4 | 59 |
| 1.5 | 30 |
| 1.6 | 77 |
| 1.7 | 37 |
| 10 | 29 |
| 11.1 | 8 |
| 11.2 | 35 |
| 12.1 | 9 |
| 12.2 | 12 |
| 12.3 | 54 |
| 13 | 42 |
| 14.1 | 20 |
| 14.2 | 27 |
| 15.1 | 8 |
| 15.2 | 8 |
| 15.3 | 24 |
| 16 | 63 |
| 17.1 | 73 |
| 17.2 | 15 |
| 17.3 | 77 |
| 18.1 | 32 |
| 18.2 | 35 |
| 19.1 | 10 |
| 19.2 | 10 |
| 19.3 | 40 |
| 2.1 | 57 |
| 2.2 | 20 |
| 2.3 | 30 |
| 2.4 | 73 |
| 20.1 | 15 |
| 20.2 | 11 |
| 20.3 | 63 |
| 21 | 43 |
| 22 | 27 |
| 23.1 | 12 |
| 23.2 | 5 |
| 23.3 | 46 |
| 24.1 | 57 |
| 24.2 | 55 |
| 25.1 | 37 |
| 25.2 | 30 |
| 26 | 22 |
| 27.1 | 9 |
| 27.2 | 51 |
| 28.1 | 7 |
| 28.2 | 6 |
| 28.3 | 27 |
| 29.1 | 4 |
| 29.2 | 3 |
| 29.3 | 15 |
| 30.1 | 13 |
| 30.2 | 11 |
| 3.1 | 38 |
| 3.2 | 97 |
| 3.3 | 90 |
| 3.4 | 62 |
| 3.5 | 64 |
| 3.6 | 89 |
| 3.7 | 40 |
| 3.8 | 65 |
| 3.9 | 20 |
| 4.1 | 98 |
| 4.10 | 42 |
| 4.11 | 18 |
| 4.12 | 69 |
| 4.13 | 20 |
| 4.14 | 11 |
| 4.2 | 60 |
| 4.3 | 27 |
| 4.4 | 72 |
| 4.5 | 51 |
| 4.6 | 28 |
| 4.7 | 45 |
| 4.8 | 10 |
| 4.9 | 63 |
| 5.1 | 72 |
| 5.2 | 19 |
| 5.3 | 48 |
| 5.4 | 61 |
| 5.5 | 91 |
| 6 | 30 |
| 7 | 27 |
| 8.1 | 43 |
| 8.2 | 18 |
| 9.1 | 28 |
| 9.2 | 18 |
| 27.1A | 5.4 |
| 27.1B | 30 |
| 31 | 5.2 |
| 32 | 15 |
| 33 | 16 |
| 34 | 26 |
| 35 | 17 |
| 36 | 19 |
| 37 | 27 |
| 38 | 5.3 |
| 39 | 28 |
| 40 | 31 |
| 41 | 9.0 |
| 42 | 8.1 |
| 43 | 32 |
| 44 | 45 |
| 45 | 34 |
| 46 | 46 |
| 47 | 38 |
| 48 | 11 |
| 49 | 47 |
| 50 | 7.8 |

Determination of Aqueous Solubility from DMSO Stock Solutions ("Kinetic Solubility Method")

The aqueous solubility of examples of this invention is determined by comparing the amount dissolved in buffer to the amount dissolved in an acetonitrile/water (1/1) solution. Starting from a 10 mM DMSO stock solution, aliquots are diluted with acetonitrile/water (1/1) and McIlvaine buffer pH 6.8, respectively. After 24 h of shaking, the liquid phase is filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. According to this method, the aqueous solubility at pH 6.8 of example 4.14 is determined to be 0.076 mg/mL and the aqueous solubility at pH 6.8 of example 27.1A is determined to be 0.081 mg/mL.

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors Non-steroidale anti-inflammatory agents (NSAIDs), Cathepsin C (or DPPI/Dipeptidyl-aminopeptidase I) inhibitors, CRTH2 antagonists, DP1-receptor modulators, Thromboxane receptor antagonists, CCR3 antagonists, CCR4 antagonists, CCR1 antagonists, CCR5 antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic receptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:

Betamimetics with corticosteroids, PDE4-inhibitors, CRTH2-inhibitors or LTD4-antagonists,
Anticholinergics with betamimetics, corticosteroids, PDE4-inhibitors, CRTH2-inhibitors or LTD4-antagonists,
Corticosteroids with PDE4-inhibitors, CRTH2-inhibitors or LTD4-antagonists
PDE4-inhibitors with CRTH2-inhibitors or LTD4-antagonists
CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, acute lung injury (ALI); acute respiratory distress syndrome (ARDS);

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:

1. A compound of formula 1, wherein:

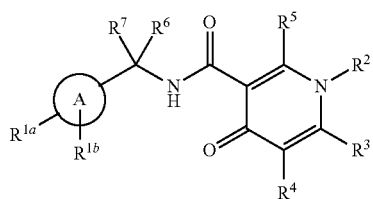

A is phenyl, oxadiazolyl, pyridinyl, pyridin-N-oxidyl, or thiophenyl;

$R^{1a}$ is H, methyl, NC—, Me(O)S—, Me(O)$_2$S—, Et(O)$_2$S—, H$_2$N(O)$_2$S—, imidazolidin-onyl, pyrrolidinon-H$_2$C—, or imidazol-H$_2$C—;

$R^{1b}$ is H;

$R^2$ is i-propyl;

$R^3$ is methyl;

$R^4$ is phenyl or pyridinyl, both substituted with F$_2$HC— or F$_3$C—;

$R^5$ is H;

$R^6$ is H; and $R^7$ is H;

or a salt thereof.

2. A pharmaceutical composition comprising a compound of formula 1 according to claim 1 or a pharmaceutically active salt thereof and a pharmaceutically acceptable carrier.

* * * * *